US010023900B2

(12) United States Patent
Seppälä

(10) Patent No.: US 10,023,900 B2
(45) Date of Patent: Jul. 17, 2018

(54) METHOD FOR QUANTIFICATION OF ALLERGENS

(71) Applicant: ALK-Abelló A/S, Hørsholm (DK)

(72) Inventor: Ulla Seppälä, Helsingborg (SE)

(73) Assignee: ALK-ABELLO A/S, Horsholm (DK)

( * ) Notice: Subject to any disclaimer, the term of this patent is extended or adjusted under 35 U.S.C. 154(b) by 0 days.

(21) Appl. No.: 14/198,112

(22) Filed: Mar. 5, 2014

(65) Prior Publication Data

US 2014/0206027 A1 Jul. 24, 2014

Related U.S. Application Data

(63) Continuation of application No. 12/066,908, filed as application No. PCT/DK2006/000480 on Sep. 1, 2006, now Pat. No. 8,703,903.

(60) Provisional application No. 60/717,942, filed on Sep. 16, 2005.

(30) Foreign Application Priority Data

Sep. 15, 2005 (DK) .................................. 2005 01293

(51) Int. Cl.
| | |
|---|---|
| *A61K 38/00* | (2006.01) |
| *A61K 38/04* | (2006.01) |
| *C07K 2/00* | (2006.01) |
| *C07K 4/00* | (2006.01) |
| *C07K 5/00* | (2006.01) |
| *C07K 7/00* | (2006.01) |
| *C07K 14/00* | (2006.01) |
| *C07K 16/00* | (2006.01) |
| *C07K 17/00* | (2006.01) |
| *C12Q 1/37* | (2006.01) |
| *G01N 33/68* | (2006.01) |

(52) U.S. Cl.
CPC ........... *C12Q 1/37* (2013.01); *G01N 33/6848* (2013.01); *G01N 2458/15* (2013.01); *G01N 2800/24* (2013.01)

(58) Field of Classification Search
None
See application file for complete search history.

(56) References Cited

U.S. PATENT DOCUMENTS

| | | |
|---|---|---|
| 6,319,476 B1 | 11/2001 | Victor, Jr. et al. |
| 6,864,089 B2 | 3/2005 | Figeys et al. |
| 6,872,575 B2 | 3/2005 | Regnier |
| 2004/0033625 A1 | 2/2004 | Aebersold |
| 2004/0072251 A1 | 4/2004 | Anderson |
| 2004/0106146 A1 | 6/2004 | Palosuo et al. |
| 2004/0229283 A1 | 11/2004 | Gygi et al. |
| 2006/0228769 A1* | 10/2006 | Yano .................. G01N 33/6815 435/25 |

FOREIGN PATENT DOCUMENTS

| | | | | |
|---|---|---|---|---|
| WO | WO 1995/02412 | * | 1/1995 | ............ A61K 37/02 |
| WO | WO 2003/102220 A2 | | 12/2003 | |
| WO | WO 2003/016861 A3 | | 8/2004 | |
| WO | WO 2004/070352 A2 | | 8/2004 | |
| WO | WO 2004/031730 A3 | | 1/2005 | |
| WO | WO 2005/022157 A1 | | 3/2005 | |

OTHER PUBLICATIONS

Chen et al.'Sequence Tag Catalogs of Dust Mite-Expressed Genomes.' Am J. Pharmacogenetics 4(6):357-369, 2004.*
National Center for Biotechnology Information, "The Statistics of Sequence Similarity Scores" retrieved from <http://www.ncbi.nlm.gov/BLAST/tutorial/Altschul-1.html> on Sep. 16, 2011, 13 pages.
Aebersold, R., et al., "Mass Spectrometry in Proteomics," *Chem. Rev.*, 2001, vol. 101, pp. 269-295.
Aasmul-Olsen, S., et al., "Characterization of Group 1 Allergens from Eleven Grass Species," *New Horizons in Allergy Immunotherapy*, 1996, pp. 261-265.
Applied Biosystems, "Applied Biosystems iTRAQ™ Reagents, Applied Biosystems," brochure, Apr. 2004, 96 pages.
Bronstrup, Mark, "Absolute quantification strategies in proteomics based on mass spectrometry," *Expert Rev. Proteomics*, 2004, vol. 1, pp. 503-112.
Campbell, D., et al., Analysing photosynthetic complexes in uncharacterized species or mixed microalgal communities using global antibodies, *Physiologia Plantarum*, 2003, vol. 119, pp. 322-327.

(Continued)

*Primary Examiner* — Nora Rooney
(74) *Attorney, Agent, or Firm* — Womble Bond Dickinson (US) LLP

(57) ABSTRACT

The invention relates to method for quantification of the absolute amount of allergen in an allergen sample comprising:

Figure 4:
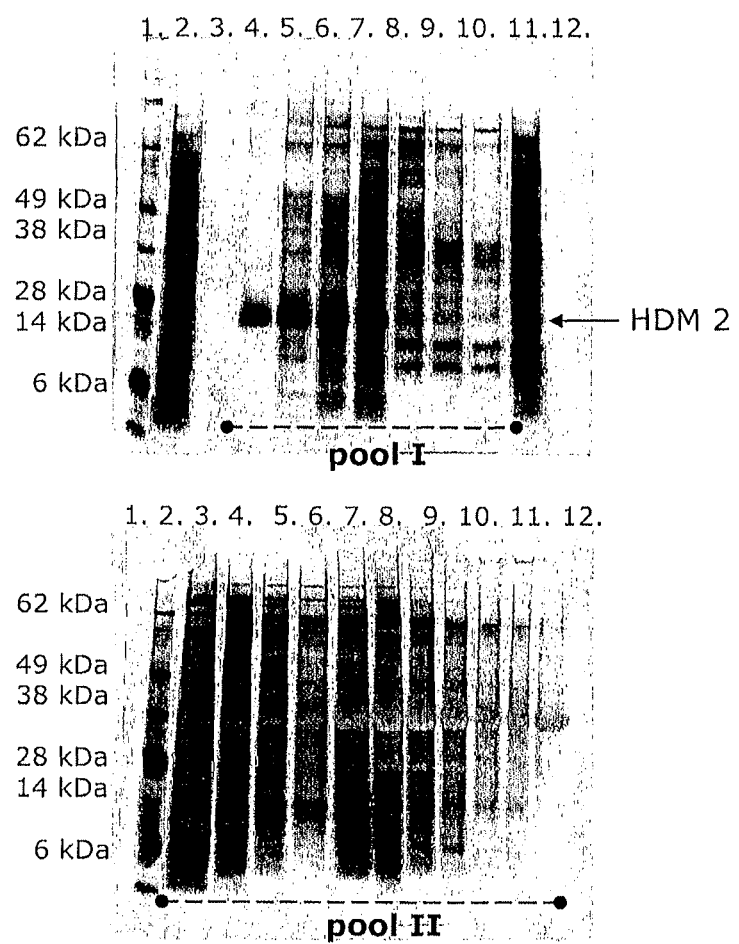

a) providing a known amount of one or more allergen calibration standard peptide(s) having a sequence of amino acids which is identical with, and optionally unique for, a sequence to be found in the allergen to be quantified and optionally labelling said allergen calibration standard peptide(s), b) degrading the allergen sample to obtain a mixture of peptides, and optionally labelling said peptides with one or more labelling agent(s), wherein at least the peptides in the degraded allergen sample or the calibration standard peptides are labelled, and if both the peptides in the degraded allergen sample and the allergen calibration standard peptide(s) are labelled, the labelling agent(s) used for labelling the allergen calibration standard peptide(s) are different from the labelling agent(s) used for labelling the peptides of the degraded allergen sample, c) quantifying the absolute amount of allergen by correlating the amount of the allergen calibration standard peptide(s) with the amount of the corresponding peptide(s) of the degraded allergen sample by mass analysis.

7 Claims, 14 Drawing Sheets

(56) References Cited

OTHER PUBLICATIONS

Chua, K., et al., "Analysis of sequence polymorphism of a major mite allergen, Der p 2," *Clinical and Experimental Allergy*, 1996, vol. 26, pp. 829-837.
Database Entry for Uniprot Accession No. P02759, Jul. 21, 1986.
Database Entry for Uniprot Accession No. P01241, Jul. 21, 1986.
Database Entry for Uniprot Accession No. P01308, Jul. 21, 1986.
Desiere, F., et al., "Integration with the human genome of peptide sequences obtained by high-throughput mass spectrometry," *Genome Biology*, 2004, vol. 6, Issue 1, Article R9.
Fenaille, F., et al., "Mass Spectrometric Investigation of Molecular Variability of Grass Pollen Group 1 Allergens," *Journal of Proteome Research*, 2009, vol. 8, pp. 4014-4027.
Gerber, S., et al., "Absolute Quantification of Proteins and Phosphoproteins from Cell Lysates by Tandem MS," *Proc. Natl. Acad. Sci. USA*, 2003, vol. 100(12), pp. 6940-6945.
Grounds of Appeal of Opponent, Nov. 9, 2012, filed in connection with opposition to counterpart EP application 06775965.4 (EP 1931998), 16 pages.
Guerrera, I., et al., "Application of Mass Spectrometry in Proteomics," *Bioscience Reports*, 2005, vol. 25, Nos. 1/2, pp. 71-93.
Hakkaart, G., et al., "Immune-reactivity of recombinant isoforms of the major house dust mite allergen Der p 2," *Clinical and Experimental Allergy*, 1998, vol. 28, pp. 169-174.
Harris, J., et al., "Activity Profile of Dust Mite Allergen Extract Using Substrate Libraries and Functional Proteomic Microarrays," *Chemistry & Biology*, 2004, vol. 11, pp. 1361-1372.
Heck, A., et al., "Mass spectrometry-based quantitative proteomics," *Expert Rev. Proteomics*, 2004, vol. 1, No. 3, pp. 317-326.
Helsper, J., et al., "Quadrupole time-of-flight mass spectrometry: A method to study the actual expression of allergen isoforms identified by PCR cloning," *J. Allergy Clin. Immunol.*, 2002, vol. 110(1), pp. 131-138.
Ipsen, H., et al., "Isolation and Immunochemical Characterization of the Major Allergen of Birch Pollen (*Betula verrucosa*)," *J. Allergy Clin Immunol.*, 1983, vol. 72(2), pp. 150-159.
ISMA 2010 Abstracts, Abstract #45, Seppälä, *4th International Symposium on Molecular Allergology*, Oct. 29-31, 2010, Munich, Germany.
Johannessen, B., et al., "Structure of the House Dust Mite Allerger Der F 2: Implications for Function and Molecular Basis of IgE Cross-Reactivity," *Federation of European Biochemical Societies(FEBS) Lett*, 2005, vol. 579, pp. 1208-1212.
King, T., et al., "World Health Organization/UIS Allergen Nomenclature," *J. Allergy Clin. Immuol.*, 1995, vol. 96, pp. 5-14.
Kristiansson, M., et al., "Correlations between air levels of hexahydrophthalic anhydride (HHPA) and HHPA-adducted albumin tryptic peptides in nasal lavage fluid from experimentally exposed volunteers," *Rapid Commun. Mass Spectrom.*, 2004, vol. 18(14), pp. 1592-1598.
Larsen, J., et al., "Manufacturing and Standardizing Allergen Extracts in Europe," *Allergens and Allergen Immunotherapy*, Fourth Edition, 2008, pp. 433,455.
Letter on behalf of opponent, Mar. 9, 2011, filed in connection with opposition to counterpart EP application 06775965.4 (EP 1931998), 9 pages.
Letter on behalf of patentee, Aug. 22, 2011, filed in connection with opposition to counterpart EP application 06775965.4 (EP 1931998), 14 pages.
Letter on behalf of opponent, Feb. 17, 2012, filed in connection with opposition to counterpart EP application 06775965.4 (EP 1931998), 8 pages.
Letter on behalf of patentee, Feb. 17, 2012, filed in connection with opposition to counterpart EP applications 06775965.4 (EP 1931998), 8 pages.
Nesvizhskii, A., et al., "A Statistical Model for Identifying Proteins by Tandem Mass Spectrometry," *Anal. Chem.*, 200., vol. 75, pp. 4646-4658.
Nesvizhskii, A., "Interpretation of Shotgun Proteomic Data, *Molecular & Cellular Proteomics*," 2005, vol. 4, pp. 1419-1440.
Neverova, I., et al., "Role of chromatographic techniques in proteomic analysis," *Journal of Chromatography B: Biomedical Sciences& Applications*, 2005, vol. 815(1-2), pp. 51-63.
Nony, E., et al., "Comprehensive allergen quantitation using mass spectrometry," *Allergy*, 2011, vol. 66(Suppl. 94), p. 524, Abstract No. 1381.
Patton, W., et al., "Two-dimensional gel electrophoresis; better than a poke in the ICAT?" *Current Opinion in Biotechnology*, 2002, vol. 13(4), pp. 321-328.
Petersen, A., et al., "Epitope Analysis of Isoforms of the Major allergen PhI p V by Fingerprinting and Microsequencing," *Clin Exp. Allergy*, 1994, vol. 24(3), pp. 250-256.
Piboonpocanun, S., et al., "Genetic Polymorphisms of major house dust mite allergens," *Clinical and Experimental Allergy*, 2006, vol. 36, pp. 510-516.
Preliminary Opinion of the Opposition Division, Nov. 17, 2011, issued in opposition proceeding to counterpart EP application 06775965.4 (EP 1931998), 5 pages.
Raftery, M., et al., "Mass spectrometric analysis of electrophoretically separated allergens and proteases in grass pollen diffusates," *Respiratory Research*, 2003, vol. 4, No. 10, pp. 1-12.
Rappsilber, J., et al., "What does it mean to identify a protein in proteomics," *TRENDS in Biochemical Sciences*, 2002, vol. 27, No. 2, pp. 74-78.
Schenk, M., et al., "Seven different genes encode a diverse mixture of isoforms of Bet v 1, the major birch pollen allergen," *BMC Genomics*, 2006, vol. 7, No. 168, pp. 1-15.
Schmidt, A., et al., "A Novel Strategy for Quantitative Proteomics Using Isotope-coded Protein Labels," *Proteomics*, 2002, vol. 5, pp. 4-15.
Seppala, U., et al., "Analysis of N-Glycosylation in Vespula Bulgaris Hyaluronidase Ves v 2," *Journal of Allergy and Clinical Immunology*, 2006, vol. 117(2), p. 119.
Seppala, U., et al., Absolute Quantification of Allergens from Complex Mixtures: A New Sensitive Tool for Standardization of Allergen Extracts for Specific Immunotherapy, *Journal of Proteome Research*, 2011, vol. 10, pp. 2113-2122, Epub Feb. 17, 2011.
Sequences Uniprot, Accession Q5TIW2, submitted Dec. 21, 2004.
Sequences Uniprot, Accession P43213, submitted Nov. 1, 1995.
Sequences Uniport, Accession Q39425, submitted Nov. 1, 1996.
Sequences Uniprot, Accession Q39426, submitted Nov. 1, 1996.
Shefcheck, K., et al., "Confirmation of the Allergenic Peanut Protein, Ara h 1, in a Model Food Matrix Using Liquid Chromatography/tandem mass Spectrometry (LC/MS/MS)," *J. Agric Food. Chem.*, 2004, vol. 52, pp. 2785-2790.
Smith, W., et al., "Allergens of wild house dust mites: Environmental Der p 1 and Der p 2 sequence polymorphisms," *J. Allergy Clin. Immunol.*, 2001, vol. 107, pp. 985-992.
Stemman, O., et al., "Dual Inhibition of Sister Chromatid Separation at Metaphase," *Cell*, 2001, vol. 107(6), pp. 715-726.
Swoboda, I., et al., "Isoforms of Bet v 1, the Major Birch Pollen Allergen, Analyzed by Liquid Chromatography, Mass Spectrometry, and cDNA Cloning," *The Journal of Biological Chemistry*, 1995, vol. 270(6), pp. 2607-2613.
Van Ree, Ronald, "Value of monoclonal antibody-based assays: advantages and drawbacks," Arbeiten Aus Dem Paul-Ehrlich-Institut (Bundesamt Fur Sera Und Impfstoffe) Zu Frankfurt A.M. 1994 LNKD—Pubmed: 7873051, No. 87, 1994, pp. 127-139.
Van Ree, R., et al., "Analytic aspects of the standardization of allergenic extracts," *Allergy*, 1997, vol. 52, pp. 795-805.
Van Ree., R., et al., "Isoallergens: A clinically, relevant phenomenon or just a product of cloning?" *Clinical and Experimental Allergy*, 2002, vol. 32(7), pp. 975-978.
Glinski, M., et al., "Differential Multisite Phosphorylation of the Trehalose-6-phosphate Synthase Gene Family in *Arabidopsis thaliana*," *Molecular& Cellular Proteonomics*, 2005, vol. 4(10), pp. 1614-1625.
Helmke, S., et al., "Simultaneous Quantification of Human Cardiac α- and β-Myosin Heavy Chain Proteins by MALDI-TOF Mass Spectrometry," *Anal. Chem.*, 2004, vol. 76, pp. 1683-1689.
Briza, Peter, "Affidavit of Professor Dr. Peter Briza," 2017, 4 pages.

(56) References Cited

OTHER PUBLICATIONS

Hunter, C. et al., Using Stable Isotope Tags and a Hybrid Quadrupole-Linear Ion Trap Mass Spectrometer for Quantifying Proteins, Poster No. M-434, Applied Biosystems, MDS Sciex, , 2004, 4 pages.

Ong, S., et anon., "Mass spectrometry-based proteomics turns quantitative," *Nature Chemical Biology*, 2005, vol. 1(5), pp. 252-262.

\* cited by examiner

Figure 1a              1                                                                                   60

```
Der p 2 1A9V             ------------------SQVDVKDC----------------------ANHEIK
Der p 2 1KTJ_B           ------------------SEVDVKDC----------------------ANHEIK
Der p 2 AAF86462         -MYKIHCLSLLVAAVARDQVDVKDC----------------------ANHEIK
Der p 2 P49278           MMYKIHCLSLLVAAVARDQVDVKDC----------------------ANHEIK
Lep d 2 2118249A         -MMKFHALFALVAVASAGKMTFKDCG---------------------HGEVT
Lep d 2 CAA57160         ------------------------------------------------------
Lep d 2 CAA61419         -MMKFHALFALVAVASAGKMTFKDCG---------------------HGEVT
Lep d 2 CAD32313         -MMKFHALFALVAVASAGKMTFKDCG---------------------HGEVT
Lep d 2 2118249B         -MMKFHALFALVAVASAGKMTFKDCG---------------------HGEVT
Lep d 2 CAA58755         -MMKFHALFALVAVASAGKMTFKDCG---------------------HGEVT
Lep d 2 CAD32314         -MMKFHALFALVAVASAGKMTFKDCG---------------------HGEVT
Lep d 2 CAB76459         --------------GKMKFKDCG------------------------KGEVT
Lep d 2 CAB59976         --------------GKMNFTDCG------------------------HNEIK
Pso o 2 AAK61827         MMKTLVVLAITHAVVSAGKVKFQDCG---------------------KGEVE
Tyr p 2 CAA73221         --MKFHILFALVAVAAGQVKFTDCG----------------------KKEIA
Eur m 2 AAC82349         -MYKIHCLSLLVAAVAADQVDEKDC----------------------ANHEIK
Eur m 2 AAC82350         -------------VAAVAADQVDVKDC---------------------ANHEIK
Der f 2 CAI05848         MISKIHCLSLLVAAVVADQVDVKDC----------------------ANHEIK
Der f 2 CAI05850         MISKIHCLSLLVAAVVADQVDVKDC----------------------ANNEIK
Der f 2 CAI05849         MISKIHCLSLLVAAVVADQVDVKDC----------------------ANNEIK
Der f 2 1WRF_A           ---------------DQVDVKDC------------------------ANNEIK
Der f 2 AAB30829         ----GTMVSLLVAAVVADQVDVKDC----------------------ANNEIK
Der f 2 A61241           --------SLLVAAVVADQVDVKDC----------------------ANNEIK
Der f 2 JU0394           ---------------DQVDVKDC------------------------ANNEIK
Der f 2 Q00855           MISKIHCLSLLVAAVVADQVDVKDC----------------------ANNEIK
Der f 2 BAD74060         MISKIHCLSLLVAAVVADQVDVKDC----------------------ANNEIK
Der f 2 B61241           --------SLLVAAVVADQVDVKDC----------------------ANNEIK
Der f 2 1XWV_B           ---------------DQVDVKDC------------------------ANNEIK
Der f 2 A61501           ---------------DQVDVKDC------------------------ANNEIK
Der f 2 AAL47677         ---------------DQVDVKDC------------------------ANNEIK
```

61                                                                                  120

```
Der p 2 1A9V             KVLVPGCHGSEPCIIHRGKPFQLEAVFEANQNTKTAKIEIKASIDG-LEVDVPGIDPNAC
Der p 2 1KTJ_B           KVLVPGCHGSEPCIIHRGKPFQLEAVFEANQNTKTAKIEIKASIDG-LEVDVPGIDPNAC
Der p 2 AAF86462         KVLVPGCHGSEPCIIHRGKPFQLEAVFEANQNTKTAKIEIKASIDG-LEVDVPGIDPNAC
Der p 2 P49278           KVLVPGCHGSEPCIIHRGKPFQLEAVFEANQNTKTAKIEIKASIDG-LEVDVPGIDPNAC
Lep d 2 2118249A         EHDITGCSG-DTCVIHRGEKMTLEAKFAANQDTAKVTIKVLAKVAG-TTIQVPGLETDGC
Lep d 2 CAA57160         --------------IHRGEKMTLEAKFAANQDTAKVTIKVLAKVAG-TTIQVPGLETDGC
Lep d 2 CAA61419         EHDITGCSG-DTCVIHRGEKMTLEAKFAANQDTAKVTIKVLAKVAG-TTIQVPGLETDGC
Lep d 2 CAD32313         EHDITGCSG-DTCVIHRGEKMTLEAKFAANQDTAKVTIKVLTKVAG-TTIQVPGLETDGC
Lep d 2 2118249B         EHDISGCSG-DTCVIHRGQKMTLDAKFAANQDTNKVTIKVLAKVAG-TTIQVPGLETDGC
Lep d 2 CAA58755         EHDISGCSG-DTCVIHRGQKMTLDAKFAANQDTNKVTIKVLAKVAG-TTIQVPGLETDGC
Lep d 2 CAD32314         EHDISGCSG-DTCVIHRGQKMTLDAKFAANQDTNKVTIKVLAKVAG-TTIQVPGLETDGC
Lep d 2 CAB76459         EHDITDCSG-DFCVIHRGKPLTLEAKFAANQDTTKATIKVLAKVAG-TPIQVPGLETDGC
Lep d 2 CAB59976         EHSVSNCTG-NYCVIHRGKPLTLDAKFDANQDTASVGLVETAIDGDTAIDIPGLETNAC
Pso o 2 AAK61827         SLEVEGCSG-DYCVIHKGKKLDLAISVTSNQDSANLKIDIVADING-VQIEVPGVDHDGC
Tyr p 2 CAA73221         SVAVEGCEG-DLCVIHKSKPVHVIAEFTANQDTCKIEVKVTGQLNG-LEVPIPGIETDGC
Eur m 2 AAC82349         KVMVPGCKGSEPCVIHRGTAFQLEAVFDANQNSNAAKIEIKATIDG-VEIDVPGIDNNLC
```

```
Eur m 2  AAC82350    KVMVPGCKGSEPCVIHRGTAFQLEAVFDANQNSNAAKIEIKATIDG-VEIDVPGIDNNLC
Der f 2  CAI05848    KVMVDGCHGSDPCIIHRGKPFNLEATFDANQNTKTAKIEIKANIDG-LEVDVPGIDTNAC
Der f 2  CAI05850    KVMVDGCHGSDPCIIHRGKPFTLEAIFDANQNTKTAKIEIKANING-LEVDVPGIDTNAC
Der f 2  CAI05849    KVMVDGCHGSDPCIIHRGKPFTLEAIFDANQNTKTAKIEIKANING-LEVDVPGIDTNAC
Der f 2  1WRF_A      KVMVDGCHGSDPCIIHRGKPFTLEAIFDANQNTKTAKIEIKASLDG-LEIDVPGIDTNAC
Der f 2  AAB30829    KVMVDGCHGSDPCIIHRGKPFTLEAIFDANQNTKTAKIEIKASLDG-LEIDVPGIDTNAC
Der f 2  A61241      KVMVDGCHGSDPCIIHRGKPFTLEAIFDANQNTKTAKIEIKASLDG-LEIDVPGIDTNAC
Der f 2  JU0394      KVMVDGCHGSDPCIIHRGKPFTLEAIFDANQNTKTAKIEIKASLDG-LEIDVPGIDTNAC
Der f 2  Q00855      KVMVDGCHGSDPCIIHRGKPFTLEAIFDANQNTKTAKIEIKASLDG-LEIDVPGIDTNAC
Der f 2  BAD74060    KVMVDGCHGSDPCIIHRGKPFTLEAIFDANQNTKTAKIEIKASLDG-LEIDVPGIDTNAC
Der f 2  B61241      KVMVDGCHGSDPCIIHRGKPFTLEAIFDANQNTKTAKIEIKASLDG-LEIDVPGIDTNAC
Der f 2  1XWV_B      KVMVDGCHGSDPCIIHRGKPFTLEAIFDANQNTKTAKIEIKASLDG-LEIDVPGIDTNAC
Der f 2  A61501      KVMVDGCHGSDPCIIHRGKPFTLEAIFDANQNTKTAKTEIKASIDG-LEIDVPGIDTNAC
Der f 2  AAL47677    KVMVDGCHGSDPCIIHRGKPFTLEAIFDANQNTKTAKIEIKASLDG-LEIDVPGIDTNAC
```

121                                                   176

```
Der p 2  1A9V        HYMKCPLVKGQQYDIKYTWNVPKIAPKSENVVVTVKVMGDDGVLACAIATHAKIRD
Der p 2  1KTJ_B      HYMKCPLVKGQQYDIKYTWNVPKIAPKSENVVVTVKVMGDDGVLACAIATHAKIRD
Der p 2  AAF86462    HYMKCPLVKGQQYDIKYTWNVPKIAPKSENVVVTVKVMGDDGVLACAIATHAKIRD
Der p 2  P49278     HYMKCPLVKGQQYDIKYTWNVPKIAPKSENVVVTVKVMGDDGVLACAIATHAKIRD
Lep d 2  2118249A    KFIKCPVKKGEALDFIYSG-TIPAITPKVKADVTAELIGDHGVMACGTVHGVQE--
Lep d 2  CAA57160    KFIKCPVKKGEALDFIYSG-TIPAITPKVKADVTAELIGDHGVMACGTVHGQVE--
Lep d 2  CAA61419    KFIKCPVKKGEALDFIYSG-TIPAITPKVKADVTAELIGDHGVMACGTVHGQVE--
Lep d 2  CAD32313    KFIKCPVKKGEALDFIYSG-TIPAITPKVKADVTAELIGDHGVMACGTVHGQVE--
Lep d 2  2118249B    KVLKCPIKKGEALDFNYGM-TIPAITPKIKADVTAELVGDHGVMACGTIHGQVE--
Lep d 2  CAA58755    KVLKCPIKKGEALDFNYGM-TIPAITPKIKADVTAELVGDHGVMACGTIHGQVE--
Lep d 2  CAD32314    KVLKCPIKKGEALDFNYGM-TIPAITPKIKVDVTAELVGDHGVMACGTIHGQVE--
Lep d 2  CAB76459    KFVKCPIKKGDPIDFKYTT-TVPAILPKVKAEVTAELVGDHGVLACGRFGRQVE--
Lep d 2  CAB59976    KLMKCPIRKGEHQEIIKNIGEIPDATPEIKAKVKAQLIGEHGVLACGWVDGEVQE-
Pso o 2  AAK61827    HYVKCPIKKGQHEDVKYTY-SIPAILPITKAKIIAKTIGDKGLGGGIVINGEIQD-
Tyr p 2  CAA73221    KVLKCPLKKGTKYTMNYSV-NVPSVVPNIKTVVKDLATGEHGVLACGAVNTDVKP-
Eur m 2  AAC82349    HFMKCPLVKGQEYDIKYTWNVPRIAPKSENVVVTVKLIGDNGVLACAIATHAKIRD
Eur m 2  AAC82350    HFMKCPLVKGQEYDIKYTWNVPRIAPKSENVVVTVKLLGDNGVLACAIATHAKIRD
Der f 2  CAI05848    HYIKCPLVKGQQYDAKYTWNVPKIAPKSENVVVTVKLVGDNGVLACAIATHAKIRD
Der f 2  CAI05850    HYIKCPLVKGQQYDAKYTWNVPKIAPKSENVVVTVKLVGDNGVLACAIATHAKIRD
Der f 2  CAI05849    HYIKCPLVKGQQYDAKYTWNVPKIAPKSENVVVTVKLVGDNGVLACAIATHAKIRD
Der f 2  1WRF_A      HFVKCPLVKGQQYDIKYTWNVPKIAPKSENVVVTVKLIGDNGVLACAIATHGKIRD
Der f 2  AAB30829    HFVKCPLVKGQQYDIKYTWNVPKIAPKSENVVVTVKLIGDNGVLACAIATHGKIRD
Der f 2  A61241      HFVKCPLVKGQQYDIKYTWNVPKIAPKSENVVVTVKLIGDNGVLACAIATHGKIRD
Der f 2  JU0394      HFMKCPLVKGQQYDIKYTWNVPKIAPKSENVVVTVKLIGDNGVLACAIATHGKIRD
Der f 2  Q00855      HFMKCPLVKGQQYDIKYTWNVPKIAPKSENVVVTVKLIGDNGVLACAIATHGKIRD
Der f 2  BAD74060    HFMKCPLVKGQQYDIKYTWDVPKIAPKSENVVVTVKLVGDNGVLACAIATHGKIRD
Der f 2  B61241      HFMKCPLVKGQQYDAKYTWNVPKIAPKSENVVVTVKLVGDNGVLACAIATHAKIRD
Der f 2  1XWV_B      HFMKCPLVKGQQYDAKYTWNVPKIAPKSENVVVTVKLVGDNGVLACAIATHAKIRD
Der f 2  A61501      HFMKCPLVKGQQYDAKYTWNVPKIAPKSENVVVTVKLVGDNGVLACAIATHAKIRD
Der f 2  AAL47677    HFMKCPLVKGQQYDAKYTWNVPKIAPESENVVVTVKLVGDNGVLACAIATHAKIRD
```

Figure 1a (contd.)

Figure 1b

```
                       1                                                          60
Bet v 1 P15494  (1)  MGVFNYETETTSVIPAARLFKAFILDGDNLFPKVAPQAISSVENIEGNGGPGTIKKISFE
Bet v 1 P43177  (1)  MGVFNYEIETTSVIPAARLFKAFIIDGDNLVPKVAPQAISSVENIEGNGGPGTIKKINFE
Bet v 1 P43180  (1)  MGVFNYESETTSVIPAARLFKAFILEGDNLIPKVAPQAISSVENIEGNGGPGTIKKINFE
Bet v 1 P43185  (1)  MGVFNYETEATSVIPAARMFKAFILDGDKLVPKVAPQAISSVENIEGNGGPGTIKKINFE
Bet v 1 P43176  (1)  MGVFNYESETTSVIPAARLFKAFILEGDTLIPKVAPQAISSVENIEGNGGPGTIKKITFE
Bet v 1 P43184  (1)  MGVFNYESETTSVIPAARLFKAFILEGDTLIPKVAPQAISSVENIEGNGGPGTIKKITFE
Bet v 1 P45431  (1)  MGVFNYETETTSVIPAARLFKAFILEGDTLIPKVAPQAISSVENIEGNGGPGTIKKITFE
Bet v 1 P43186  (1)  MGVFNYESETTSVIPAARLFKAFILDGDNLIPKVAPQAISSVENIEGNGGPGTIKKITFE
Bet v 1 P43178  (1)  MGVFNYETEATSVIPAARLFKAFILDGDNLFPKVAPQAISSVENIEGNGGPGTIKKISFE
Bet v 1 P43179  (1)  MGVFNYEIEATSVIPAARLFKAFILDGDNLFPKVAPQAISSVENIEGNGGPGTIKKISFE
Bet v 1 P43183  (1)  MGVFNYETEATSVIPAARLFKAFILDGDNLFPKVAPQAISSVENIEGNGGPGTIKKISFE 61                                                        120
Bet v 1 P15494 (61)  EGFPFKYVKDRVDEVDHTNFKYNYSVIEGGPIGDTLEKISNEIKIVATPDGGSILKISNK
Bet v 1 P43177 (61)  EGFPFKYVKDRVDEVDHTNFKYNYSVIEGGPVGDTLEKISNEIKIVATPDGGCVLKISNK
Bet v 1 P43180 (61)  EGFPFKYVKDRVDEVDHTNFKYNYSVIEGGPVGDTLEKISNEIKIVATPDGGCVLKISNK
Bet v 1 P43185 (61)  EGFPFKYVKDRVDEVDHTNFKYNYSVIEGGPVGDTLEKISNEIKIVATPDGGCVLKISNK
Bet v 1 P43176 (61)  EGSPFKYVKERVDEVDHANFKYSYSMIEGGALGDTLEKICNEIKIVATPDGGSILKISNK
Bet v 1 P43184 (61)  EGSPFKYVKERVDEVDHANFKYSYSMIEGGALGDTLEKICNEIKIVATPDGGSILKISNK
Bet v 1 P45431 (61)  EGSPFKYVKERVDEVDHANFKYSYSMIEGGALGDTLEKICNEIKIVATPDGGSILKISNK
Bet v 1 P43186 (61)  EGSPFKYVKERVDEVDHANFKYSYSMIEGGALGDTLEKICNEIKIVATPDGGSILKISNK
Bet v 1 P43178 (61)  EGIPFKYVKGRVDEVDHTNFKYSYSVIEGGPVGDTLEKISNEIKIVATPNGGSILKINNK
Bet v 1 P43179 (61)  EGFPFKYVKDRVDEVDHTNFKYSYSVIEGGPVGDTLEKISNEIKIVATPNGGSILKINNK
Bet v 1 P43183 (61)  EGFPFKYVKDRVDEVDHTNFKYSYSVIEGGPVGDTLEKISNEIKIVATPNGGSILKINNK 121                                  160
Bet v 1 P15494 (121) YHTKGDHEVKAEQVKASKEMGETLLRAVESYLLAHSDAYN
Bet v 1 P43177 (121) YHTKGNHEVKAEQVKASKEMGETLLRAVESYLLAHSDAYN
Bet v 1 P43180 (121) YHTKGNHEVKAEQVKASKEMGETLLRAVESYLLAHSDAYN
Bet v 1 P43185 (121) YHTKGNHEVKAEQVKASKEMGETLLRAVESYLLAHSDAYN
Bet v 1 P43176 (121) YHTKGDQEMKAEHMKAIKEKGEALLRAVESYLLAHSDAYN
Bet v 1 P43184 (121) YHTKGDHEMKAEHMKAIKEKGEALLRAVESYLLAHSDAYN
Bet v 1 P45431 (121) YHTKGDHEMKAEHMKAIKEKGEALLRAVESYLLAHSDAYN
Bet v 1 P43186 (121) YHTKGDHEMKAEHMKAIKEKGEALLRAVESYLLAHSDAYN
Bet v 1 P43178 (121) YHTKGDHEVKAEQIKASKEMGETLLRAVESYLLAHSDAYN
Bet v 1 P43179 (121) YHTKGDHEVKAEQIKASKEMGETLLRAVESYLLAHSDAYN
Bet v 1 P43183 (121) YHTKGDHEVKAEQIKASKEMGETLLRAVESYLLAHSDAYN
```

Figure 2

Theoretical cleavage analyses of calibration standard peptides for quantification by MS a) Tryptic digestion of Der f 2 (A61501)

| Peptide | From-To | MH+ | pI | Sequence |
|---|---|---|---|---|
| 1 | 1-6 | 703.36 | 3.92 | DQVDVK (SEQ ID NO: 1) |
| 2 | 7-14 | 905.39 | 4.11 | DCANNEIK (SEQ ID NO: 2) |
| 3 | 15-15 | 147.11 | 9.47 | K |
| 4 | 16-31 | 1736.77 | 6.00 | VMVDGCHGSDPCIIHR (SEQ ID NO: 3) |
| 5 | 32-48 | 1893.97 | 6.99 | GKPFTLEALFDANQNTK (SEQ ID NO: 4) |
| 6 | 49-51 | 319.20 | 9.80 | TAK |
| 7 | 52-55 | 490.29 | 6.97 | TEIK (SEQ ID NO: 5) |
| 8 | 56-77 | 2345.10 | 4.00 | ASLDGLEIDVPGIDTNACHFMK (SEQ ID NO: 6) |
| 9 | 78-82 | 558.32 | 9.30 | CPLVK (SEQ ID NO: 7) |
| 10 | 83-89 | 809.38 | 6.71 | GQQYDAK (SEQ ID NO: 8) |
| 11 | 90-96 | 907.47 | 9.49 | YTWNVPK (SEQ ID NO: 9) |
| 12 | 97-100 | 428.29 | 10.15 | IAPK (SEQ ID NO: 10) |
| 13 | 101-109 | 974.55 | 6.97 | SENVVVTVK (SEQ ID NO: 11) |
| 14 | 110-126 | 1651.87 | 7.14 | LVGDNGVLACAIATHAK (SEQ ID NO: 12) |
| 15 | 127-128 | 288.20 | 11.15 | IR |
| 16 | 129-129 | 134.04 | 2.98 | D | b) Tryptic digestion of Der p 2 (BAA01241)

| Peptide | From-To | MH+ | pI | Sequence |
|---|---|---|---|---|
| 1 | 1-6 | 703.36 | 3.92 | DQVDVK (SEQ ID NO: 13) |
| 2 | 7-14 | 928.41 | 5.24 | DCANHEIK (SEQ ID NO: 14) |
| 3 | 15-15 | 147.11 | 9.47 | K |
| 4 | 6-31 | 1714.85 | 7.15 | VLVPGCHGSEPCIIHR (SEQ ID NO: 15) |
| 5 | 32-48 | 1920.98 | 7.00 | GKPFQLEAVFEANQNTK (SEQ ID NO: 16) |
| 6 | 49-51 | 319.20 | 9.80 | TAK |
| 7 | 52-55 | 502.32 | 6.99 | IEIK (SEQ ID NO: 17) |
| 8 | 56-77 | 2343.09 | 4.00 | ASIDGLEVDVPGIDPNACHYMK (SEQ ID NO: 18) |
| 9 | 78-82 | 558.32 | 9.30 | CPLVK (SEQ ID NO: 19) |
| 10 | 83-89 | 851.43 | 6.71 | GQQYDIK (SEQ ID NO: 20) |
| 11 | 90-96 | 907.47 | 9.49 | YTWNVPK (SEQ ID NO: 21) |
| 12 | 97-100 | 428.29 | 10.15 | IAPK (SEQ ID NO: 22) |
| 13 | 101-109 | 974.55 | 6.97 | SENVVVTVK (SEQ ID NO: 23) |
| 14 | 110-126 | 1670.81 | 5.12 | VMGDDGVLACAIATHAK (SEQ ID NO: 24) |
| 15 | 127-128 | 288.20 | 11.15 | IR |
| 16 | 129-129 | 134.04 | 2.98 | D | c) Tryptic digestion of Phl p 1 Q40967

| Peptide | From-To | MH+ | pI | Sequence |
|---|---|---|---|---|
| 1 | 1-26 | 2601.44 | 9.90 | MASSSSVLLVVALFAVFLGSAHGIPK (SEQ ID NO: 25) |
| 2 | 27-40 | 1429.73 | 6.68 | VPPGPNITATYGDK (SEQ ID NO: 26) |
| 3 | 41-45 | 632.34 | 6.98 | WLDAK (SEQ ID NO: 27) |
| 4 | 46-58 | 1363.70 | 10.12 | STWYGKPTAAGPK (SEQ ID NO: 28) |
| 5 | 59-67 | 884.35 | 6.09 | DNGGACGYK (SEQ ID NO: 29) |
| 6 | 68-87 | 2110.99 | 6.24 | DVDKPPFSGMTGCGNTPIFK (SEQ ID NO: 30) |
| 7 | 88-90 | 319.17 | 10.85 | SGR |
| 8 | 91-99 | 943.40 | 6.15 | GCGSCFEIK (SEQ ID NO: 31) |
| 9 | 100-140 | 4349.01 | 4.25 | CTKPEACSGEPVVVHITDDNEEPIAAYHFDLSGIAFGSMAK (SEQ ID NO: 32) |
| 10 | 141-141 | 147.11 | 9.47 | K |
| 11 | 142-146 | 576.26 | 4.11 | GDEQK (SEQ ID NO: 33) |
| 12 | 147-148 | 288.20 | 11.10 | LR |

| 13 | 149-158 | 1135.57 | 4.31 | SAGEVEIQFR (SEQ ID NO: 34) |
| 14 | 159-159 | 175.11 | 10.76 | R |
| 15 | 160-161 | 246.18 | 10.10 | VK |
| 16 | 162-163 | 250.12 | 9.30 | CK |
| 17 | 164-169 | 694.34 | 6.67 | YPEGTK (SEQ ID NO: 35) |
| 18 | 170-176 | 859.46 | 7.82 | VTFHVEK (SEQ ID NO: 36) |
| 19 | 177-188 | 1288.72 | 9.80 | GSNPNYLALLVK (SEQ ID NO: 37) |
| 20 | 189-202 | 1404.73 | 2.78 | FVAGDGDVVAVDIK (SEQ ID NO: 38) |
| 21 | 203-204 | 276.15 | 6.99 | EK |
| 22 | 205-206 | 204.13 | 10.15 | GK |
| 23 | 207-208 | 262.13 | 6.99 | DK |
| 24 | 209-213 | 630.39 | 9.95 | WIALK (SEQ ID NO: 39) |
| 25 | 214-221 | 1004.49 | 7.04 | ESWGAIWR (SEQ ID NO: 40) |
| 26 | 222-229 | 914.51 | 4.11 | IDTPEVLK (SEQ ID NO: 41) |
| 27 | 230-235 | 676.37 | 11.15 | GPFTVR (SEQ ID NO: 42) |
| 28 | 236-243 | 856.40 | 6.67 | YTTEGGTK (SEQ ID NO: 43) |
| 29 | 244-247 | 404.21 | 6.99 | GEAK (SEQ ID NO: 44) |
| 30 | 248-255 | 943.48 | 4.11 | DVIPEGWK (SEQ ID NO: 45) |
| 31 | 256-263 | 884.39 | 4.11 | ADTAYESK (SEQ ID NO: 46) | d) Tryptic digestion of Phl p 5a Q40962

| Peptide | From-To | MH+ | pI | Sequence |
| --- | --- | --- | --- | --- |
| 1 | 1-33 | 2910.42 | 3.92 | ADLGYGPATPAAPAAGYTPATPAAPAGADAAGK (SEQ ID NO: 47) |
| 2 | 34-40 | 806.38 | 4.31 | ATTEEQK (SEQ ID NO: 48) |
| 3 | 41-44 | 502.32 | 6.99 | LIEK (SEQ ID NO: 49) |
| 4 | 45-50 | 649.36 | 10.15 | INAGFK (SEQ ID NO: 50) |
| 5 | 51-63 | 1168.63 | 6.99 | AALAGAGVQPADK (SEQ ID NO: 51) |
| 6 | 64-65 | 338.18 | 9.60 | YR |
| 7 | 66-77 | 1239.63 | 9.80 | TFVATFGPASNK (SEQ ID NO: 52) |
| 8 | 78-88 | 1105.55 | 4.31 | AFAEGLSGEPK (SEQ ID NO: 53) |
| 9 | 89-96 | 736.34 | 6.99 | GAAESSSK (SEQ ID NO: 54) |
| 10 | 97-102 | 590.35 | 10.20 | AALTSK (SEQ ID NO: 55) |
| 11 | 103-108 | 680.36 | 6.68 | LDAAYK (SEQ ID NO: 56) |
| 12 | 109-112 | 494.29 | 9.76 | LAYK (SEQ ID NO: 57) |
| 13 | 113-122 | 974.47 | 4.31 | TAEGATPEAK (SEQ ID NO: 58) |
| 14 | 123-135 | 1471.74 | 4.11 | YDAYVATLSEALR (SEQ ID NO: 59) |
| 15 | 136-154 | 1975.12 | 5.42 | IIAGTLEVHAVKPAAEEVK (SEQ ID NO: 60) |
| 16 | 155-166 | 1295.75 | 4.31 | VIPAGELQVIEK (SEQ ID NO: 61) |
| 17 | 167-172 | 650.35 | 6.98 | VDAAFK (SEQ ID NO: 62) |
| 18 | 173-186 | 1284.65 | 6.98 | VAATAANAAPANDK (SEQ ID NO: 63) |
| 19 | 187-199 | 1530.74 | 3.87 | FTVFEAAFNDEIK (SEQ ID NO: 64) |
| 20 | 200-210 | 1133.51 | 6.90 | ASTGGAYESYK (SEQ ID NO: 65) |
| 21 | 211-220 | 1058.62 | 6.97 | FIPALEAAVK (SEQ ID NO: 66) |
| 22 | 221-234 | 1419.74 | 6.67 | QAYAATVATAPEVK (SEQ ID NO: 67) |
| 23 | 235-243 | 1071.57 | 6.67 | YTVFETALK (SEQ ID NO: 68) |
| 24 | 244-244 | 147.11 | 9.47 | K |
| 25 | 245-254 | 1049.52 | 6.99 | AITAMSEAQK (SEQ ID NO: 69) |
| 26 | 255-285 | 2605.35 | 10.25 | AKPAAAATATATAAVGAATAATGGYK |
| 27 | 286-286 | 118.08 | 6.00 | V (SEQ ID NO: 70) | e) Tryptic digestion of Phl p 5b Q40963

| Peptide | From-To | MH+ | pI | Sequence |
| --- | --- | --- | --- | --- |
| 1 | 1-7 | 655.38 | 11.20 | AAAAVPR (SEQ ID NO: 71) |
| 2 | 8-8 | 175.11 | 10.76 | R |
| 3 | 9-11 | 329.19 | 11.15 | GPR |
| 4 | 12-16 | 443.23 | 11.15 | GGPGR (SEQ ID NO: 72) |

Figure 2 (contd.)

| | | | | |
|---|---|---|---|---|
| 5 | 17-38 | 1952.93 | 6.49 | SYTADAGYAPATPAAAGAAAGK (SEQ ID NO: 73) |
| 6 | 39-45 | 806.38 | 4.31 | ATTEEQK (SEQ ID NO: 74) |
| 7 | 46-55 | 1147.63 | 4.11 | LIEDINVGFK (SEQ ID NO: 75) |
| 8 | 56-69 | 1212.65 | 6.99 | AAVAAAASVPAADK (SEQ ID NO: 76) |
| 9 | 70-71 | 294.18 | 9.85 | FK |
| 10 | 72-82 | 1175.55 | 6.97 | TFEAAFTSSSK (SEQ ID NO: 77) |
| 11 | 83-87 | 431.26 | 10.20 | AAAAK (SEQ ID NO: 78) |
| 12 | 88-94 | 681.42 | 10.20 | APGLVPK (SEQ ID NO: 79) |
| 13 | 95-104 | 1100.56 | 6.66 | LDAAYSVAYK (SEQ ID NO: 80) |
| 14 | 105-114 | 914.49 | 6.99 | AAVGATPEAK (SEQ ID NO: 81) |
| 15 | 115-127 | 1455.74 | 4.11 | FDSFVASLTEALR (SEQ ID NO: 82) |
| 16 | 128-149 | 2246.22 | 5.42 | VIAGALEVHAVKPVTEEPGMAK (SEQ ID NO: 83) |
| 17 | 150-160 | 1196.68 | 4.11 | IPAGELQIIDK (SEQ ID NO: 84) |
| 18 | 161-166 | 664.36 | 6.99 | IDAAFK (SEQ ID NO: 85) |
| 19 | 167-180 | 1272.64 | 3.92 | VAATAAATAPADDK (SEQ ID NO: 86) |
| 20 | 181-190 | 1173.59 | 6.97 | FTVFEAAFNK (SEQ ID NO: 87) |
| 21 | 191-193 | 331.23 | 10.20 | AIK |
| 22 | 194-204 | 1191.51 | 4.11 | ESTGGAYDTYK (SEQ ID NO: 88) |
| 23 | 205-214 | 1030.56 | 6.30 | CIPSLEAAVK (SEQ ID NO: 89) |
| 24 | 215-228 | 1388.75 | 9.49 | QAYAATVAAAPQVK (SEQ ID NO: 90) |
| 25 | 229-238 | 1112.59 | 6.67 | YAVFEAALTK (SEQ ID NO: 91) |
| 26 | 239-248 | 1077.56 | 6.99 | AITAMSEVQK (SEQ ID NO: 92) |
| 27 | 249-283 | 2919.48 | 9.76 | VSQPATGAATVAAGAATTAA GAASGAATVAAGGYK (SEQ ID NO: 93) |
| 28 | 284-284 | 118.08 | 6.00 | V | f) Tryptic digestion of Bet v 1

| Peptide | From-To | MH+ | pI | Sequence |
|---|---|---|---|---|
| 1 | 1-18 | 1985.9637 | 4.31 | MGVFNYETETTSVIPAAR (SEQ ID NO: 94) |
| 2 | 19-21 | 407.2653 | 10.10 | LFK |
| 3 | 22-33 | 1349.7100 | 3.92 | AFILDGDNLFPK (SEQ ID NO: 95) |
| 4 | 34-57 | 2386.2249 | 4.31 | VAPQAISSVENIFTEGNGGPGTIK (SEQ ID NO: 96) |
| 5 | 58-58 | 147.1128 | 9.47 | K |
| 6 | 59-68 | 1134.6194 | 6.99 | ISFPEGLPFK (SEQ ID NO: 97) |
| 7 | 69-71 | 409.2445 | 9.49 | YVK |
| 8 | 72-73 | 290.1459 | 7.04 | DR |
| 9 | 74-83 | 1203.5640 | 4.34 | VDEVDHTNFK (SEQ ID NO: 98) |
| 10 | 84-100 | 1854.9120 | 3.87 | YNYSVIEGGPIGDTLEK (SEQ ID NO: 99) |
| 11 | 101-106 | 703.3985 | 6.99 | ISNEIK (SEQ ID NO: 100) |
| 12 | 107-120 | 1418.7890 | 6.97 | FTIVATPDGGSILK (SEQ ID NO: 101) |
| 13 | 121-124 | 461.2718 | 10.15 | ISNK (SEQ ID NO: 102) |
| 14 | 125-128 | 548.2827 | 9.49 | YHTK (SEQ ID NO: 103) |
| 15 | 129-134 | 684.3311 | 5.24 | GDHEVK (SEQ ID NO: 104) |
| 16 | 135-139 | 574.3195 | 6.99 | AEQVK (SEQ ID NO: 105) |
| 17 | 140-142 | 305.1819 | 10.20 | ASK |
| 18 | 143-150 | 948.4819 | 4.31 | EMGETLLR (SEQ ID NO: 106) |
| 19 | 151-164 | 1552.7278 | 4.10 | AVESYLLAHSDAYN (SEQ ID NO: 107) |

Figure 2 (contd.)

Figure 3
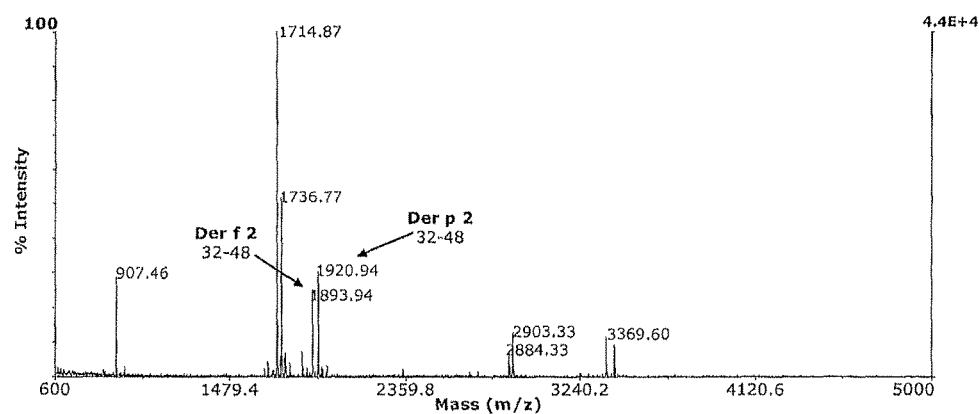
a)
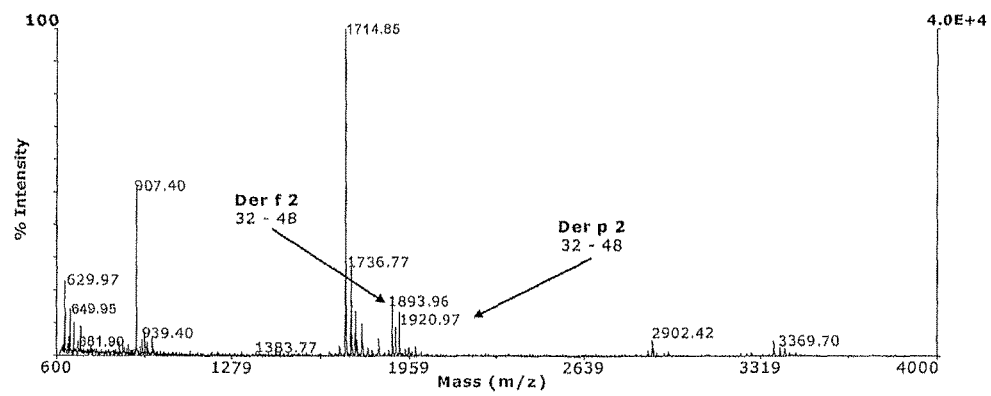
b)

Figure 6
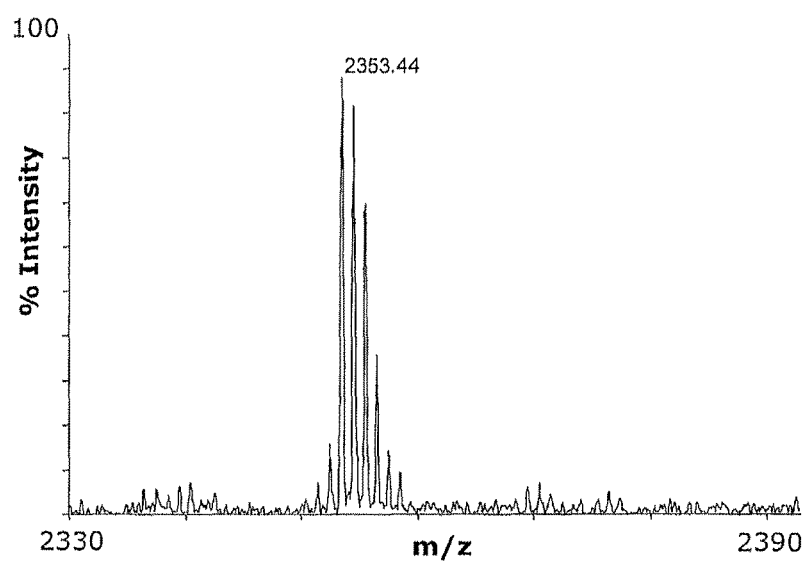
a)
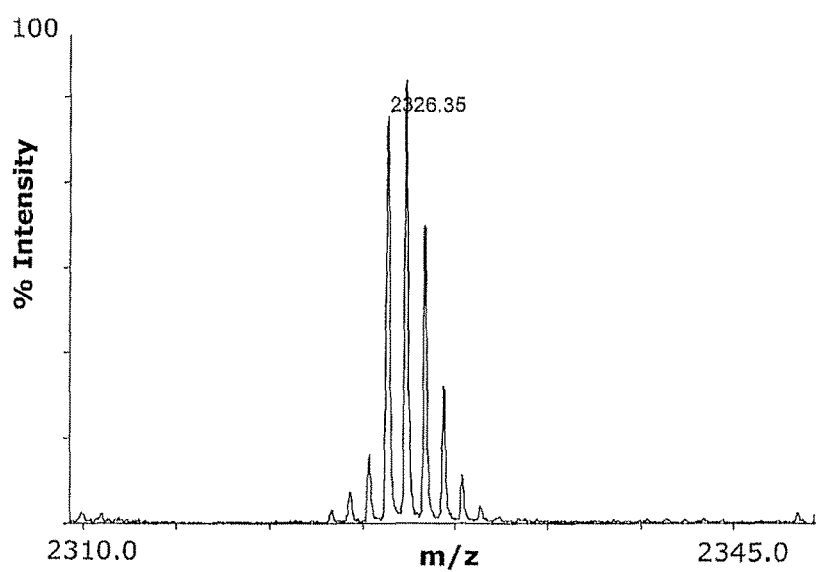
b)

Figure 6 (cont.)
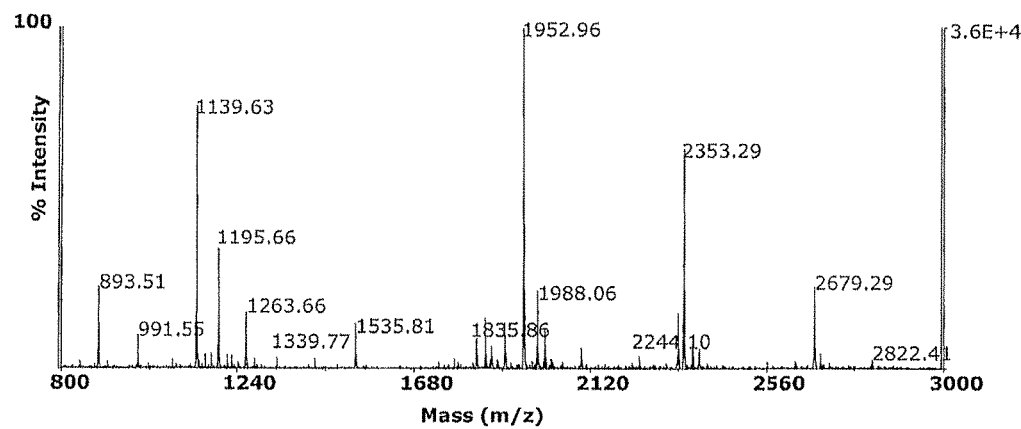
c)
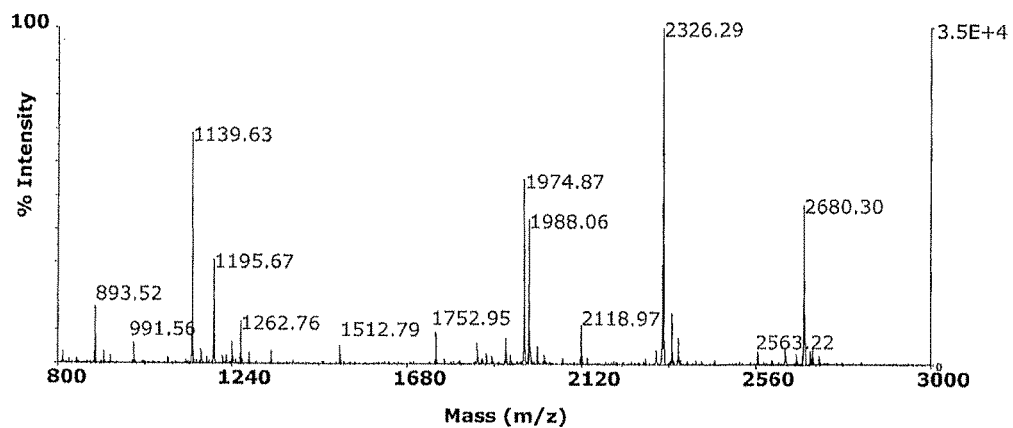
d)

Figure 7
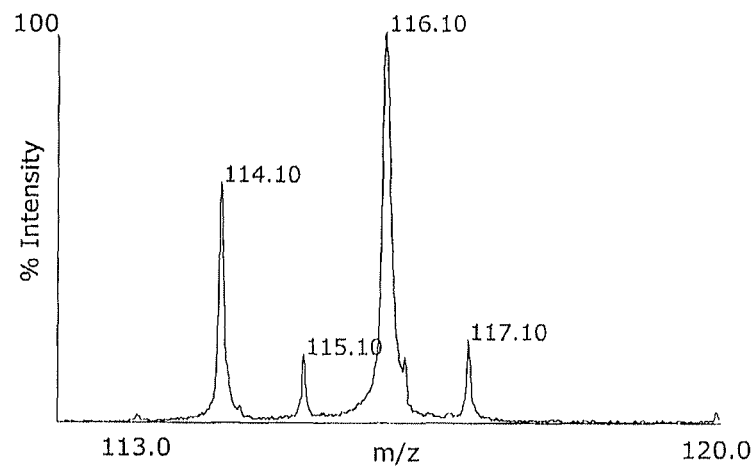
a)
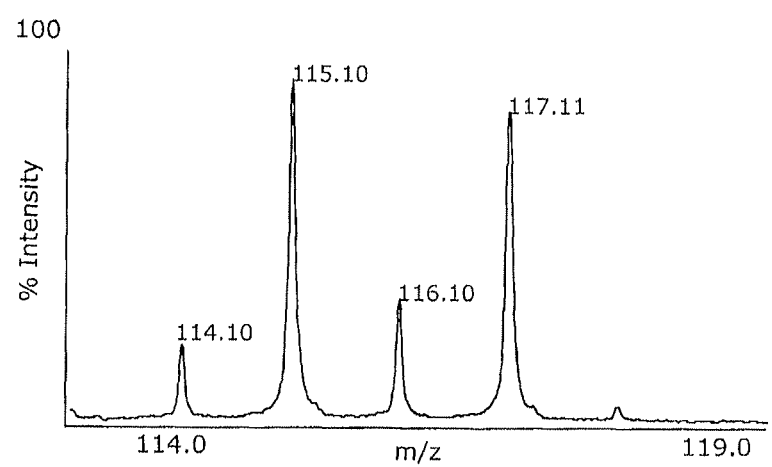
b)

SEQUENCE LISTING

```
<160> NUMBER OF SEQ ID NOS: 147

<210> SEQ ID NO 1
<211> LENGTH: 6
<212> TYPE: PRT
<213> ORGANISM: artificial
<220> FEATURE:
<223> OTHER INFORMATION: peptide digest fragment

<400> SEQUENCE: 1

Asp Gln Val Asp Val Lys
1               5

<210> SEQ ID NO 2
<211> LENGTH: 8
<212> TYPE: PRT
<213> ORGANISM: artificial
<220> FEATURE:
<223> OTHER INFORMATION: peptide digest fragment

<400> SEQUENCE: 2
```

Asp Cys Ala Asn Asn Glu Ile Lys
1               5

<210> SEQ ID NO 3
<211> LENGTH: 16
<212> TYPE: PRT
<213> ORGANISM: artificial
<220> FEATURE:
<223> OTHER INFORMATION: peptide digest fragment

<400> SEQUENCE: 3

Val Met Val Asp Gly Cys His Gly Ser Asp Pro Cys Ile Ile His Arg
1               5                   10                  15

<210> SEQ ID NO 4
<211> LENGTH: 17
<212> TYPE: PRT
<213> ORGANISM: artificial
<220> FEATURE:
<223> OTHER INFORMATION: peptide digest fragment

<400> SEQUENCE: 4

Gly Lys Pro Phe Thr Leu Glu Ala Leu Phe Asp Ala Asn Gln Asn Thr
1               5                   10                  15

Lys

<210> SEQ ID NO 5
<211> LENGTH: 4
<212> TYPE: PRT
<213> ORGANISM: artificial
<220> FEATURE:
<223> OTHER INFORMATION: peptide digest fragment

<400> SEQUENCE: 5

Thr Glu Ile Lys
1

<210> SEQ ID NO 6
<211> LENGTH: 22
<212> TYPE: PRT
<213> ORGANISM: artificial
<220> FEATURE:
<223> OTHER INFORMATION: peptide digest fragment

<400> SEQUENCE: 6

Ala Ser Leu Asp Gly Leu Glu Ile Asp Val Pro Gly Ile Asp Thr Asn
1               5                   10                  15

Ala Cys His Phe Met Lys
            20

<210> SEQ ID NO 7
<211> LENGTH: 5
<212> TYPE: PRT
<213> ORGANISM: artificial
<220> FEATURE:
<223> OTHER INFORMATION: peptide digest fragment

<400> SEQUENCE: 7

Cys Pro Leu Val Lys
1               5

<210> SEQ ID NO 8
<211> LENGTH: 7
<212> TYPE: PRT
<213> ORGANISM: artificial

```
<220> FEATURE:
<223> OTHER INFORMATION: peptide digest fragment

<400> SEQUENCE: 8

Gly Gln Gln Tyr Asp Ala Lys
1               5

<210> SEQ ID NO 9
<211> LENGTH: 7
<212> TYPE: PRT
<213> ORGANISM: artificial
<220> FEATURE:
<223> OTHER INFORMATION: peptide digest fragment

<400> SEQUENCE: 9

Tyr Thr Trp Asn Val Pro Lys
1               5

<210> SEQ ID NO 10
<211> LENGTH: 4
<212> TYPE: PRT
<213> ORGANISM: artificial
<220> FEATURE:
<223> OTHER INFORMATION: peptide digest fragment

<400> SEQUENCE: 10

Ile Ala Pro Lys
1

<210> SEQ ID NO 11
<211> LENGTH: 9
<212> TYPE: PRT
<213> ORGANISM: artificial
<220> FEATURE:
<223> OTHER INFORMATION: peptide digest fragment

<400> SEQUENCE: 11

Ser Glu Asn Val Val Val Thr Val Lys
1               5

<210> SEQ ID NO 12
<211> LENGTH: 17
<212> TYPE: PRT
<213> ORGANISM: artificial
<220> FEATURE:
<223> OTHER INFORMATION: peptide digest fragment

<400> SEQUENCE: 12

Leu Val Gly Asp Asn Gly Val Leu Ala Cys Ala Ile Ala Thr His Ala
1               5                   10                  15

Lys

<210> SEQ ID NO 13
<211> LENGTH: 6
<212> TYPE: PRT
<213> ORGANISM: artificial
<220> FEATURE:
<223> OTHER INFORMATION: peptide digest fragment

<400> SEQUENCE: 13

Asp Gln Val Asp Val Lys
1               5

<210> SEQ ID NO 14
<211> LENGTH: 8
<212> TYPE: PRT
```

```
<213> ORGANISM: artificial
<220> FEATURE:
<223> OTHER INFORMATION: peptide digest fragment

<400> SEQUENCE: 14

Asp Cys Ala Asn His Glu Ile Lys
1               5

<210> SEQ ID NO 15
<211> LENGTH: 16
<212> TYPE: PRT
<213> ORGANISM: artificial
<220> FEATURE:
<223> OTHER INFORMATION: peptide digest fragment

<400> SEQUENCE: 15

Val Leu Val Pro Gly Cys His Gly Ser Glu Pro Cys Ile Ile His Arg
1               5                   10                  15

<210> SEQ ID NO 16
<211> LENGTH: 17
<212> TYPE: PRT
<213> ORGANISM: artificial
<220> FEATURE:
<223> OTHER INFORMATION: peptide digest fragment

<400> SEQUENCE: 16

Gly Lys Pro Phe Gln Leu Glu Ala Val Phe Glu Ala Asn Gln Asn Thr
1               5                   10                  15

Lys

<210> SEQ ID NO 17
<211> LENGTH: 4
<212> TYPE: PRT
<213> ORGANISM: artificial
<220> FEATURE:
<223> OTHER INFORMATION: peptide digest fragment

<400> SEQUENCE: 17

Ile Glu Ile Lys
1

<210> SEQ ID NO 18
<211> LENGTH: 22
<212> TYPE: PRT
<213> ORGANISM: artificial
<220> FEATURE:
<223> OTHER INFORMATION: peptide digest fragment

<400> SEQUENCE: 18

Ala Ser Ile Asp Gly Leu Glu Val Asp Val Pro Gly Ile Asp Pro Asn
1               5                   10                  15

Ala Cys His Tyr Met Lys
            20

<210> SEQ ID NO 19
<211> LENGTH: 5
<212> TYPE: PRT
<213> ORGANISM: artificial
<220> FEATURE:
<223> OTHER INFORMATION: peptide digest fragment

<400> SEQUENCE: 19

Cys Pro Leu Val Lys
1               5
```

<210> SEQ ID NO 20
<211> LENGTH: 7
<212> TYPE: PRT
<213> ORGANISM: artificial
<220> FEATURE:
<223> OTHER INFORMATION: peptide digest fragment

<400> SEQUENCE: 20

Gly Gln Gln Tyr Asp Ile Lys
1               5

<210> SEQ ID NO 21
<211> LENGTH: 7
<212> TYPE: PRT
<213> ORGANISM: artificial
<220> FEATURE:
<223> OTHER INFORMATION: peptide digest fragment

<400> SEQUENCE: 21

Tyr Thr Trp Asn Val Pro Lys
1               5

<210> SEQ ID NO 22
<211> LENGTH: 4
<212> TYPE: PRT
<213> ORGANISM: artificial
<220> FEATURE:
<223> OTHER INFORMATION: peptide digest fragment

<400> SEQUENCE: 22

Ile Ala Pro Lys
1

<210> SEQ ID NO 23
<211> LENGTH: 9
<212> TYPE: PRT
<213> ORGANISM: artificial
<220> FEATURE:
<223> OTHER INFORMATION: peptide digest fragment

<400> SEQUENCE: 23

Ser Glu Asn Val Val Val Thr Val Lys
1               5

<210> SEQ ID NO 24
<211> LENGTH: 17
<212> TYPE: PRT
<213> ORGANISM: artificial
<220> FEATURE:
<223> OTHER INFORMATION: peptide digest fragment

<400> SEQUENCE: 24

Val Met Gly Asp Asp Gly Val Leu Ala Cys Ala Ile Ala Thr His Ala
1               5                   10                  15

Lys

<210> SEQ ID NO 25
<211> LENGTH: 26
<212> TYPE: PRT
<213> ORGANISM: artificial
<220> FEATURE:
<223> OTHER INFORMATION: peptide digest fragment

<400> SEQUENCE: 25

Met Ala Ser Ser Ser Ser Val Leu Leu Val Val Ala Leu Phe Ala Val
1               5                   10                  15

Phe Leu Gly Ser Ala His Gly Ile Pro Lys
            20              25

<210> SEQ ID NO 26
<211> LENGTH: 14
<212> TYPE: PRT
<213> ORGANISM: artificial
<220> FEATURE:
<223> OTHER INFORMATION: peptide digest fragment

<400> SEQUENCE: 26

Val Pro Pro Gly Pro Asn Ile Thr Ala Thr Tyr Gly Asp Lys
1               5                   10

<210> SEQ ID NO 27
<211> LENGTH: 5
<212> TYPE: PRT
<213> ORGANISM: artificial
<220> FEATURE:
<223> OTHER INFORMATION: peptide digest fragment

<400> SEQUENCE: 27

Trp Leu Asp Ala Lys
1               5

<210> SEQ ID NO 28
<211> LENGTH: 13
<212> TYPE: PRT
<213> ORGANISM: artificial
<220> FEATURE:
<223> OTHER INFORMATION: peptide digest fragment

<400> SEQUENCE: 28

Ser Thr Trp Tyr Gly Lys Pro Thr Ala Ala Gly Pro Lys
1               5                   10

<210> SEQ ID NO 29
<211> LENGTH: 9
<212> TYPE: PRT
<213> ORGANISM: artificial
<220> FEATURE:
<223> OTHER INFORMATION: peptide digest fragment

<400> SEQUENCE: 29

Asp Asn Gly Gly Ala Cys Gly Tyr Lys
1               5

<210> SEQ ID NO 30
<211> LENGTH: 20
<212> TYPE: PRT
<213> ORGANISM: artificial
<220> FEATURE:
<223> OTHER INFORMATION: peptide digest fragment

<400> SEQUENCE: 30

Asp Val Asp Lys Pro Pro Phe Ser Gly Met Thr Gly Cys Gly Asn Thr
1               5                   10                  15

Pro Ile Phe Lys
            20

<210> SEQ ID NO 31
<211> LENGTH: 9
<212> TYPE: PRT
<213> ORGANISM: artificial
<220> FEATURE:
<223> OTHER INFORMATION: peptide digest fragment

<400> SEQUENCE: 31

Gly Cys Gly Ser Cys Phe Glu Ile Lys
1               5

<210> SEQ ID NO 32
<211> LENGTH: 41
<212> TYPE: PRT
<213> ORGANISM: artificial
<220> FEATURE:
<223> OTHER INFORMATION: peptide digest fragment

<400> SEQUENCE: 32

Cys Thr Lys Pro Glu Ala Cys Ser Gly Glu Pro Val Val His Ile
1               5                   10                  15

Thr Asp Asp Asn Glu Glu Pro Ile Ala Ala Tyr His Phe Asp Leu Ser
            20                  25                  30

Gly Ile Ala Phe Gly Ser Met Ala Lys
        35                  40

<210> SEQ ID NO 33
<211> LENGTH: 5
<212> TYPE: PRT
<213> ORGANISM: artificial
<220> FEATURE:
<223> OTHER INFORMATION: peptide digest fragment

<400> SEQUENCE: 33

Gly Asp Glu Gln Lys
1               5

<210> SEQ ID NO 34
<211> LENGTH: 10
<212> TYPE: PRT
<213> ORGANISM: artificial
<220> FEATURE:
<223> OTHER INFORMATION: peptide digest fragment

<400> SEQUENCE: 34

Ser Ala Gly Glu Val Glu Ile Gln Phe Arg
1               5                   10

<210> SEQ ID NO 35
<211> LENGTH: 6
<212> TYPE: PRT
<213> ORGANISM: artificial
<220> FEATURE:
<223> OTHER INFORMATION: peptide digest fragment

<400> SEQUENCE: 35

Tyr Pro Glu Gly Thr Lys
1               5

<210> SEQ ID NO 36
<211> LENGTH: 7
<212> TYPE: PRT
<213> ORGANISM: artificial
<220> FEATURE:
<223> OTHER INFORMATION: peptide digest fragment

<400> SEQUENCE: 36

Val Thr Phe His Val Glu Lys
1               5

<210> SEQ ID NO 37

```
<211> LENGTH: 12
<212> TYPE: PRT
<213> ORGANISM: artificial
<220> FEATURE:
<223> OTHER INFORMATION: peptide digest fragment

<400> SEQUENCE: 37

Gly Ser Asn Pro Asn Tyr Leu Ala Leu Leu Val Lys
1               5                   10

<210> SEQ ID NO 38
<211> LENGTH: 14
<212> TYPE: PRT
<213> ORGANISM: artificial
<220> FEATURE:
<223> OTHER INFORMATION: peptide digest fragment

<400> SEQUENCE: 38

Phe Val Ala Gly Asp Gly Asp Val Val Ala Val Asp Ile Lys
1               5                   10

<210> SEQ ID NO 39
<211> LENGTH: 5
<212> TYPE: PRT
<213> ORGANISM: artificial
<220> FEATURE:
<223> OTHER INFORMATION: peptide digest fragment

<400> SEQUENCE: 39

Trp Ile Ala Leu Lys
1               5

<210> SEQ ID NO 40
<211> LENGTH: 8
<212> TYPE: PRT
<213> ORGANISM: artificial
<220> FEATURE:
<223> OTHER INFORMATION: peptide digest fragment

<400> SEQUENCE: 40

Glu Ser Trp Gly Ala Ile Trp Arg
1               5

<210> SEQ ID NO 41
<211> LENGTH: 8
<212> TYPE: PRT
<213> ORGANISM: artificial
<220> FEATURE:
<223> OTHER INFORMATION: peptide digest fragment

<400> SEQUENCE: 41

Ile Asp Thr Pro Glu Val Leu Lys
1               5

<210> SEQ ID NO 42
<211> LENGTH: 6
<212> TYPE: PRT
<213> ORGANISM: artificial
<220> FEATURE:
<223> OTHER INFORMATION: peptide digest fragment

<400> SEQUENCE: 42

Gly Pro Phe Thr Val Arg
1               5

<210> SEQ ID NO 43
<211> LENGTH: 8
```

```
<212> TYPE: PRT
<213> ORGANISM: artificial
<220> FEATURE:
<223> OTHER INFORMATION: peptide digest fragment

<400> SEQUENCE: 43

Tyr Thr Thr Glu Gly Gly Thr Lys
1               5

<210> SEQ ID NO 44
<211> LENGTH: 4
<212> TYPE: PRT
<213> ORGANISM: artificial
<220> FEATURE:
<223> OTHER INFORMATION: peptide digest fragment

<400> SEQUENCE: 44

Gly Glu Ala Lys
1

<210> SEQ ID NO 45
<211> LENGTH: 8
<212> TYPE: PRT
<213> ORGANISM: artificial
<220> FEATURE:
<223> OTHER INFORMATION: peptide digest fragment

<400> SEQUENCE: 45

Asp Val Ile Pro Glu Gly Trp Lys
1               5

<210> SEQ ID NO 46
<211> LENGTH: 8
<212> TYPE: PRT
<213> ORGANISM: artificial
<220> FEATURE:
<223> OTHER INFORMATION: peptide digest fragment

<400> SEQUENCE: 46

Ala Asp Thr Ala Tyr Glu Ser Lys
1               5

<210> SEQ ID NO 47
<211> LENGTH: 33
<212> TYPE: PRT
<213> ORGANISM: artificial
<220> FEATURE:
<223> OTHER INFORMATION: peptide digest fragment

<400> SEQUENCE: 47

Ala Asp Leu Gly Tyr Gly Pro Ala Thr Pro Ala Ala Pro Ala Ala Gly
1               5                   10                  15

Tyr Thr Pro Ala Thr Pro Ala Ala Pro Ala Gly Ala Asp Ala Ala Gly
                20                  25                  30

Lys

<210> SEQ ID NO 48
<211> LENGTH: 7
<212> TYPE: PRT
<213> ORGANISM: artificial
<220> FEATURE:
<223> OTHER INFORMATION: peptide digest fragment

<400> SEQUENCE: 48

Ala Thr Thr Glu Glu Gln Lys
1               5
```

```
<210> SEQ ID NO 49
<211> LENGTH: 4
<212> TYPE: PRT
<213> ORGANISM: artificial
<220> FEATURE:
<223> OTHER INFORMATION: peptide digest fragment

<400> SEQUENCE: 49

Leu Ile Glu Lys
1

<210> SEQ ID NO 50
<211> LENGTH: 6
<212> TYPE: PRT
<213> ORGANISM: artificial
<220> FEATURE:
<223> OTHER INFORMATION: peptide digest fragment

<400> SEQUENCE: 50

Ile Asn Ala Gly Phe Lys
1               5

<210> SEQ ID NO 51
<211> LENGTH: 13
<212> TYPE: PRT
<213> ORGANISM: artificial
<220> FEATURE:
<223> OTHER INFORMATION: peptide digest fragment

<400> SEQUENCE: 51

Ala Ala Leu Ala Gly Ala Gly Val Gln Pro Ala Asp Lys
1               5                   10

<210> SEQ ID NO 52
<211> LENGTH: 12
<212> TYPE: PRT
<213> ORGANISM: artificial
<220> FEATURE:
<223> OTHER INFORMATION: peptide digest fragment

<400> SEQUENCE: 52

Thr Phe Val Ala Thr Phe Gly Pro Ala Ser Asn Lys
1               5                   10

<210> SEQ ID NO 53
<211> LENGTH: 11
<212> TYPE: PRT
<213> ORGANISM: artificial
<220> FEATURE:
<223> OTHER INFORMATION: peptide digest fragment

<400> SEQUENCE: 53

Ala Phe Ala Glu Gly Leu Ser Gly Glu Pro Lys
1               5                   10

<210> SEQ ID NO 54
<211> LENGTH: 8
<212> TYPE: PRT
<213> ORGANISM: artificial
<220> FEATURE:
<223> OTHER INFORMATION: peptide digest fragment

<400> SEQUENCE: 54

Gly Ala Ala Glu Ser Ser Ser Lys
1               5
```

```
<210> SEQ ID NO 55
<211> LENGTH: 6
<212> TYPE: PRT
<213> ORGANISM: artificial
<220> FEATURE:
<223> OTHER INFORMATION: peptide digest fragment

<400> SEQUENCE: 55

Ala Ala Leu Thr Ser Lys
1               5

<210> SEQ ID NO 56
<211> LENGTH: 6
<212> TYPE: PRT
<213> ORGANISM: artificial
<220> FEATURE:
<223> OTHER INFORMATION: peptide digest fragment

<400> SEQUENCE: 56

Leu Asp Ala Ala Tyr Lys
1               5

<210> SEQ ID NO 57
<211> LENGTH: 4
<212> TYPE: PRT
<213> ORGANISM: artificial
<220> FEATURE:
<223> OTHER INFORMATION: peptide digest fragment

<400> SEQUENCE: 57

Leu Ala Tyr Lys
1

<210> SEQ ID NO 58
<211> LENGTH: 10
<212> TYPE: PRT
<213> ORGANISM: artificial
<220> FEATURE:
<223> OTHER INFORMATION: peptide digest fragment

<400> SEQUENCE: 58

Thr Ala Glu Gly Ala Thr Pro Glu Ala Lys
1               5                   10

<210> SEQ ID NO 59
<211> LENGTH: 13
<212> TYPE: PRT
<213> ORGANISM: artificial
<220> FEATURE:
<223> OTHER INFORMATION: peptide digest fragment

<400> SEQUENCE: 59

Tyr Asp Ala Tyr Val Ala Thr Leu Ser Glu Ala Leu Arg
1               5                   10

<210> SEQ ID NO 60
<211> LENGTH: 19
<212> TYPE: PRT
<213> ORGANISM: artificial
<220> FEATURE:
<223> OTHER INFORMATION: peptide digest fragment

<400> SEQUENCE: 60

Ile Ile Ala Gly Thr Leu Glu Val His Ala Val Lys Pro Ala Ala Glu
1               5                   10                  15

Glu Val Lys
```

<210> SEQ ID NO 61
<211> LENGTH: 12
<212> TYPE: PRT
<213> ORGANISM: artificial
<220> FEATURE:
<223> OTHER INFORMATION: peptide digest fragment

<400> SEQUENCE: 61

Val Ile Pro Ala Gly Glu Leu Gln Val Ile Glu Lys
1               5                   10

<210> SEQ ID NO 62
<211> LENGTH: 6
<212> TYPE: PRT
<213> ORGANISM: artificial
<220> FEATURE:
<223> OTHER INFORMATION: peptide digest fragment

<400> SEQUENCE: 62

Val Asp Ala Ala Phe Lys
1               5

<210> SEQ ID NO 63
<211> LENGTH: 14
<212> TYPE: PRT
<213> ORGANISM: artificial
<220> FEATURE:
<223> OTHER INFORMATION: peptide digest fragment

<400> SEQUENCE: 63

Val Ala Ala Thr Ala Ala Asn Ala Ala Pro Ala Asn Asp Lys
1               5                   10

<210> SEQ ID NO 64
<211> LENGTH: 13
<212> TYPE: PRT
<213> ORGANISM: artificial
<220> FEATURE:
<223> OTHER INFORMATION: peptide digest fragment

<400> SEQUENCE: 64

Phe Thr Val Phe Glu Ala Ala Phe Asn Asp Glu Ile Lys
1               5                   10

<210> SEQ ID NO 65
<211> LENGTH: 11
<212> TYPE: PRT
<213> ORGANISM: artificial
<220> FEATURE:
<223> OTHER INFORMATION: peptide digest fragment

<400> SEQUENCE: 65

Ala Ser Thr Gly Gly Ala Tyr Glu Ser Tyr Lys
1               5                   10

<210> SEQ ID NO 66
<211> LENGTH: 10
<212> TYPE: PRT
<213> ORGANISM: artificial
<220> FEATURE:
<223> OTHER INFORMATION: peptide digest fragment

<400> SEQUENCE: 66

Phe Ile Pro Ala Leu Glu Ala Ala Val Lys
1               5                   10

```
<210> SEQ ID NO 67
<211> LENGTH: 14
<212> TYPE: PRT
<213> ORGANISM: artificial
<220> FEATURE:
<223> OTHER INFORMATION: peptide digest fragment

<400> SEQUENCE: 67

Gln Ala Tyr Ala Ala Thr Val Ala Thr Ala Pro Glu Val Lys
1               5                   10

<210> SEQ ID NO 68
<211> LENGTH: 9
<212> TYPE: PRT
<213> ORGANISM: artificial
<220> FEATURE:
<223> OTHER INFORMATION: peptide digest fragment

<400> SEQUENCE: 68

Tyr Thr Val Phe Glu Thr Ala Leu Lys
1               5

<210> SEQ ID NO 69
<211> LENGTH: 10
<212> TYPE: PRT
<213> ORGANISM: artificial
<220> FEATURE:
<223> OTHER INFORMATION: peptide digest fragment

<400> SEQUENCE: 69

Ala Ile Thr Ala Met Ser Glu Ala Gln Lys
1               5                   10

<210> SEQ ID NO 70
<211> LENGTH: 30
<212> TYPE: PRT
<213> ORGANISM: artificial
<220> FEATURE:
<223> OTHER INFORMATION: peptide digest fragment

<400> SEQUENCE: 70

Ala Lys Pro Ala Ala Ala Ala Thr Ala Thr Ala Thr Ala Ala Val Gly
1               5                   10                  15

Ala Ala Thr Gly Ala Ala Thr Ala Ala Thr Gly Gly Tyr Lys
            20                  25                  30

<210> SEQ ID NO 71
<211> LENGTH: 7
<212> TYPE: PRT
<213> ORGANISM: artificial
<220> FEATURE:
<223> OTHER INFORMATION: peptide digest fragment

<400> SEQUENCE: 71

Ala Ala Ala Ala Val Pro Arg
1               5

<210> SEQ ID NO 72
<211> LENGTH: 5
<212> TYPE: PRT
<213> ORGANISM: artificial
<220> FEATURE:
<223> OTHER INFORMATION: peptide digest fragment

<400> SEQUENCE: 72

Gly Gly Pro Gly Arg
```

```
1               5
```

<210> SEQ ID NO 73
<211> LENGTH: 22
<212> TYPE: PRT
<213> ORGANISM: artificial
<220> FEATURE:
<223> OTHER INFORMATION: peptide digest fragment

<400> SEQUENCE: 73

```
Ser Tyr Thr Ala Asp Ala Gly Tyr Ala Pro Thr Pro Ala Ala Ala
1               5                   10                  15

Gly Ala Ala Ala Gly Lys
            20
```

<210> SEQ ID NO 74
<211> LENGTH: 7
<212> TYPE: PRT
<213> ORGANISM: artificial
<220> FEATURE:
<223> OTHER INFORMATION: peptide digest fragment

<400> SEQUENCE: 74

```
Ala Thr Thr Glu Glu Gln Lys
1               5
```

<210> SEQ ID NO 75
<211> LENGTH: 10
<212> TYPE: PRT
<213> ORGANISM: artificial
<220> FEATURE:
<223> OTHER INFORMATION: peptide digest fragment

<400> SEQUENCE: 75

```
Leu Ile Glu Asp Ile Asn Val Gly Phe Lys
1               5                   10
```

<210> SEQ ID NO 76
<211> LENGTH: 14
<212> TYPE: PRT
<213> ORGANISM: artificial
<220> FEATURE:
<223> OTHER INFORMATION: peptide digest fragment

<400> SEQUENCE: 76

```
Ala Ala Val Ala Ala Ala Ala Ser Val Pro Ala Ala Asp Lys
1               5                   10
```

<210> SEQ ID NO 77
<211> LENGTH: 11
<212> TYPE: PRT
<213> ORGANISM: artificial
<220> FEATURE:
<223> OTHER INFORMATION: peptide digest fragment

<400> SEQUENCE: 77

```
Thr Phe Glu Ala Ala Phe Thr Ser Ser Ser Lys
1               5                   10
```

<210> SEQ ID NO 78
<211> LENGTH: 5
<212> TYPE: PRT
<213> ORGANISM: artificial
<220> FEATURE:
<223> OTHER INFORMATION: peptide digest fragment

<400> SEQUENCE: 78

Ala Ala Ala Ala Lys
1               5

<210> SEQ ID NO 79
<211> LENGTH: 7
<212> TYPE: PRT
<213> ORGANISM: artificial
<220> FEATURE:
<223> OTHER INFORMATION: peptide digest fragment

<400> SEQUENCE: 79

Ala Pro Gly Leu Val Pro Lys
1               5

<210> SEQ ID NO 80
<211> LENGTH: 10
<212> TYPE: PRT
<213> ORGANISM: artificial
<220> FEATURE:
<223> OTHER INFORMATION: peptide digest fragment

<400> SEQUENCE: 80

Leu Asp Ala Ala Tyr Ser Val Ala Tyr Lys
1               5                   10

<210> SEQ ID NO 81
<211> LENGTH: 10
<212> TYPE: PRT
<213> ORGANISM: artificial
<220> FEATURE:
<223> OTHER INFORMATION: peptide digest fragment

<400> SEQUENCE: 81

Ala Ala Val Gly Ala Thr Pro Glu Ala Lys
1               5                   10

<210> SEQ ID NO 82
<211> LENGTH: 13
<212> TYPE: PRT
<213> ORGANISM: artificial
<220> FEATURE:
<223> OTHER INFORMATION: peptide digest fragment

<400> SEQUENCE: 82

Phe Asp Ser Phe Val Ala Ser Leu Thr Glu Ala Leu Arg
1               5                   10

<210> SEQ ID NO 83
<211> LENGTH: 22
<212> TYPE: PRT
<213> ORGANISM: artificial
<220> FEATURE:
<223> OTHER INFORMATION: peptide digest fragment

<400> SEQUENCE: 83

Val Ile Ala Gly Ala Leu Glu Val His Ala Val Lys Pro Val Thr Glu
1               5                   10                  15

Glu Pro Gly Met Ala Lys
            20

<210> SEQ ID NO 84
<211> LENGTH: 11
<212> TYPE: PRT
<213> ORGANISM: artificial
<220> FEATURE:
<223> OTHER INFORMATION: peptide digest fragment

<400> SEQUENCE: 84

Ile Pro Ala Gly Glu Leu Gln Ile Ile Asp Lys
1               5                   10

<210> SEQ ID NO 85
<211> LENGTH: 6
<212> TYPE: PRT
<213> ORGANISM: artificial
<220> FEATURE:
<223> OTHER INFORMATION: peptide digest fragment

<400> SEQUENCE: 85

Ile Asp Ala Ala Phe Lys
1               5

<210> SEQ ID NO 86
<211> LENGTH: 14
<212> TYPE: PRT
<213> ORGANISM: artificial
<220> FEATURE:
<223> OTHER INFORMATION: peptide digest fragment

<400> SEQUENCE: 86

Val Ala Ala Thr Ala Ala Ala Thr Ala Pro Ala Asp Asp Lys
1               5                   10

<210> SEQ ID NO 87
<211> LENGTH: 10
<212> TYPE: PRT
<213> ORGANISM: artificial
<220> FEATURE:
<223> OTHER INFORMATION: peptide digest fragment

<400> SEQUENCE: 87

Phe Thr Val Phe Glu Ala Ala Phe Asn Lys
1               5                   10

<210> SEQ ID NO 88
<211> LENGTH: 11
<212> TYPE: PRT
<213> ORGANISM: artificial
<220> FEATURE:
<223> OTHER INFORMATION: peptide digest fragment

<400> SEQUENCE: 88

Glu Ser Thr Gly Gly Ala Tyr Asp Thr Tyr Lys
1               5                   10

<210> SEQ ID NO 89
<211> LENGTH: 10
<212> TYPE: PRT
<213> ORGANISM: artificial
<220> FEATURE:
<223> OTHER INFORMATION: peptide digest fragment

<400> SEQUENCE: 89

Cys Ile Pro Ser Leu Glu Ala Ala Val Lys
1               5                   10

<210> SEQ ID NO 90
<211> LENGTH: 14
<212> TYPE: PRT
<213> ORGANISM: artificial
<220> FEATURE:
<223> OTHER INFORMATION: peptide digest fragment

```
<400> SEQUENCE: 90

Gln Ala Tyr Ala Ala Thr Val Ala Ala Ala Pro Gln Val Lys
1               5                   10

<210> SEQ ID NO 91
<211> LENGTH: 10
<212> TYPE: PRT
<213> ORGANISM: artificial
<220> FEATURE:
<223> OTHER INFORMATION: peptide digest fragment

<400> SEQUENCE: 91

Tyr Ala Val Phe Glu Ala Ala Leu Thr Lys
1               5                   10

<210> SEQ ID NO 92
<211> LENGTH: 10
<212> TYPE: PRT
<213> ORGANISM: artificial
<220> FEATURE:
<223> OTHER INFORMATION: peptide digest fragment

<400> SEQUENCE: 92

Ala Ile Thr Ala Met Ser Glu Val Gln Lys
1               5                   10

<210> SEQ ID NO 93
<211> LENGTH: 35
<212> TYPE: PRT
<213> ORGANISM: artificial
<220> FEATURE:
<223> OTHER INFORMATION: peptide digest fragment

<400> SEQUENCE: 93

Val Ser Gln Pro Ala Thr Gly Ala Ala Thr Val Ala Ala Gly Ala Ala
1               5                   10                  15
Thr Thr Ala Ala Gly Ala Ala Ser Gly Ala Ala Thr Val Ala Ala Gly
            20                  25                  30
Gly Tyr Lys
        35

<210> SEQ ID NO 94
<211> LENGTH: 18
<212> TYPE: PRT
<213> ORGANISM: artificial
<220> FEATURE:
<223> OTHER INFORMATION: peptide digest fragment

<400> SEQUENCE: 94

Met Gly Val Phe Asn Tyr Glu Thr Glu Thr Thr Ser Val Ile Pro Ala
1               5                   10                  15
Ala Arg

<210> SEQ ID NO 95
<211> LENGTH: 12
<212> TYPE: PRT
<213> ORGANISM: artificial
<220> FEATURE:
<223> OTHER INFORMATION: peptide digest fragment

<400> SEQUENCE: 95

Ala Phe Ile Leu Asp Gly Asp Asn Leu Phe Pro Lys
1               5                   10
```

```
<210> SEQ ID NO 96
<211> LENGTH: 24
<212> TYPE: PRT
<213> ORGANISM: artificial
<220> FEATURE:
<223> OTHER INFORMATION: peptide digest fragment

<400> SEQUENCE: 96

Val Ala Pro Gln Ala Ile Ser Ser Val Glu Asn Ile Phe Thr Glu Gly
1               5                   10                  15

Asn Gly Gly Pro Gly Thr Ile Lys
            20

<210> SEQ ID NO 97
<211> LENGTH: 10
<212> TYPE: PRT
<213> ORGANISM: artificial
<220> FEATURE:
<223> OTHER INFORMATION: peptide digest fragment

<400> SEQUENCE: 97

Ile Ser Phe Pro Glu Gly Leu Pro Phe Lys
1               5                   10

<210> SEQ ID NO 98
<211> LENGTH: 10
<212> TYPE: PRT
<213> ORGANISM: artificial
<220> FEATURE:
<223> OTHER INFORMATION: peptide digest fragment

<400> SEQUENCE: 98

Val Asp Glu Val Asp His Thr Asn Phe Lys
1               5                   10

<210> SEQ ID NO 99
<211> LENGTH: 17
<212> TYPE: PRT
<213> ORGANISM: artificial
<220> FEATURE:
<223> OTHER INFORMATION: peptide digest fragment

<400> SEQUENCE: 99

Tyr Asn Tyr Ser Val Ile Glu Gly Gly Pro Ile Gly Asp Thr Leu Glu
1               5                   10                  15

Lys

<210> SEQ ID NO 100
<211> LENGTH: 6
<212> TYPE: PRT
<213> ORGANISM: artificial
<220> FEATURE:
<223> OTHER INFORMATION: peptide digest fragment

<400> SEQUENCE: 100

Ile Ser Asn Glu Ile Lys
1               5

<210> SEQ ID NO 101
<211> LENGTH: 14
<212> TYPE: PRT
<213> ORGANISM: artificial
<220> FEATURE:
<223> OTHER INFORMATION: peptide digest fragment

<400> SEQUENCE: 101
```

```
Phe Thr Ile Val Ala Thr Pro Asp Gly Gly Ser Ile Leu Lys
1               5                   10

<210> SEQ ID NO 102
<211> LENGTH: 4
<212> TYPE: PRT
<213> ORGANISM: artificial
<220> FEATURE:
<223> OTHER INFORMATION: peptide digest fragment

<400> SEQUENCE: 102

Ile Ser Asn Lys
1

<210> SEQ ID NO 103
<211> LENGTH: 4
<212> TYPE: PRT
<213> ORGANISM: artificial
<220> FEATURE:
<223> OTHER INFORMATION: peptide digest fragment

<400> SEQUENCE: 103

Tyr His Thr Lys
1

<210> SEQ ID NO 104
<211> LENGTH: 6
<212> TYPE: PRT
<213> ORGANISM: artificial
<220> FEATURE:
<223> OTHER INFORMATION: peptide digest fragment

<400> SEQUENCE: 104

Gly Asp His Glu Val Lys
1               5

<210> SEQ ID NO 105
<211> LENGTH: 5
<212> TYPE: PRT
<213> ORGANISM: artificial
<220> FEATURE:
<223> OTHER INFORMATION: peptide digest fragment

<400> SEQUENCE: 105

Ala Glu Gln Val Lys
1               5

<210> SEQ ID NO 106
<211> LENGTH: 8
<212> TYPE: PRT
<213> ORGANISM: artificial
<220> FEATURE:
<223> OTHER INFORMATION: peptide digest fragment

<400> SEQUENCE: 106

Glu Met Gly Glu Thr Leu Leu Arg
1               5

<210> SEQ ID NO 107
<211> LENGTH: 14
<212> TYPE: PRT
<213> ORGANISM: artificial
<220> FEATURE:
<223> OTHER INFORMATION: peptide digest fragment

<400> SEQUENCE: 107

Ala Val Glu Ser Tyr Leu Leu Ala His Ser Asp Ala Tyr Asn
```

<210> SEQ ID NO 108
<211> LENGTH: 129
<212> TYPE: PRT
<213> ORGANISM: Dermatophagoides pteronyssinus

<400> SEQUENCE: 108

Ser Gln Val Asp Val Lys Asp Cys Ala Asn His Glu Ile Lys Lys Val
1               5                   10                  15
Leu Val Pro Gly Cys His Gly Ser Glu Pro Cys Ile Ile His Arg Gly
            20                  25                  30
Lys Pro Phe Gln Leu Glu Ala Val Phe Glu Ala Asn Gln Asn Thr Lys
        35                  40                  45
Thr Ala Lys Ile Glu Ile Lys Ala Ser Ile Asp Gly Leu Glu Val Asp
    50                  55                  60
Val Pro Gly Ile Asp Pro Asn Ala Cys His Tyr Met Lys Cys Pro Leu
65                  70                  75                  80
Val Lys Gly Gln Gln Tyr Asp Ile Lys Tyr Thr Trp Asn Val Pro Lys
                85                  90                  95
Ile Ala Pro Lys Ser Glu Asn Val Val Thr Val Lys Val Met Gly
            100                 105                 110
Asp Asp Gly Val Leu Ala Cys Ala Ile Ala Thr His Ala Lys Ile Arg
        115                 120                 125
Asp

<210> SEQ ID NO 109
<211> LENGTH: 129
<212> TYPE: PRT
<213> ORGANISM: Dermatophagoides pteronyssinus

<400> SEQUENCE: 109

Ser Glu Val Asp Val Lys Asp Cys Ala Asn His Glu Ile Lys Lys Val
1               5                   10                  15
Leu Val Pro Gly Cys His Gly Ser Glu Pro Cys Ile Ile His Arg Gly
            20                  25                  30
Lys Pro Phe Gln Leu Glu Ala Val Phe Glu Ala Asn Gln Asn Thr Lys
        35                  40                  45
Thr Ala Lys Ile Glu Ile Lys Ala Ser Ile Asp Gly Leu Glu Val Asp
    50                  55                  60
Val Pro Gly Ile Asp Pro Asn Ala Cys His Tyr Met Lys Cys Pro Leu
65                  70                  75                  80
Val Lys Gly Gln Gln Tyr Asp Ile Lys Tyr Thr Trp Asn Val Pro Lys
                85                  90                  95
Ile Ala Pro Lys Ser Glu Asn Val Val Thr Val Lys Val Met Gly
            100                 105                 110
Asp Asp Gly Val Leu Ala Cys Ala Ile Ala Thr His Ala Lys Ile Arg
        115                 120                 125
Asp

<210> SEQ ID NO 110
<211> LENGTH: 145
<212> TYPE: PRT
<213> ORGANISM: Dermatophagoides pteronyssinus

<400> SEQUENCE: 110

Met Tyr Lys Ile Leu Cys Leu Ser Leu Leu Val Ala Ala Val Ala Arg

```
                1               5                   10                  15
Asp Gln Val Asp Val Lys Asp Cys Ala Asn His Glu Ile Lys Lys Val
                20                  25                  30

Leu Val Pro Gly Cys His Gly Ser Glu Pro Cys Ile Ile His Arg Gly
            35                  40                  45

Lys Pro Phe Gln Leu Glu Ala Val Phe Glu Ala Asn Gln Asn Thr Lys
        50                  55                  60

Thr Ala Lys Ile Glu Ile Lys Ala Ser Ile Asp Gly Leu Glu Val Asp
65                  70                  75                  80

Val Pro Gly Ile Asp Pro Asn Ala Cys His Tyr Met Lys Cys Pro Leu
                85                  90                  95

Val Lys Gly Gln Gln Tyr Asp Ile Lys Tyr Thr Trp Asn Val Pro Lys
            100                 105                 110

Ile Ala Pro Lys Ser Glu Asn Val Val Thr Val Lys Val Met Gly
        115                 120                 125

Asp Asp Gly Val Leu Ala Cys Ala Ile Ala Thr His Ala Lys Ile Arg
130                 135                 140

Asp
145

<210> SEQ ID NO 111
<211> LENGTH: 146
<212> TYPE: PRT
<213> ORGANISM: Dermatophagoides pteronyssinus

<400> SEQUENCE: 111

Met Met Tyr Lys Ile Leu Cys Leu Ser Leu Leu Val Ala Ala Val Ala
1               5                   10                  15

Arg Asp Gln Val Asp Val Lys Asp Cys Ala Asn His Glu Ile Lys Lys
                20                  25                  30

Val Leu Val Pro Gly Cys His Gly Ser Glu Pro Cys Ile Ile His Arg
            35                  40                  45

Gly Lys Pro Phe Gln Leu Glu Ala Val Phe Glu Ala Asn Gln Asn Thr
        50                  55                  60

Lys Thr Ala Lys Ile Glu Ile Lys Ala Ser Ile Asp Gly Leu Glu Val
65                  70                  75                  80

Asp Val Pro Gly Ile Asp Pro Asn Ala Cys His Tyr Met Lys Cys Pro
                85                  90                  95

Leu Val Lys Gly Gln Gln Tyr Asp Ile Lys Tyr Thr Trp Asn Val Pro
            100                 105                 110

Lys Ile Ala Pro Lys Ser Glu Asn Val Val Thr Val Lys Val Met
        115                 120                 125

Gly Asp Asp Gly Val Leu Ala Cys Ala Ile Ala Thr His Ala Lys Ile
130                 135                 140

Arg Asp
145

<210> SEQ ID NO 112
<211> LENGTH: 141
<212> TYPE: PRT
<213> ORGANISM: Lepidoglyphus destructor

<400> SEQUENCE: 112

Met Met Lys Phe Ile Ala Leu Phe Ala Leu Val Ala Val Ala Ser Ala
1               5                   10                  15

Gly Lys Met Thr Phe Lys Asp Cys Gly His Gly Glu Val Thr Glu Leu
```

```
                    20                  25                  30
Asp Ile Thr Gly Cys Ser Gly Asp Thr Cys Val Ile His Arg Gly Glu
                35                  40                  45

Lys Met Thr Leu Glu Ala Lys Phe Ala Ala Asn Gln Asp Thr Ala Lys
 50                  55                  60

Val Thr Ile Lys Val Leu Ala Lys Val Ala Gly Thr Thr Ile Gln Val
 65                  70                  75                  80

Pro Gly Leu Glu Thr Asp Gly Cys Lys Phe Ile Lys Cys Pro Val Lys
                 85                  90                  95

Lys Gly Glu Ala Leu Asp Phe Ile Tyr Ser Gly Thr Ile Pro Ala Ile
                100                 105                 110

Thr Pro Lys Val Lys Ala Asp Val Thr Ala Glu Leu Ile Gly Asp His
                115                 120                 125

Gly Val Met Ala Cys Gly Thr Val His Gly Val Gln Glu
    130                 135                 140

<210> SEQ ID NO 113
<211> LENGTH: 98
<212> TYPE: PRT
<213> ORGANISM: Lepidoglyphus destructor

<400> SEQUENCE: 113

Ile His Arg Gly Glu Lys Met Thr Leu Glu Ala Lys Phe Ala Ala Asn
1               5                   10                  15

Gln Asp Thr Ala Lys Val Thr Ile Lys Val Leu Ala Lys Val Ala Gly
                20                  25                  30

Thr Thr Ile Gln Val Pro Gly Leu Glu Thr Asp Gly Cys Lys Phe Ile
            35                  40                  45

Lys Cys Pro Val Lys Lys Gly Glu Ala Leu Asp Phe Ile Tyr Ser Gly
        50                  55                  60

Thr Ile Pro Ala Ile Thr Pro Lys Val Lys Ala Asp Val Thr Ala Glu
65                  70                  75                  80

Leu Ile Gly Asp His Gly Val Met Ala Cys Gly Thr Val His Gly Gln
                85                  90                  95

Val Glu

<210> SEQ ID NO 114
<211> LENGTH: 141
<212> TYPE: PRT
<213> ORGANISM: Lepidoglyphus destructor

<400> SEQUENCE: 114

Met Met Lys Phe Ile Ala Leu Phe Ala Leu Val Ala Val Ala Ser Ala
1               5                   10                  15

Gly Lys Met Thr Phe Lys Asp Cys Gly His Gly Glu Val Thr Glu Leu
                20                  25                  30

Asp Ile Thr Gly Cys Ser Gly Asp Thr Cys Val Ile His Arg Gly Glu
            35                  40                  45

Lys Met Thr Leu Glu Ala Lys Phe Ala Ala Asn Gln Asp Thr Ala Lys
        50                  55                  60

Val Thr Ile Lys Val Leu Ala Lys Val Ala Gly Thr Thr Ile Gln Val
65                  70                  75                  80

Pro Gly Leu Glu Thr Asp Gly Cys Lys Phe Ile Lys Cys Pro Val Lys
                85                  90                  95

Lys Gly Glu Ala Leu Asp Phe Ile Tyr Ser Gly Thr Ile Pro Ala Ile
                100                 105                 110
```

```
Thr Pro Lys Val Lys Ala Asp Val Thr Ala Glu Leu Ile Gly Asp His
        115                 120                 125

Gly Val Met Ala Cys Gly Thr Val His Gly Gln Val Glu
        130                 135                 140

<210> SEQ ID NO 115
<211> LENGTH: 141
<212> TYPE: PRT
<213> ORGANISM: Lepidoglyphus destructor

<400> SEQUENCE: 115

Met Met Lys Phe Ile Ala Leu Phe Ala Leu Val Ala Val Ala Ser Ala
1               5                   10                  15

Gly Lys Met Thr Phe Lys Asp Cys Gly His Gly Glu Val Thr Glu Leu
            20                  25                  30

Asp Ile Thr Gly Cys Ser Gly Asp Thr Cys Val Ile His Arg Gly Glu
        35                  40                  45

Lys Met Thr Leu Glu Ala Lys Phe Ala Ala Asn Gln Asp Thr Ala Lys
    50                  55                  60

Val Thr Ile Lys Val Leu Thr Lys Val Ala Gly Thr Thr Ile Gln Val
65                  70                  75                  80

Pro Gly Leu Glu Thr Asp Gly Cys Lys Phe Ile Lys Cys Pro Val Lys
                85                  90                  95

Lys Gly Glu Ala Leu Asp Phe Ile Tyr Ser Gly Thr Ile Pro Ala Ile
            100                 105                 110

Thr Pro Lys Val Lys Ala Asp Val Thr Ala Glu Leu Ile Gly Asp His
        115                 120                 125

Gly Val Met Ala Cys Gly Thr Val His Gly Gln Val Glu
        130                 135                 140

<210> SEQ ID NO 116
<211> LENGTH: 141
<212> TYPE: PRT
<213> ORGANISM: Lepidoglyphus destructor

<400> SEQUENCE: 116

Met Met Lys Phe Ile Ala Leu Phe Ala Leu Val Ala Val Ala Ser Ala
1               5                   10                  15

Gly Lys Met Thr Phe Lys Asp Cys Gly His Gly Glu Val Thr Glu Leu
            20                  25                  30

Asp Ile Ser Gly Cys Ser Gly Asp Thr Cys Val Ile His Arg Gly Gln
        35                  40                  45

Lys Met Thr Leu Asp Ala Lys Phe Ala Ala Asn Gln Asp Thr Asn Lys
    50                  55                  60

Val Thr Ile Lys Val Leu Ala Lys Val Ala Gly Thr Thr Ile Gln Val
65                  70                  75                  80

Pro Gly Leu Glu Thr Asp Gly Cys Lys Val Leu Lys Cys Pro Ile Lys
                85                  90                  95

Lys Gly Glu Ala Leu Asp Phe Asn Tyr Gly Met Thr Ile Pro Ala Ile
            100                 105                 110

Thr Pro Lys Ile Lys Ala Asp Val Thr Ala Glu Leu Val Gly Asp His
        115                 120                 125

Gly Val Met Ala Cys Gly Thr Ile His Gly Val Gln Glu
        130                 135                 140

<210> SEQ ID NO 117
```

<211> LENGTH: 141
<212> TYPE: PRT
<213> ORGANISM: Lepidoglyphus destructor

<400> SEQUENCE: 117

```
Met Met Lys Phe Ile Ala Leu Phe Ala Leu Val Ala Val Ala Ser Ala
1               5                   10                  15

Gly Lys Met Thr Phe Lys Asp Cys Gly His Gly Glu Val Thr Glu Leu
            20                  25                  30

Asp Ile Ser Gly Cys Ser Gly Asp Thr Cys Val Ile His Arg Gly Gln
        35                  40                  45

Lys Met Thr Leu Asp Ala Lys Phe Ala Ala Asn Gln Asp Thr Asn Lys
50                  55                  60

Val Thr Ile Lys Val Leu Ala Lys Val Ala Gly Thr Thr Ile Gln Val
65                  70                  75                  80

Pro Gly Leu Glu Thr Asp Gly Cys Lys Val Leu Lys Cys Pro Ile Lys
                85                  90                  95

Lys Gly Glu Ala Leu Asp Phe Asn Tyr Gly Met Thr Ile Pro Ala Ile
            100                 105                 110

Thr Pro Lys Ile Lys Ala Asp Val Thr Ala Glu Leu Val Gly Asp His
        115                 120                 125

Gly Val Met Ala Cys Gly Thr Ile His Gly Gln Val Glu
    130                 135                 140
```

<210> SEQ ID NO 118
<211> LENGTH: 141
<212> TYPE: PRT
<213> ORGANISM: Lepidoglyphus destructor

<400> SEQUENCE: 118

```
Met Met Lys Phe Ile Ala Leu Phe Ala Leu Val Ala Val Ala Ser Ala
1               5                   10                  15

Gly Lys Met Thr Phe Lys Asp Cys Gly His Gly Glu Val Thr Glu Leu
            20                  25                  30

Asp Ile Ser Gly Cys Ser Gly Asp Thr Cys Val Ile His Arg Gly Gln
        35                  40                  45

Lys Met Thr Leu Asp Ala Lys Phe Ala Ala Asn Gln Asp Thr Asn Lys
50                  55                  60

Val Thr Ile Lys Val Leu Ala Lys Val Ala Gly Thr Thr Ile Gln Val
65                  70                  75                  80

Pro Gly Leu Glu Thr Asp Gly Cys Lys Val Leu Lys Cys Pro Ile Lys
                85                  90                  95

Lys Gly Glu Ala Leu Asp Phe Asn Tyr Gly Met Thr Ile Pro Ala Ile
            100                 105                 110

Thr Pro Lys Ile Lys Val Asp Val Thr Ala Glu Leu Val Gly Asp His
        115                 120                 125

Gly Val Met Ala Cys Gly Thr Ile His Gly Gln Val Glu
    130                 135                 140
```

<210> SEQ ID NO 119
<211> LENGTH: 125
<212> TYPE: PRT
<213> ORGANISM: Glycyphagus domesticus

<400> SEQUENCE: 119

```
Gly Lys Met Lys Phe Lys Asp Cys Gly Lys Gly Glu Val Thr Glu Leu
1               5                   10                  15
```

Asp Ile Thr Asp Cys Ser Gly Asp Phe Cys Val Ile His Arg Gly Lys
         20                  25                  30

Pro Leu Thr Leu Glu Ala Lys Phe Ala Ala Asn Gln Asp Thr Thr Lys
             35                  40                  45

Ala Thr Ile Lys Val Leu Ala Lys Val Ala Gly Thr Pro Ile Gln Val
 50                  55                  60

Pro Gly Leu Glu Thr Asp Gly Cys Lys Phe Val Lys Cys Pro Ile Lys
65                  70                  75                  80

Lys Gly Asp Pro Ile Asp Phe Lys Tyr Thr Thr Thr Val Pro Ala Ile
                 85                  90                  95

Leu Pro Lys Val Lys Ala Glu Val Thr Ala Glu Leu Val Gly Asp His
                100                 105                 110

Gly Val Leu Ala Cys Gly Arg Phe Gly Arg Gln Val Glu
            115                 120                 125

<210> SEQ ID NO 120
<211> LENGTH: 128
<212> TYPE: PRT
<213> ORGANISM: Glycyphagus domesticus

<400> SEQUENCE: 120

Gly Lys Met Asn Phe Thr Asp Cys Gly His Asn Glu Ile Lys Glu Leu
1               5                   10                  15

Ser Val Asn Cys Thr Gly Asn Tyr Cys Val Ile His Arg Gly Lys
             20                  25                  30

Pro Leu Thr Leu Asp Ala Lys Phe Asp Ala Asn Gln Asp Thr Ala Ser
             35                  40                  45

Val Gly Leu Val Leu Thr Ala Ile Ile Asp Gly Asp Ile Ala Ile Asp
 50                  55                  60

Ile Pro Gly Leu Glu Thr Asn Ala Cys Lys Leu Met Lys Cys Pro Ile
65                  70                  75                  80

Arg Lys Gly Glu His Gln Glu Leu Ile Tyr Asn Ile Gly Glu Ile Pro
                 85                  90                  95

Asp Ala Thr Pro Glu Ile Lys Ala Lys Val Lys Ala Gln Leu Ile Gly
                100                 105                 110

Glu His Gly Val Leu Ala Cys Gly Trp Val Asp Gly Glu Val Gln Glu
            115                 120                 125

<210> SEQ ID NO 121
<211> LENGTH: 143
<212> TYPE: PRT
<213> ORGANISM: Psoroptes ovis

<400> SEQUENCE: 121

Met Met Lys Thr Leu Val Val Leu Ala Ile Thr Leu Ala Val Val Ser
1               5                   10                  15

Ala Gly Lys Val Lys Phe Gln Asp Cys Gly Lys Gly Glu Val Glu Ser
             20                  25                  30

Leu Glu Val Glu Gly Cys Ser Gly Asp Tyr Cys Val Ile His Lys Gly
             35                  40                  45

Lys Lys Leu Asp Leu Ala Ile Ser Val Thr Ser Asn Gln Asp Ser Ala
 50                  55                  60

Asn Leu Lys Leu Asp Ile Val Ala Asp Ile Asn Gly Val Gln Ile Glu
65                  70                  75                  80

Val Pro Gly Val Asp His Asp Gly Cys His Tyr Val Lys Cys Pro Ile
                 85                  90                  95

```
Lys Lys Gly Gln His Phe Asp Val Lys Tyr Thr Tyr Ser Ile Pro Ala
                100                 105                 110

Ile Leu Pro Thr Thr Lys Ala Lys Ile Ile Ala Lys Ile Ile Gly Asp
        115                 120                 125

Lys Gly Leu Gly Gly Cys Ile Val Ile Asn Gly Glu Ile Gln Asp
    130                 135                 140

<210> SEQ ID NO 122
<211> LENGTH: 141
<212> TYPE: PRT
<213> ORGANISM: Tyrophagus putrescentiae

<400> SEQUENCE: 122

Met Lys Phe Leu Ile Leu Phe Ala Leu Val Ala Val Ala Ala Ala Gly
1               5                   10                  15

Gln Val Lys Phe Thr Asp Cys Gly Lys Lys Glu Ile Ala Ser Val Ala
            20                  25                  30

Val Asp Gly Cys Glu Gly Asp Leu Cys Val Ile His Lys Ser Lys Pro
        35                  40                  45

Val His Val Ile Ala Glu Phe Thr Ala Asn Gln Asp Thr Cys Lys Ile
    50                  55                  60

Glu Val Lys Val Thr Gly Gln Leu Asn Gly Leu Glu Val Pro Ile Pro
65                  70                  75                  80

Gly Ile Glu Thr Asp Gly Cys Lys Val Leu Lys Cys Pro Leu Lys Lys
                85                  90                  95

Gly Thr Lys Tyr Thr Met Asn Tyr Ser Val Asn Val Pro Ser Val Val
            100                 105                 110

Pro Asn Ile Lys Thr Val Val Lys Leu Leu Ala Thr Gly Glu His Gly
        115                 120                 125

Val Leu Ala Cys Gly Ala Val Asn Thr Asp Val Lys Pro
    130                 135                 140

<210> SEQ ID NO 123
<211> LENGTH: 135
<212> TYPE: PRT
<213> ORGANISM: Euroglyphus maynei

<400> SEQUENCE: 123

Val Ala Ala Val Ala Ala Asp Gln Val Asp Val Lys Asp Cys Ala Asn
1               5                   10                  15

His Glu Ile Lys Lys Val Met Val Pro Gly Cys Lys Gly Ser Glu Pro
            20                  25                  30

Cys Val Ile His Arg Gly Thr Ala Phe Gln Leu Glu Ala Val Phe Asp
        35                  40                  45

Ala Asn Gln Asn Ser Asn Ala Lys Ile Glu Ile Lys Ala Thr Ile
    50                  55                  60

Asp Gly Val Glu Ile Asp Val Pro Gly Ile Asp Asn Asn Leu Cys His
65                  70                  75                  80

Phe Met Lys Cys Pro Leu Val Lys Gly Gln Glu Tyr Asp Ile Lys Tyr
                85                  90                  95

Thr Trp Asn Val Pro Arg Ile Ala Pro Lys Ser Glu Asn Val Val Val
            100                 105                 110

Thr Val Lys Leu Leu Gly Asp Asn Gly Val Leu Ala Cys Ala Ile Ala
        115                 120                 125

Thr His Ala Lys Ile Arg Asp
    130                 135
```

<210> SEQ ID NO 124
<211> LENGTH: 146
<212> TYPE: PRT
<213> ORGANISM: Dermatophagoides farinae

<400> SEQUENCE: 124

Met Ile Ser Lys Ile Leu Cys Leu Ser Leu Leu Val Ala Ala Val Val
1               5                   10                  15

Ala Asp Gln Val Asp Val Lys Asp Cys Ala Asn His Glu Ile Lys Lys
            20                  25                  30

Val Met Val Asp Gly Cys His Gly Ser Asp Pro Cys Ile Ile His Arg
        35                  40                  45

Gly Lys Pro Phe Asn Leu Glu Ala Ile Phe Asp Ala Asn Gln Asn Thr
    50                  55                  60

Lys Thr Ala Lys Ile Glu Ile Lys Ala Asn Ile Asp Gly Leu Glu Val
65                  70                  75                  80

Asp Val Pro Gly Ile Asp Thr Asn Ala Cys His Tyr Ile Lys Cys Pro
                85                  90                  95

Leu Val Lys Gly Gln Gln Tyr Asp Ala Lys Tyr Thr Trp Asn Val Pro
            100                 105                 110

Lys Ile Ala Pro Lys Ser Glu Asn Val Val Thr Val Lys Leu Val
            115                 120                 125

Gly Asp Asn Gly Val Leu Ala Cys Ala Ile Ala Thr His Ala Lys Ile
    130                 135                 140

Arg Asp
145

<210> SEQ ID NO 125
<211> LENGTH: 146
<212> TYPE: PRT
<213> ORGANISM: Dermatophagoides farinae

<400> SEQUENCE: 125

Met Ile Ser Lys Ile Leu Cys Leu Ser Leu Leu Val Ala Ala Val Val
1               5                   10                  15

Ala Asp Gln Val Asp Val Lys Asp Cys Ala Asn Asn Glu Ile Lys Lys
            20                  25                  30

Val Met Val Asp Gly Cys His Gly Ser Asp Pro Cys Ile Ile His Arg
        35                  40                  45

Gly Lys Pro Phe Thr Leu Glu Ala Leu Phe Asp Ala Asn Gln Asn Thr
    50                  55                  60

Lys Thr Ala Lys Ile Glu Ile Lys Ala Asn Ile Asp Gly Leu Glu Val
65                  70                  75                  80

Asp Val Pro Gly Ile Asp Thr Asn Ala Cys His Tyr Ile Lys Cys Pro
                85                  90                  95

Leu Val Lys Gly Gln Gln Tyr Asp Ala Lys Tyr Thr Trp Asn Val Pro
            100                 105                 110

Lys Ile Ala Pro Lys Ser Glu Asn Val Val Thr Val Lys Leu Val
            115                 120                 125

Gly Asp Asn Gly Val Leu Ala Cys Ala Ile Ala Thr His Ala Lys Ile
    130                 135                 140

Arg Asp
145

<210> SEQ ID NO 126
<211> LENGTH: 146

<212> TYPE: PRT
<213> ORGANISM: Dermatophagoides farinae

<400> SEQUENCE: 126

Met Ile Ser Lys Ile Leu Cys Leu Ser Leu Leu Val Ala Ala Val Val
1               5                   10                  15

Ala Asp Gln Val Asp Val Lys Asp Cys Ala Asn Asn Glu Ile Lys Lys
            20                  25                  30

Val Met Val Asp Gly Cys His Gly Ser Asp Pro Cys Ile Ile His Arg
        35                  40                  45

Gly Lys Pro Phe Thr Leu Glu Ala Leu Phe Asp Ala Asn Gln Asn Thr
    50                  55                  60

Lys Thr Ala Lys Ile Glu Ile Lys Ala Asn Ile Asn Gly Leu Glu Val
65                  70                  75                  80

Asp Val Pro Gly Ile Asp Thr Asn Ala Cys His Tyr Ile Lys Cys Pro
                85                  90                  95

Leu Val Lys Gly Gln Gln Tyr Asp Ala Lys Tyr Thr Trp Asn Val Pro
            100                 105                 110

Lys Ile Ala Pro Lys Ser Glu Asn Val Val Thr Val Lys Leu Ile
        115                 120                 125

Gly Asp Asn Gly Val Leu Ala Cys Ala Ile Ala Thr His Ala Lys Ile
    130                 135                 140

Arg Asp
145

<210> SEQ ID NO 127
<211> LENGTH: 129
<212> TYPE: PRT
<213> ORGANISM: Dermatophagoides Farinae

<400> SEQUENCE: 127

Asp Gln Val Asp Val Lys Asp Cys Ala Asn Asn Glu Ile Lys Lys Val
1               5                   10                  15

Met Val Asp Gly Cys His Gly Ser Asp Pro Cys Ile Ile His Arg Gly
            20                  25                  30

Lys Pro Phe Thr Leu Glu Ala Leu Phe Asp Ala Asn Gln Asn Thr Lys
        35                  40                  45

Thr Ala Lys Ile Glu Ile Lys Ala Ser Leu Asp Gly Leu Glu Ile Asp
    50                  55                  60

Val Pro Gly Ile Asp Thr Asn Ala Cys His Phe Val Lys Cys Pro Leu
65                  70                  75                  80

Val Lys Gly Gln Gln Tyr Asp Ile Lys Tyr Thr Trp Asn Val Pro Lys
                85                  90                  95

Ile Ala Pro Lys Ser Glu Asn Val Val Val Thr Val Lys Leu Ile Gly
            100                 105                 110

Asp Asn Gly Val Leu Ala Cys Ala Ile Ala Thr His Gly Lys Ile Arg
        115                 120                 125

Asp

<210> SEQ ID NO 128
<211> LENGTH: 142
<212> TYPE: PRT
<213> ORGANISM: Dermatophagoides farinae

<400> SEQUENCE: 128

Gly Thr Met Val Ser Leu Leu Val Ala Ala Val Val Ala Asp Gln Val
1               5                   10                  15

Asp Val Lys Asp Cys Ala Asn Asn Glu Ile Lys Lys Val Met Val Asp
            20                  25                  30

Gly Cys His Gly Ser Asp Pro Cys Ile Ile His Arg Gly Lys Pro Phe
            35                  40                  45

Thr Leu Glu Ala Leu Phe Asp Ala Asn Gln Asn Thr Lys Thr Ala Lys
 50                  55                  60

Ile Glu Ile Lys Ala Ser Leu Asp Gly Leu Glu Ile Asp Val Pro Gly
65                  70                  75                  80

Ile Asp Thr Asn Ala Cys His Phe Val Lys Cys Pro Leu Val Lys Gly
                85                  90                  95

Gln Gln Tyr Asp Ile Lys Tyr Thr Trp Asn Val Pro Lys Ile Ala Pro
            100                 105                 110

Lys Ser Glu Asn Val Val Val Thr Val Lys Leu Ile Gly Asp Asn Gly
            115                 120                 125

Val Leu Ala Cys Ala Ile Ala Thr His Gly Lys Ile Arg Asp
    130                 135                 140

<210> SEQ ID NO 129
<211> LENGTH: 138
<212> TYPE: PRT
<213> ORGANISM: Dermatophagoides farinae

<400> SEQUENCE: 129

Ser Leu Leu Val Ala Ala Val Ala Asp Gln Val Asp Val Lys Asp
1               5                   10                  15

Cys Ala Asn Asn Glu Ile Lys Lys Val Met Val Asp Gly Cys His Gly
            20                  25                  30

Ser Asp Pro Cys Ile Ile His Arg Gly Lys Pro Phe Thr Leu Glu Ala
            35                  40                  45

Leu Phe Asp Ala Asn Gln Asn Thr Lys Thr Ala Lys Ile Glu Ile Lys
 50                  55                  60

Ala Ser Leu Asp Gly Leu Glu Ile Asp Val Pro Gly Ile Asp Thr Asn
65                  70                  75                  80

Ala Cys His Phe Val Lys Cys Pro Leu Val Lys Gly Gln Gln Tyr Asp
                85                  90                  95

Ile Lys Tyr Thr Trp Asn Val Pro Lys Ile Ala Pro Lys Ser Glu Asn
            100                 105                 110

Val Val Val Thr Val Lys Leu Ile Gly Asp Asn Gly Val Leu Ala Cys
            115                 120                 125

Ala Ile Ala Thr His Gly Lys Ile Arg Asp
    130                 135

<210> SEQ ID NO 130
<211> LENGTH: 129
<212> TYPE: PRT
<213> ORGANISM: Dermatophagoides farinae

<400> SEQUENCE: 130

Asp Gln Val Asp Val Lys Asp Cys Ala Asn Asn Glu Ile Lys Lys Val
1               5                   10                  15

Met Val Asp Gly Cys His Gly Ser Asp Pro Cys Ile Ile His Arg Gly
            20                  25                  30

Lys Pro Phe Thr Leu Glu Ala Leu Phe Asp Ala Asn Gln Asn Thr Lys
            35                  40                  45

Thr Ala Lys Ile Glu Ile Lys Ala Ser Leu Asp Gly Leu Glu Ile Asp
 50                  55                  60

Val Pro Gly Ile Asp Thr Asn Ala Cys His Phe Met Lys Cys Pro Leu
65                  70                  75                  80

Val Lys Gly Gln Gln Tyr Asp Ile Lys Tyr Thr Trp Asn Val Pro Lys
            85                  90                  95

Ile Ala Pro Lys Ser Glu Asn Val Val Thr Val Lys Leu Ile Gly
            100                 105                 110

Asp Asn Gly Val Leu Ala Cys Ala Ile Ala Thr His Gly Lys Ile Arg
        115                 120                 125

Asp

<210> SEQ ID NO 131
<211> LENGTH: 146
<212> TYPE: PRT
<213> ORGANISM: Dermatophagoides farinae

<400> SEQUENCE: 131

Met Ile Ser Lys Ile Leu Cys Leu Ser Leu Leu Val Ala Ala Val Val
1               5                   10                  15

Ala Asp Gln Val Asp Val Lys Asp Cys Ala Asn Asn Glu Ile Lys Lys
            20                  25                  30

Val Met Val Asp Gly Cys His Gly Ser Asp Pro Cys Ile Ile His Arg
        35                  40                  45

Gly Lys Pro Phe Thr Leu Glu Ala Leu Phe Asp Ala Asn Gln Asn Thr
    50                  55                  60

Lys Thr Ala Lys Ile Glu Ile Lys Ala Ser Leu Asp Gly Leu Glu Ile
65                  70                  75                  80

Asp Val Pro Gly Ile Asp Thr Asn Ala Cys His Phe Met Lys Cys Pro
            85                  90                  95

Leu Val Lys Gly Gln Gln Tyr Asp Ile Lys Tyr Thr Trp Asn Val Pro
            100                 105                 110

Lys Ile Ala Pro Lys Ser Glu Asn Val Val Thr Val Lys Leu Ile
        115                 120                 125

Gly Asp Asn Gly Val Leu Ala Cys Ala Ile Ala Thr His Gly Lys Ile
    130                 135                 140

Arg Asp
145

<210> SEQ ID NO 132
<211> LENGTH: 146
<212> TYPE: PRT
<213> ORGANISM: Dermatophagoides farinae

<400> SEQUENCE: 132

Met Ile Ser Lys Ile Leu Cys Leu Ser Leu Leu Val Ala Ala Val Val
1               5                   10                  15

Ala Asp Gln Val Asp Val Lys Asp Cys Ala Asn Asn Glu Ile Lys Lys
            20                  25                  30

Val Met Val Asp Gly Cys His Gly Ser Asp Pro Cys Ile Ile His Arg
        35                  40                  45

Gly Lys Pro Phe Thr Leu Glu Ala Leu Phe Asp Ala Asn Gln Asn Thr
    50                  55                  60

Lys Thr Ala Lys Ile Glu Ile Lys Ala Ser Leu Asp Gly Leu Glu Ile
65                  70                  75                  80

Asp Val Pro Gly Ile Asp Thr Asn Ala Cys His Phe Met Lys Cys Pro
            85                  90                  95

Leu Val Lys Gly Gln Gln Tyr Asp Ile Lys Tyr Thr Trp Asp Val Pro
            100                 105                 110

Lys Ile Ala Pro Lys Ser Glu Asn Val Val Thr Val Lys Leu Val
        115                 120                 125

Gly Asp Asn Gly Val Leu Ala Cys Ala Ile Ala Thr His Gly Lys Ile
    130                 135                 140

Arg Asp
145

<210> SEQ ID NO 133
<211> LENGTH: 138
<212> TYPE: PRT
<213> ORGANISM: Dermatophagoides farinae

<400> SEQUENCE: 133

Ser Leu Leu Val Ala Ala Val Val Ala Asp Gln Val Asp Val Lys Asp
1               5                   10                  15

Cys Ala Asn Asn Glu Ile Lys Lys Val Met Val Asp Gly Cys His Gly
            20                  25                  30

Ser Asp Pro Cys Ile Ile His Arg Gly Lys Pro Phe Thr Leu Glu Ala
        35                  40                  45

Leu Phe Asp Ala Asn Gln Asn Thr Lys Thr Ala Lys Ile Glu Ile Lys
    50                  55                  60

Ala Ser Leu Asp Gly Leu Glu Ile Asp Val Pro Gly Ile Asp Thr Asn
65                  70                  75                  80

Ala Cys His Phe Met Lys Cys Pro Leu Val Lys Gly Gln Gln Tyr Asp
                85                  90                  95

Ala Lys Tyr Thr Trp Asn Val Pro Lys Ile Ala Pro Lys Ser Glu Asn
            100                 105                 110

Val Val Val Thr Val Lys Leu Val Gly Asp Asn Gly Val Leu Ala Cys
        115                 120                 125

Ala Ile Ala Thr His Ala Lys Ile Arg Asp
    130                 135

<210> SEQ ID NO 134
<211> LENGTH: 129
<212> TYPE: PRT
<213> ORGANISM: Dermatophagoides farinae

<400> SEQUENCE: 134

Asp Gln Val Asp Val Lys Asp Cys Ala Asn Asn Glu Ile Lys Lys Val
1               5                   10                  15

Met Val Asp Gly Cys His Gly Ser Asp Pro Cys Ile Ile His Arg Gly
            20                  25                  30

Lys Pro Phe Thr Leu Glu Ala Leu Phe Asp Ala Asn Gln Asn Thr Lys
        35                  40                  45

Thr Ala Lys Ile Glu Ile Lys Ala Ser Leu Asp Gly Leu Glu Ile Asp
    50                  55                  60

Val Pro Gly Ile Asp Thr Asn Ala Cys His Phe Met Lys Cys Pro Leu
65                  70                  75                  80

Val Lys Gly Gln Gln Tyr Asp Ala Lys Tyr Thr Trp Asn Val Pro Lys
                85                  90                  95

Ile Ala Pro Lys Ser Glu Asn Val Val Thr Val Lys Leu Val Gly
            100                 105                 110

Asp Asn Gly Val Leu Ala Cys Ala Ile Ala Thr His Ala Lys Ile Arg
        115                 120                 125

Asp

<210> SEQ ID NO 135
<211> LENGTH: 129
<212> TYPE: PRT
<213> ORGANISM: Dermatophagoides farinae

<400> SEQUENCE: 135

```
Asp Gln Val Asp Val Lys Asp Cys Ala Asn Asn Glu Ile Lys Lys Val
1               5                   10                  15
Met Val Asp Gly Cys His Gly Ser Asp Pro Cys Ile Ile His Arg Gly
            20                  25                  30
Lys Pro Phe Thr Leu Glu Ala Leu Phe Asp Ala Asn Gln Asn Thr Lys
        35                  40                  45
Thr Ala Lys Thr Glu Ile Lys Ala Ser Leu Asp Gly Leu Glu Ile Asp
    50                  55                  60
Val Pro Gly Ile Asp Thr Asn Ala Cys His Phe Met Lys Cys Pro Leu
65                  70                  75                  80
Val Lys Gly Gln Gln Tyr Asp Ala Lys Tyr Thr Trp Asn Val Pro Lys
                85                  90                  95
Ile Ala Pro Lys Ser Glu Asn Val Val Val Thr Val Lys Leu Val Gly
            100                 105                 110
Asp Asn Gly Val Leu Ala Cys Ala Ile Ala Thr His Ala Lys Ile Arg
        115                 120                 125
Asp
```

<210> SEQ ID NO 136
<211> LENGTH: 129
<212> TYPE: PRT
<213> ORGANISM: Dermatophagoides farinae

<400> SEQUENCE: 136

```
Asp Gln Val Asp Val Lys Asp Cys Ala Asn Asn Glu Ile Lys Lys Val
1               5                   10                  15
Met Val Asp Gly Cys His Gly Ser Asp Pro Cys Ile Ile His Arg Gly
            20                  25                  30
Lys Pro Phe Thr Leu Glu Ala Leu Phe Asp Ala Asn Gln Asn Thr Lys
        35                  40                  45
Thr Ala Lys Ile Glu Ile Lys Ala Ser Leu Asp Gly Leu Glu Ile Asp
    50                  55                  60
Val Pro Gly Ile Asp Thr Asn Ala Cys His Phe Met Lys Cys Pro Leu
65                  70                  75                  80
Val Lys Gly Gln Gln Tyr Asp Ala Lys Tyr Thr Trp Asn Val Pro Lys
                85                  90                  95
Ile Ala Pro Glu Ser Glu Asn Val Val Val Thr Val Lys Leu Val Gly
            100                 105                 110
Asp Asn Gly Val Leu Ala Cys Ala Ile Ala Thr His Ala Lys Ile Arg
        115                 120                 125
Asp
```

<210> SEQ ID NO 137
<211> LENGTH: 160
<212> TYPE: PRT
<213> ORGANISM: Betula pendula

<400> SEQUENCE: 137

```
Met Gly Val Phe Asn Tyr Glu Thr Glu Thr Thr Ser Val Ile Pro Ala
```

```
            1               5                  10                 15
Ala Arg Leu Phe Lys Ala Phe Ile Leu Asp Gly Asp Asn Leu Phe Pro
            20                 25                 30
Lys Val Ala Pro Gln Ala Ile Ser Ser Val Glu Asn Ile Glu Gly Asn
            35                 40                 45
Gly Gly Pro Gly Thr Ile Lys Lys Ile Ser Phe Pro Glu Gly Phe Pro
            50                 55                 60
Phe Lys Tyr Val Lys Asp Arg Val Asp Glu Val Asp His Thr Asn Phe
65                 70                 75                 80
Lys Tyr Asn Tyr Ser Val Ile Glu Gly Gly Pro Ile Gly Asp Thr Leu
                  85                 90                 95
Glu Lys Ile Ser Asn Glu Ile Lys Ile Val Ala Thr Pro Asp Gly Gly
                  100                105                110
Ser Ile Leu Lys Ile Ser Asn Lys Tyr His Thr Lys Gly Asp His Glu
                  115                120                125
Val Lys Ala Glu Gln Val Lys Ala Ser Lys Glu Met Gly Glu Thr Leu
                  130                135                140
Leu Arg Ala Val Glu Ser Tyr Leu Leu Ala His Ser Asp Ala Tyr Asn
145                150                155                160
```

<210> SEQ ID NO 138
<211> LENGTH: 160
<212> TYPE: PRT
<213> ORGANISM: Betula pendula

<400> SEQUENCE: 138

```
Met Gly Val Phe Asn Tyr Glu Ile Glu Thr Thr Ser Val Ile Pro Ala
1               5                  10                 15
Ala Arg Leu Phe Lys Ala Phe Ile Leu Asp Gly Asp Asn Leu Val Pro
            20                 25                 30
Lys Val Ala Pro Gln Ala Ile Ser Ser Val Glu Asn Ile Glu Gly Asn
            35                 40                 45
Gly Gly Pro Gly Thr Ile Lys Lys Ile Asn Phe Pro Glu Gly Phe Pro
            50                 55                 60
Phe Lys Tyr Val Lys Asp Arg Val Asp Glu Val Asp His Thr Asn Phe
65                 70                 75                 80
Lys Tyr Asn Tyr Ser Val Ile Glu Gly Gly Pro Val Gly Asp Thr Leu
                  85                 90                 95
Glu Lys Ile Ser Asn Glu Ile Lys Ile Val Ala Thr Pro Asp Gly Gly
                  100                105                110
Cys Val Leu Lys Ile Ser Asn Lys Tyr His Thr Lys Gly Asn His Glu
                  115                120                125
Val Lys Ala Glu Gln Val Lys Ala Ser Lys Glu Met Gly Glu Thr Leu
                  130                135                140
Leu Arg Ala Val Glu Ser Tyr Leu Leu Ala His Ser Asp Ala Tyr Asn
145                150                155                160
```

<210> SEQ ID NO 139
<211> LENGTH: 160
<212> TYPE: PRT
<213> ORGANISM: Betula pendula

<400> SEQUENCE: 139

```
Met Gly Val Phe Asn Tyr Glu Ser Glu Thr Thr Ser Val Ile Pro Ala
1               5                  10                 15
Ala Arg Leu Phe Lys Ala Phe Ile Leu Glu Gly Asp Asn Leu Ile Pro
```

```
            20                  25                  30

Lys Val Ala Pro Gln Ala Ile Ser Ser Val Glu Asn Ile Glu Gly Asn
            35                  40                  45

Gly Gly Pro Gly Thr Ile Lys Lys Ile Asn Phe Pro Glu Gly Phe Pro
        50                  55                  60

Phe Lys Tyr Val Lys Asp Arg Val Asp Glu Val Asp His Thr Asn Phe
 65                  70                  75                  80

Lys Tyr Asn Tyr Ser Val Ile Glu Gly Pro Val Gly Asp Thr Leu
                85                  90                  95

Glu Lys Ile Ser Asn Glu Ile Lys Ile Val Ala Thr Pro Asp Gly Gly
            100                 105                 110

Cys Val Leu Lys Ile Ser Asn Lys Tyr His Thr Lys Gly Asn His Glu
        115                 120                 125

Val Lys Ala Glu Gln Val Lys Ala Ser Lys Glu Met Gly Glu Thr Leu
    130                 135                 140

Leu Arg Ala Val Glu Ser Tyr Leu Leu Ala His Ser Asp Ala Tyr Asn
145                 150                 155                 160

<210> SEQ ID NO 140
<211> LENGTH: 160
<212> TYPE: PRT
<213> ORGANISM: Betula pendula

<400> SEQUENCE: 140

Met Gly Val Phe Asn Tyr Glu Thr Glu Ala Thr Ser Val Ile Pro Ala
1               5                   10                  15

Ala Arg Met Phe Lys Ala Phe Ile Leu Asp Gly Asp Lys Leu Val Pro
            20                  25                  30

Lys Val Ala Pro Gln Ala Ile Ser Ser Val Glu Asn Ile Glu Gly Asn
        35                  40                  45

Gly Gly Pro Gly Thr Ile Lys Lys Ile Asn Phe Pro Glu Gly Phe Pro
    50                  55                  60

Phe Lys Tyr Val Lys Asp Arg Val Asp Glu Val Asp His Thr Asn Phe
65                  70                  75                  80

Lys Tyr Asn Tyr Ser Val Ile Glu Gly Gly Pro Val Gly Asp Thr Leu
                85                  90                  95

Glu Lys Ile Ser Asn Glu Ile Lys Ile Val Ala Thr Pro Asp Gly Gly
            100                 105                 110

Cys Val Leu Lys Ile Ser Asn Lys Tyr His Thr Lys Gly Asn His Glu
        115                 120                 125

Val Lys Ala Glu Gln Val Lys Ala Ser Lys Glu Met Gly Glu Thr Leu
    130                 135                 140

Leu Arg Ala Val Glu Ser Tyr Leu Leu Ala His Ser Asp Ala Tyr Asn
145                 150                 155                 160

<210> SEQ ID NO 141
<211> LENGTH: 160
<212> TYPE: PRT
<213> ORGANISM: Betula pendula

<400> SEQUENCE: 141

Met Gly Val Phe Asn Tyr Glu Ser Glu Thr Thr Ser Val Ile Pro Ala
1               5                   10                  15

Ala Arg Leu Phe Lys Ala Phe Ile Leu Glu Gly Asp Thr Leu Ile Pro
            20                  25                  30

Lys Val Ala Pro Gln Ala Ile Ser Ser Val Glu Asn Ile Glu Gly Asn
```

```
                35                  40                  45
Gly Gly Pro Gly Thr Ile Lys Lys Ile Thr Phe Pro Glu Gly Ser Pro
 50                  55                  60
Phe Lys Tyr Val Lys Glu Arg Val Asp Glu Val Asp His Ala Asn Phe
 65                  70                  75                  80
Lys Tyr Ser Tyr Ser Met Ile Glu Gly Gly Ala Leu Gly Asp Thr Leu
                 85                  90                  95
Glu Lys Ile Cys Asn Glu Ile Lys Ile Val Ala Thr Pro Asp Gly Gly
                100                 105                 110
Ser Ile Leu Lys Ile Ser Asn Lys Tyr His Thr Lys Gly Asp Gln Glu
                115                 120                 125
Met Lys Ala Glu His Met Lys Ala Ile Lys Glu Lys Gly Glu Ala Leu
                130                 135                 140
Leu Arg Ala Val Glu Ser Tyr Leu Leu Ala His Ser Asp Ala Tyr Asn
145                 150                 155                 160
```

<210> SEQ ID NO 142
<211> LENGTH: 160
<212> TYPE: PRT
<213> ORGANISM: Betula pendula

<400> SEQUENCE: 142

```
Met Gly Val Phe Asn Tyr Glu Ser Glu Thr Thr Ser Val Ile Pro Ala
  1               5                  10                  15
Ala Arg Leu Phe Lys Ala Phe Ile Leu Glu Gly Asp Thr Leu Ile Pro
                 20                  25                  30
Lys Val Ala Pro Gln Ala Ile Ser Val Glu Asn Ile Glu Gly Asn
                 35                  40                  45
Gly Gly Pro Gly Thr Ile Lys Lys Ile Thr Phe Pro Glu Gly Ser Pro
 50                  55                  60
Phe Lys Tyr Val Lys Glu Arg Val Asp Glu Val Asp His Ala Asn Phe
 65                  70                  75                  80
Lys Tyr Ser Tyr Ser Met Ile Glu Gly Gly Ala Leu Gly Asp Thr Leu
                 85                  90                  95
Glu Lys Ile Cys Asn Glu Ile Lys Ile Val Ala Thr Pro Asp Gly Gly
                100                 105                 110
Ser Ile Leu Lys Ile Ser Asn Lys Tyr His Thr Lys Gly Asp His Glu
                115                 120                 125
Met Lys Ala Glu His Met Lys Ala Ile Lys Glu Lys Gly Glu Ala Leu
                130                 135                 140
Leu Arg Ala Val Glu Ser Tyr Leu Leu Ala His Ser Asp Ala Tyr Asn
145                 150                 155                 160
```

<210> SEQ ID NO 143
<211> LENGTH: 160
<212> TYPE: PRT
<213> ORGANISM: Betula pendula

<400> SEQUENCE: 143

```
Met Gly Val Phe Asn Tyr Glu Thr Glu Thr Thr Ser Val Ile Pro Ala
  1               5                  10                  15
Ala Arg Leu Phe Lys Ala Phe Ile Leu Glu Gly Asp Thr Leu Ile Pro
                 20                  25                  30
Lys Val Ala Pro Gln Ala Ile Ser Ser Val Glu Asn Ile Glu Gly Asn
                 35                  40                  45
Gly Gly Pro Gly Thr Ile Lys Lys Ile Thr Phe Pro Glu Gly Ser Pro
```

```
                    50                  55                  60

Phe Lys Tyr Val Lys Glu Arg Val Asp Glu Val Asp His Ala Asn Phe
 65                  70                  75                  80

Lys Tyr Ser Tyr Ser Met Ile Glu Gly Gly Ala Leu Gly Asp Thr Leu
                     85                  90                  95

Glu Lys Ile Cys Asn Glu Ile Lys Ile Val Ala Thr Pro Asp Gly Gly
                    100                 105                 110

Ser Ile Leu Lys Ile Ser Asn Lys Tyr His Thr Lys Gly Asp His Glu
                115                 120                 125

Met Lys Ala Glu His Met Lys Ala Ile Lys Glu Lys Gly Glu Ala Leu
            130                 135                 140

Leu Arg Ala Val Glu Ser Tyr Leu Leu Ala His Ser Asp Ala Tyr Asn
145                 150                 155                 160

<210> SEQ ID NO 144
<211> LENGTH: 160
<212> TYPE: PRT
<213> ORGANISM: Betula pendula

<400> SEQUENCE: 144

Met Gly Val Phe Asn Tyr Glu Ser Glu Thr Thr Ser Val Ile Pro Ala
 1               5                  10                  15

Ala Arg Leu Phe Lys Ala Phe Ile Leu Asp Gly Asp Asn Leu Ile Pro
                 20                  25                  30

Lys Val Ala Pro Gln Ala Ile Ser Ser Val Glu Asn Ile Glu Gly Asn
                 35                  40                  45

Gly Gly Pro Gly Thr Ile Lys Lys Ile Thr Phe Pro Glu Gly Ser Pro
         50                  55                  60

Phe Lys Tyr Val Lys Glu Arg Val Asp Glu Val Asp His Ala Asn Phe
 65                  70                  75                  80

Lys Tyr Ser Tyr Ser Met Ile Glu Gly Gly Ala Leu Gly Asp Thr Leu
                     85                  90                  95

Glu Lys Ile Cys Asn Glu Ile Lys Ile Val Ala Thr Pro Asp Gly Gly
                    100                 105                 110

Ser Ile Leu Lys Ile Ser Asn Lys Tyr His Thr Lys Gly Asp His Glu
                115                 120                 125

Met Lys Ala Glu His Met Lys Ala Ile Lys Glu Lys Gly Glu Ala Leu
            130                 135                 140

Leu Arg Ala Val Glu Ser Tyr Leu Leu Ala His Ser Asp Ala Tyr Asn
145                 150                 155                 160

<210> SEQ ID NO 145
<211> LENGTH: 160
<212> TYPE: PRT
<213> ORGANISM: Betula pendula

<400> SEQUENCE: 145

Met Gly Val Phe Asn Tyr Glu Thr Glu Ala Thr Ser Val Ile Pro Ala
 1               5                  10                  15

Ala Arg Leu Phe Lys Ala Phe Ile Leu Asp Gly Asp Asn Leu Phe Pro
                 20                  25                  30

Lys Val Ala Pro Gln Ala Ile Ser Ser Val Glu Asn Ile Glu Gly Asn
                 35                  40                  45

Gly Gly Pro Gly Thr Ile Lys Lys Ile Ser Phe Pro Glu Gly Ile Pro
         50                  55                  60

Phe Lys Tyr Val Lys Gly Arg Val Asp Glu Val Asp His Thr Asn Phe
```

```
                65                  70                  75                  80

Lys Tyr Ser Tyr Ser Val Ile Glu Gly Gly Pro Val Gly Asp Thr Leu
                85                  90                  95

Glu Lys Ile Ser Asn Glu Ile Lys Ile Val Ala Thr Pro Asn Gly Gly
            100                 105                 110

Ser Ile Leu Lys Ile Asn Asn Lys Tyr His Thr Lys Gly Asp His Glu
        115                 120                 125

Val Lys Ala Glu Gln Ile Lys Ala Ser Lys Glu Met Gly Glu Thr Leu
    130                 135                 140

Leu Arg Ala Val Glu Ser Tyr Leu Leu Ala His Ser Asp Ala Tyr Asn
145                 150                 155                 160

<210> SEQ ID NO 146
<211> LENGTH: 160
<212> TYPE: PRT
<213> ORGANISM: Betula pendula

<400> SEQUENCE: 146

Met Gly Val Phe Asn Tyr Glu Ile Glu Ala Thr Ser Val Ile Pro Ala
1               5                   10                  15

Ala Arg Leu Phe Lys Ala Phe Ile Leu Asp Gly Asp Asn Leu Phe Pro
            20                  25                  30

Lys Val Ala Pro Gln Ala Ile Ser Ser Val Glu Asn Ile Glu Gly Asn
        35                  40                  45

Gly Gly Pro Gly Thr Ile Lys Lys Ile Ser Phe Pro Glu Gly Phe Pro
    50                  55                  60

Phe Lys Tyr Val Lys Asp Arg Val Asp Glu Val Asp His Thr Asn Phe
65                  70                  75                  80

Lys Tyr Ser Tyr Ser Val Ile Glu Gly Gly Pro Val Gly Asp Thr Leu
                85                  90                  95

Glu Lys Ile Ser Asn Glu Ile Lys Ile Val Ala Thr Pro Asn Gly Gly
            100                 105                 110

Ser Ile Leu Lys Ile Asn Asn Lys Tyr His Thr Lys Gly Asp His Glu
        115                 120                 125

Val Lys Ala Glu Gln Ile Lys Ala Ser Lys Glu Met Gly Glu Thr Leu
    130                 135                 140

Leu Arg Ala Val Glu Ser Tyr Leu Leu Ala His Ser Asp Ala Tyr Asn
145                 150                 155                 160

<210> SEQ ID NO 147
<211> LENGTH: 160
<212> TYPE: PRT
<213> ORGANISM: Betula pendula

<400> SEQUENCE: 147

Met Gly Val Phe Asn Tyr Glu Thr Glu Ala Thr Ser Val Ile Pro Ala
1               5                   10                  15

Ala Arg Leu Phe Lys Ala Phe Ile Leu Asp Gly Asp Asn Leu Phe Pro
            20                  25                  30

Lys Val Ala Pro Gln Ala Ile Ser Ser Val Glu Asn Ile Glu Gly Asn
        35                  40                  45

Gly Gly Pro Gly Thr Ile Lys Lys Ile Ser Phe Pro Glu Gly Phe Pro
    50                  55                  60

Phe Lys Tyr Val Lys Asp Arg Val Asp Glu Val Asp His Thr Asn Phe
65                  70                  75                  80

Lys Tyr Ser Tyr Ser Val Ile Glu Gly Gly Pro Val Gly Asp Thr Leu
```

-continued

```
                      85                  90                  95
Glu Lys Ile Ser Asn Glu Ile Lys Ile Val Ala Thr Pro Asn Gly Gly
            100                 105                 110

Ser Ile Leu Lys Ile Asn Asn Lys Tyr His Thr Lys Gly Asp His Glu
            115                 120                 125

Val Lys Ala Glu Gln Ile Lys Ala Ser Lys Glu Met Gly Glu Thr Leu
            130                 135                 140

Leu Arg Ala Val Glu Ser Tyr Leu Leu Ala His Ser Asp Ala Tyr Asn
145                 150                 155                 160
```

METHOD FOR QUANTIFICATION OF ALLERGENS

CROSS-REFERENCE TO RELATED APPLICATIONS

This application is a continuation of U.S. application Ser. No. 12/066,908, filed Mar. 14, 2008, which is a U.S. national phase of PCT/DK2006/000480, filed Sep. 1, 2006, which claims the benefit of Danish Patent Application No. PA 200501293, filed Sep. 15, 2005, and U.S. Provisional Application No. 60/717,942, filed Sep. 16, 2005, each of which is herein incorporated by reference in their entireties.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of 443266seqlist.txt, a creation date of Mar. 5, 2014 and a size of 72.7 KB. The sequence listing filed via EFS-Web is part of the specification and is hereby incorporated in its entirety by reference herein.

TECHNICAL FIELD

This invention relates to the field of quantification of allergens.

BACKGROUND OF THE INVENTION

Allergens are antigenic molecules inducing allergic responses and production of IgE antibodies in humans. They are used both for diagnosis and for treatment of allergy i.e. allergen immunotherapy, the latter in the form of allergen vaccines. Allergenic source materials to which humans are exposed, such as foods, pollens or mite faecal particles occur naturally as complex mixture(s) of major and minor allergens. Major allergens are allergens to which a majority of patients, who are allergic to the source, react. It appears, however, that any protein is a potential allergen, since still more and more minor allergens are identified as knowledge increases.

Due to the complexity of the allergen sources, the amino acid sequences of several allergens were first deduced from cDNA-derived nucleotide sequences. Cloning of genes encoding allergens revealed that most allergens are heterogeneous and that they occur as mixtures of isoallergens and variants. Amino acid sequence alignment of homologous allergens and isoallergens demonstrated that they can be identified by and/or divided into constant and variable region sequences. Constant region amino acid sequences are unique to the species however variable region amino acid sequences are unique to each of the isoallergens.

Conventional allergen specific immunotherapy and diagnosis are currently performed by use of standardized natural allergen extracts which are further formulated to allergen vaccines. These aqueous vaccines are based on allergenic natural source materials, such as tree and grass pollen, dust mite cultures and animal hair and dander particles. The composition of these natural source materials are known to vary considerably depending on time and place of collection of the allergenic source materials. Commercial allergen vaccines can furthermore be formulated to mixtures of allergens using various species.

Knowledge of the composition of the extracts and the content of essential allergens is a prerequisite for reproducibility, safety and efficacy of the final product. A major challenge in the manufacture of allergen vaccines is standardisation, i.e. securing a constant potency from batch to batch. Since the raw material is of natural origin, variation is considerable and needs to be controlled by scientifically based measures. The composition of the extract should ideally reflect the composition of the water soluble components of the allergenic source material as it is extracted on the mucosal surface of the airways and presented to the human immune system. All extracts, however, contain several allergens contributing to the total IgE-binding in different combinations for individual patients. Ideally, therefore, all components need to be controlled both qualitatively and quantitatively, but with the current technology this is not practically possible.

Standardisation is currently performed in many different ways, since each manufacturer has company specific standardisation procedures. Standardisation is performed by techniques such as SDS-PAGE, isoelectric focusing in addition to a variety of immunoelectrophoretic (QIE) and ELISA techniques using mono- and/or polyclonal antibodies and radio allergosorbent (RAST) or related techniques. An optimal batch-to-batch standardisation, such as the SQ-standardisation procedure, is essentially a three step procedure: 1) securing optimal composition and constant ratios between all components by semi-quantitative immuno-electrophoretic techniques, 2) determining major allergen components by quantitative immunoelectrophoresis, and 3) adjusting the overall IgE-binding potency as determined in Magic Lite® assays. In Europe, all standardisation is currently performed relative to an in-house company specific reference preparation, whereas in the U.S. the FDA issues standards to be used by all manufacturers. All quantitative aspects of these currently used techniques are dependent on antibodies as reagents and as such vulnerable to change over time.

Absolute quantification of specific vaccine components in complex mixtures of allergen is not straightforward and has yet not been established as a sensitive, routine high-throughput technique.

Also in the food industry routine high-through-put techniques for reliable detection and quantification of food allergens is necessary. Nuts may be found as a hidden part of a food because of accidental cross-contamination during manufacturing. Companies producing similar foods with and without e.g. nuts may have difficulty in cleaning production equipment in between making the different types of foods. Traces of previously produced foods such as nuts can remain on the equipment. The first batches of foods made without nuts that go through the same equipment will likely contain traces of nuts. Foods that may cause allergic reaction due to cross-contamination of nuts or peanuts are e.g. chocolate, candies, cookies, desserts, sweets, donuts, cereal, milkshakes, granola bars, muesli, pies, muffins, ice cream, barbecue sauce. Cows' milk may cause an allergic reaction to small amounts of milk protein from dairy products, from cows' milk, formula based on cows' milk or baby foods containing protein from milk. To avoid contamination of milk protein during production of baby foods or baby formula to milk allergic children a detection and quantification method for milk allergens is therefore needed. Reliable detection and quantification methods for food allergens are necessary in order to ensure compliance with food labelling and to improve consumer protection. Physicochemical methods e.g. mass spectrometry, as well as immunological methods have been described. The usual criteria of sensitivity, specificity, reproducibility, precision and accuracy have to be fulfilled. Still, there remain problems of cross-reactivity, of matrix effects and of food processing. Biological activity may remain when the protein is denatured.

Biological mass spectrometry (MS) was first employed to assess molecular weight and identity of proteins and peptides. In recent years, advances in mass spectrometry have resulted in techniques which can be used for quantification of a variety of biomolecules from complex mixtures such as plasma, cell and tissue samples. Earlier quantification techniques have established only relative quantification of proteins whereas the more recent techniques assess absolute quantities of molecules of interest. The rapid development of quantification techniques is mainly due to progress in the field of proteomics, particularly in applications distinguishing, for instance, healthy and diseased states and identification of marker molecules for several diseases such as cancer, rheumatoid arthritis and Alzheimers disease. The major advantage of these quantification techniques by MS is the high sensitivity of the techniques ranging from 300 amol to 300 fmol of samples.

WO 2004/070352 discloses a method for quantification of peptides relative to an internal standard using isobaric labelling reagents or sets of isobaric labelling reagents.

U.S. Pat. No. 6,872,575 discloses a method for identification of one or more proteins in complex sample mixtures without purifying the protein or obtaining its composite peptide signature.

U.S. Pat. No. 6,864,089 discloses a method for quantification using differential isotopic labelling of peptide or protein samples.

Other methods for quantification of proteins using MS techniques are e.g. the AQUA technique using internal calibration peptides synthesized with incorporated stable isotopes ($^{13}$C, $^{15}$N) to mimic native peptides formed by enzymatic digestion using e.g., trypsin (Stemmann O et al. Cell 2001; 107(6):715-26, Gerber S A et al. Proc Natl Acad Sci USA 2003; 100(12):6940-5).

Another method is the ICPL (Isotope Coded Protein Labelling) method described by Kellermann et al, Proteomics 5, 4-15, using e.g $^{12}$C/$^{13}$C$_6$-Nicotinic acid-succinimide as ICPL label.

Mass spectrometry was first introduced to the field of allergy research to characterize natural allergens including post translational modifications such as glycosylation patterns. It was further employed to characterize recombinant isoallergens and/or variants many of which have been expressed in various expression systems such as *Esherica Coli, Pichia Pastoris* and *Baculovirus* expression systems.

Johannes et al, J Allergy Clin Immunol, Vol. 110, No. 1 (2002), pages 131-138 describes the use of MS to study the actual expression of allergen isoforms identified by PCR cloning and in Swoboda et al., J. Biol Chem, Vol 270, No. 6 (1995), pages 2607-2613, liquid chromatography, MS and cDNA cloning is used to analyze isoforms of the major birch pollen allergen, Bet v 1.

There still is a need for sensitive method, however, by which active components such as allergens from the same species or different species, and/or isoallergens e.g. in a vaccine may be quantified. A method using MS techniques and the species specific and allergen specific amino acid sequences provides a very sensitive method by which the content of specific allergens or groups of allergens (isoallergens or homologous allergens) may be quantified. The method according to the invention is useful e.g. in a release assay in order to ensure a safe and accurate amount of allergen during production of a vaccine, in the final product, and also during the various stages of storage of active ingredients and/or products. The method would also be beneficial in development of second generation allergen vaccines e.g. using recombinant allergens as active ingredients. Such a method would make it possible to optimize active ingredients in second generation allergen vaccines based on the knowledge and/or composition of the current vaccines.

SUMMARY OF THE INVENTION

In accordance with the present invention, a method for absolute quantification of allergens from a plurality of sources is provided.

According to one aspect the invention provides a method for quantification of the absolute amount of an allergen in an allergen sample comprising the following steps:
a) providing a known amount of one or more allergen calibration standard peptide(s) having a sequence of amino acids which is identical with a sequence to be found in the allergen to be quantified, and optionally labelling said allergen calibration standard peptide(s),
b) degrading the allergen sample to obtain a mixture of peptides, and optionally labelling said peptides with one or more labelling agent(s),
wherein at least the peptide(s) in the degraded allergen sample or the calibration standard peptide(s) are labelled, and if both the peptides in the degraded allergen sample and the allergen calibration standard peptide(s) are labelled, the labelling agent(s) used for labelling the allergen calibration standard peptide(s) are different from the labelling agent(s) used for labelling the peptides of the degraded allergen sample,
c) quantifying the absolute amount of allergen by correlating the amount of the allergen calibration standard peptide(s) with the amount of the corresponding peptide(s) from the degraded allergen sample by mass analysis.

In one embodiment of the invention the allergen to be quantified consist of more than one isoallergen, e.g. members of an allergen group from the same species with more than >67% amino acid sequence identity.

In another embodiment of the invention the allergen to be quantified consist of more than one homologous allergens.

According to another aspect, the invention provides a method for quantification of the absolute amount of allergens in an allergen sample comprising the following steps:
a) providing a known amount of one or more allergen calibration standard peptide(s) having a sequence of amino acids which is unique for a sequence to be found in the allergen or isoallergen to be quantified, and optionally labelling said allergen calibration standard peptide(s),
b) degrading the allergen sample to obtain a mixture of peptides, and optionally labelling said peptides with one or more labelling agent(s),
wherein that at least the peptides in the degraded sample or the calibration standard peptide(s) are labelled, and if both the peptides in the degraded sample and the allergen calibration standard peptide(s) are labelled, the labelling agent(s) used for the allergen calibration standard peptide(s) are different from the labelling agent(s) used for labelling the peptides of the degraded sample,
c) quantifying the absolute amount of allergen by correlating the amount of the allergen calibration standard peptide(s) with the amount of the corresponding peptide(s) from the degraded allergen sample by mass analysis.

In one aspect of the invention, the use of a sequence of amino acids which is identical with a sequence to be found in the isoallergens or homologous allergen(s) to be quantified is provided as an allergen calibration standard peptide for absolute quantification of the allergen(s), and optionally identification. Preferably, the degradation in step b) results in a mixture of peptides where one of the peptides comprises the same amino acid sequence as the allergen calibration standard peptide.

In another aspect of the invention, the use of a sequence of amino acids which sequence is unique for the allergen or isoallergen to be quantified is provided as an allergen calibration standard peptide for absolute quantification of the allergen, and optionally identification. Preferably, the degradation in step b) results in a mixture of peptides where one of the peptides comprises the same amino acid sequence as the allergen calibration standard.

In a further aspect of the invention, a method is provided for obtaining an allergen calibration standard peptide for use in quantification of isoallergens or homologous allergens wherein the allergen calibration standard peptide is obtained by:
identification of a sequence of amino acids which is constant in the isoallergens or homologous allergens which are to be quantified, by comparison of the sequences of the isoallergens or homologous allergens and preparation of a synthetic allergen calibration standard peptide having this constant sequence.

In yet a further aspect of the invention, a method is provided for obtaining an allergen calibration standard peptide for use in quantification of an allergen or isoallergen wherein the allergen calibration standard peptide is obtained by:
identification of a variable sequence of amino acids which is unique for the allergen or isoallergen to be quantified by comparison of the sequence of the allergen or isoallergen with other isoallergens and/or homologous allergens, and preparation of a synthetic allergen calibration standard peptide having this unique sequence.

SHORT DESCRIPTION OF THE FIGURES

FIG. 1. Amino acid sequence alignment of mite group 2 allergen species (FIG. 1a) and Bet v 1 (FIG. 1b), the major birch allergen by Vector NTI software (Invitrogen). The putative amino acid sequences that can be assessed as internal calibration standard peptides (useful for quantification of isoallergens) are highlighted as bold text.

FIG. 2. Theoretical enzymatic cleavage by trypsin of house dust mite allergens, a) Der f 2 and b) Der p 2, c) Phl p 1, d) Phl p 5a e) Phl p 5b and f) Bet v 1 (GPMAW, Lighthouse data). The species specific peptides selected for the quantification assays are highlighted with bold text and gray color.

FIG. 3. a) MALDI-TOF MS fingerprint analysis of a mixture of purified and trypsin digested natural Der f 2 and Der p 2 (1:1) and b) MALDI-TOF MS fingerprint analysis of a mixture of purified and trypsin digested recombinant Der f 2 and Der p 2 (1:1).

FIG. 4. SDS-PAGE analysis of the HDM (House Dust Mite) allergen extract separated by use of hydrophobic interaction chromatography. The fractions the HDM proteins were divided into two major protein pools (I and II) and further subjected to quantification analysis.

Figure 5:
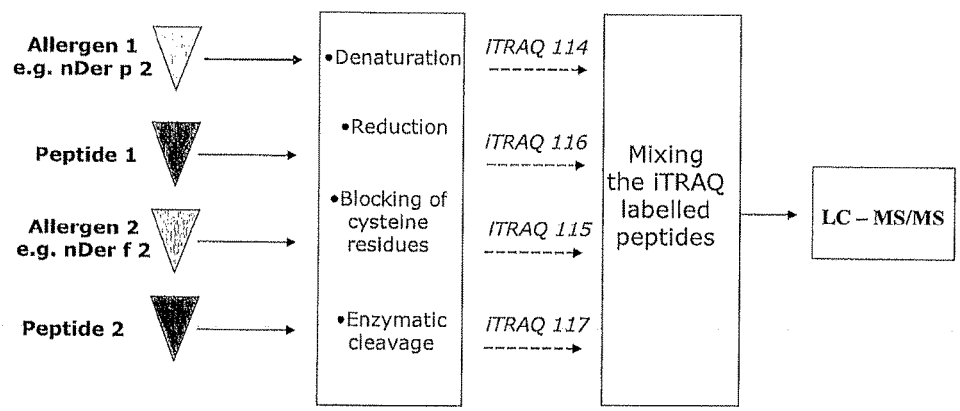

FIG. 5. A strategy for labelling of samples when employing the ITRAQ™ (Applied Biosystems, Foster City, Calif., USA) chemistry in quantification of allergens.

FIG. 6. The MS analyses of iTRAQ labelled a) Peptide 1, m/z 2353.44 (Der p 2, 32-48) b) Peptide 2, m/z 2326.35 (Der f 2, 32-48) c) trypsin digested and iTRAQ labelled nDer p 2 peptides and d) nDer f 2 peptides.

FIG. 7. MS/MS fragmentation of the mixture of nDer f 2, nDer p 2, Peptide 1 and Peptide 2. The amount of isoallergens, nDer p 2 (114.10) and Der f 2 (115.10), in the sample mixture were calculated as the ratio of the signal area of m/z 114 to area of m/z 116 (Peptide 1) and as the ratio of the area of m/z 115 to area of m/z 117 (Peptide 2).

Figure 8:
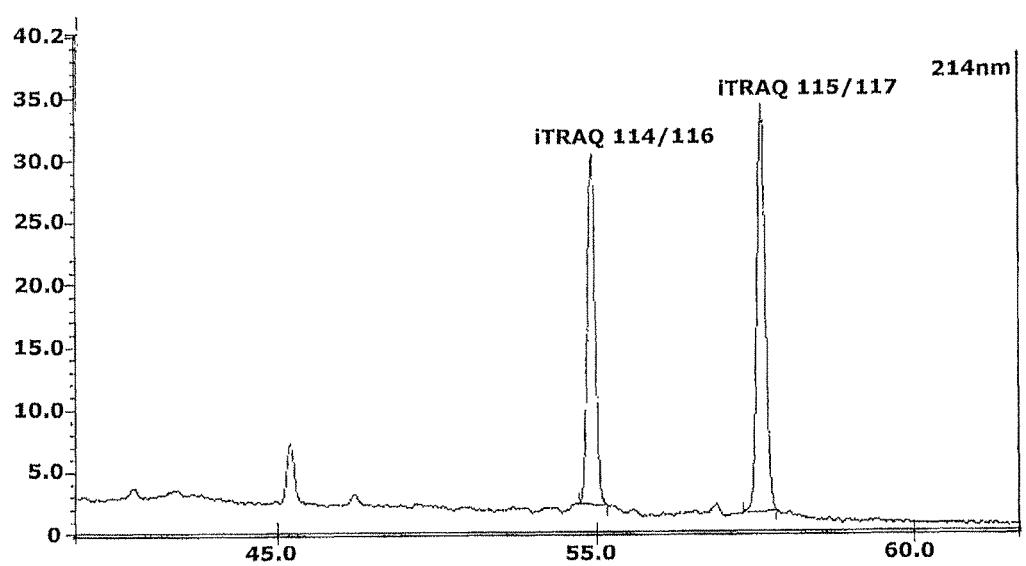

FIG. 8. Reversed phase analysis of the mixture of nDer f 2, nDer p 2, Peptide 1 and Peptide 2 from SCX chromatography. MS and MS/MS analyses were used to identify the peaks spotted on the MALDI-TOF target.

Figure 9:
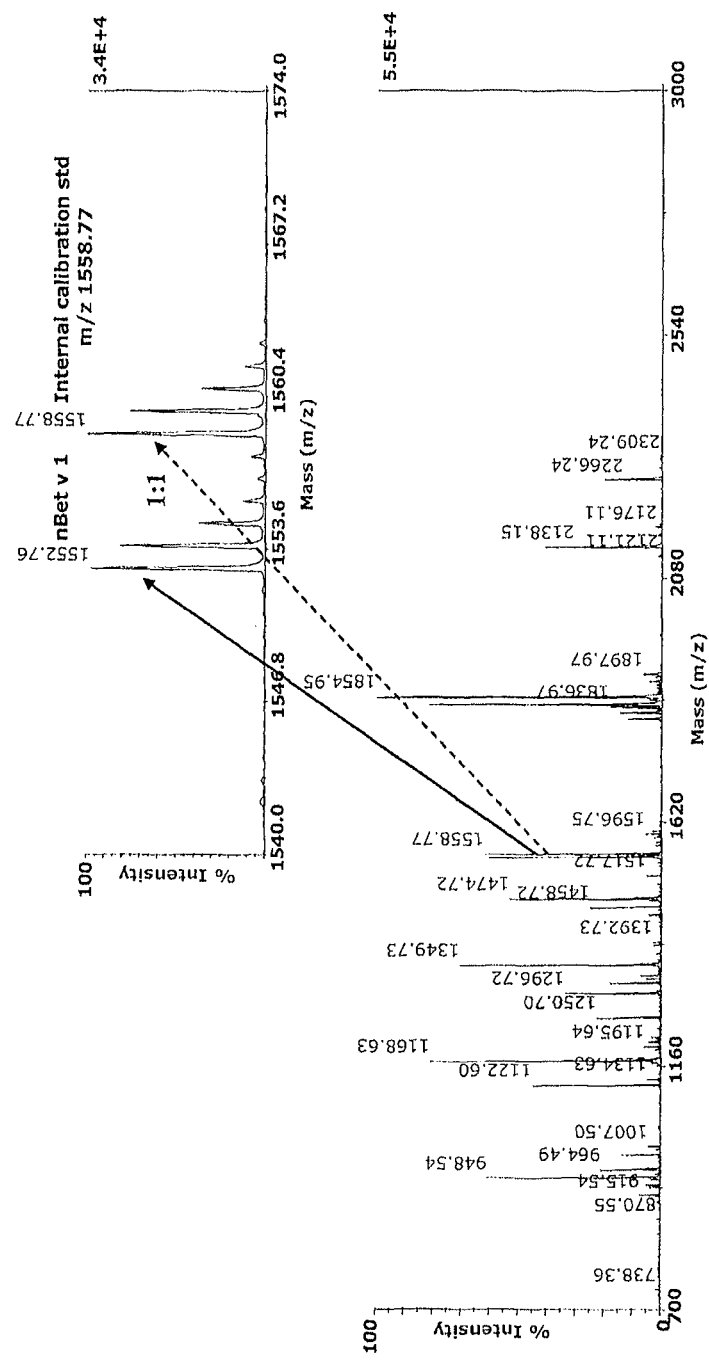

FIG. 9. MS analysis of the mixture of trypsin digested nBet v 1 and the internal calibration standard (AQUA peptide). The mass difference of 6 Da between the native peptide and the calibration standard is demonstrated in the upper corner of the figure.

DETAILED DESCRIPTION OF THE INVENTION

In the present context the term, "allergen" refers to any naturally occurring protein, a modified protein, a recombinant protein, a recombinant mutant protein, or any protein fragment thereof or mixtures of proteins that have been reported to induce allergic, i.e. IgE mediated reactions upon their repeated exposure to an individual.

Examples of naturally occurring allergens include pollen allergens (tree, weed, herb and grass pollen allergens), mite allergens (from e.g. house dust mites and storage mites), insect allergens (inhalant, saliva- and venom origin allergens), animal allergens from e.g. saliva, hair and dander from e.g. dog, cat, horse, rat, mouse, etc., fungi allergens and food allergens.

Important pollen allergens from trees, grasses and herbs are such originating from the taxonomic orders of Fagales, Oleales, Pinales and platanaceae including i.a. birch (*Betula*), alder (*Alnus*), hazel (*Corylus*), hornbeam (*Carpinus*), olive (*Olea*), cedar (*Cryptomeria* and *Juniperus*), Plane tree (*Platanus*), the order of Poales including i.a. grasses of the genera *Lolium, Phleum, Poa, Cynodon, Dactylis, Holcus, Phalaris, Secale,* and *Sorghum* and the orders of Asterales and Urticales including i.a. herbs of the genera *Ambrosia, Artemisia,* and *Parietaria*. Other important inhalation allergens are those from house dust mites of the genus *Dermatophagoides* and *Euroglyphus*, storage mite e.g *Lepidoglyphys, Glycyphagus* and *Tyrophagus*, those from cockroaches, midges and fleas e.g. *Blatella, Periplaneta, Chironomus* and *Ctenocepphalides*, and those from mammals such as cat, dog and horse, venom allergens including such originating from stinging or biting insects such as those from the taxonomic order of Hymenoptera including bees (superfamily Apidae), wasps (superfamily Vespidea), and ants (superfamily Formicoidae). Important inhalation allergens from fungi are i.a. such originating from the genera *Alternaria, Cladosporium, Aspergillus* and *Penicillium.*

Examples of food allergens are allergens from wheat (e.g. Tri a 18-19), crustacean food including shrimp (e.g. Met e 1, Pen a 1, Pen I 1, Pen m 1 and Pen m 2), prawn, crab and lobster, fish (e.g. Gad c 1 and Sal s 1), hen's eggs (e.g. Gal d 1, Gal d 2), peanut (e.g. Ara h 1-8), soy (Gly m 1-4), cows' milk (Bos d 4-8), nuts such as almond (Pru du 4), brazil nut (Ber e 1, Ber e 2), cashew nut (Ana o 1-3), hazelnut (e.g. Cor a 1.04, Cor a 2, Cor a 8) and walnut (e.g. Jug n 1-2, Jug r 1-3), celery (Api g 1, Api g 4, Api g 5), mustard (Sin a 1 and Bra j 1) and sesame seed (Ses i 1-6), and in particular allergens from wheat (e.g. Tri a 18-19), hen's eggs (e.g. Gal d 1, Gal d 2), peanut (e.g. Ara h 1-8), soy (Gly m 1-4), cows' milk (Bos d 4-8).

Examples of recombinant allergens include but are not limited to proteins/peptides from plant pollens, grass pollens, tree pollens, weed pollens, insect venom, dust and storage mite proteins, animal dander, saliva, fungal spores and food allergens (i.e., peanut, milk, gluten and egg) prepared using recombinant techniques. Recombinant allergens can be obtained e.g. on a large scale by using microbial expression systems that may be grown on fermenters, produced by recombinant DNA techniques, or chemical precursors or other chemicals when synthesized chemically. In one embodiment of the invention, the allergen is rBet v 1, rAln g 1, rCor a 1, rCar b 1, rCry j 1, rCry j 2, rOle e 1, rAmb a 1, rArt v 1, rCyn d 1, rDac g 1, rLol p 1, rLol p 5, rPhl p 1, rPhl p 5, rPoa p 1, rPoa p 5, rSor h 1, rDer f 1, rDer f 2, rDer p 1, rDer p 2, rEur m 1, rEur m 2, rGly d 1, rLep d 2, rBla g 1, rBla g 2, rFel d 1, rCan f 1, rCan f 2, rBos d 2, rEqu c 1, rEqu c 2, rMus m 1, rApis m 1, rApi m 2, rVes v 1, rVes v 2, rVes v 5, rDol m 1, rDol m 2, rDol m 5, rPol a 1, rPol a 2, rPol a 5, rAlt a 1 or rCla h 1 (r meaning recombinant).

A recombinant mutant allergen differs from the wild type in that the genes for the allergens have been modified by genetic manipulation methods such that the polypeptides which they encode exhibit substitutions, deletions and/or additions of individual or several amino acids as compared with the wild type. Examples of a recombinant mutant allergen include allergen substitution variants, addition variants, oligomers, fragments, deletion variants, hybrid molecules and other variants.

Examples of a modified allergen include allergens, which in naturally occurring form are associated with allergic disease conditions in sensitive subjects, wherein said modified recombinant allergen is altered compared to the naturally occurring allergen. Included are allergen variants containing a few amino acid exchanges, allergen mutants, oligomers, fragments, deletion variants, hybrid molecules, myristylated, glycosylated, palmitoylated and phosphorylated allergens and other variants. The modified allergen can be produced by any method suitable such as a site-directed mutagenesis method, a PCR method, chemical synthesis and a mixture of these methods.

In one embodiment of the invention, the allergen to be quantified is selected from one or more of the group of Bet v 1, Aln g 1, Cor a 1 and Car b 1, Que a 1, Cry j 1, Cry j 2, Cup a 1, Cup s 1, Jun a 1, Jun a 2, Jun a 3, Ole e 1, Lig v 1, Syr v 1, Pla l 1, Pla a 1, Pla a 2, Amb a 1, Amb a 2, Amb t 5, Art v 1, Art v 2, Art v 3, Par j 1, Par j 2, Par j 3, Sal k 1, Ave e 1, Cyn d 1, Cyn d 7, Dac g 1, Fes p 1, Hol l 1, Lol p 1 and 5, Pha a 1, Pas n 1, Phl p 1, Phl p 2, Phl p 3, Phl p 4, Phl p 5, Phl p 6, Poa p 1, Poa p 5, Sec c 1, Sec c 5, Sor h 1, Der f 1, Der f 2, Der f 3, Der f 7, Der p 1, Der p 2, Der p 3, Der p 7, Der m 1, Eur m 1, Eur m 2, Gly d 1, Gly d 2, Lep d 1, Lep d 2, Blo t 1, Tyr p 2, Bla g 1, Bla g 2, Per a 1, Per a 3, Per a 7, Fel d 1, Fel d 2, Fel d 3, Fel d 4, Can f 1, Can f 2, Bos d 2, Equ c 1, Equ c 2, Equ c 3, Mus m 1, Rat n 1, Apis m 1, Api m 1, Api m 2, Ves v 1, Ves v 2, Ves v 5, Ves f 5, Ves g 5, Ves m 1, Ves m 2, Ves m 5, Ves p 5, Ves s 5, Ves vi 5, Dol m 1, Dol m 2, Dol m 5, Dol a 5, Pol a 1, Pol a 2, Pol a 5, Sol i 1, Sol i 2, Sol i 3 and Sol i 4, Alt a 1, Alt a 3, Alt a 4, Alt a 5, Alt a 6, Cla h 1, Cla h 2, Cla h 6 Asp f 1, Bos d 4, Mal d 1, Mal d 3, Gly m 1, Gly m 2, Gly m 3, Ara h 1, Ara h 2, Ara h 3, Ara h 4, Ara h 5 or hybrids of any of these.

In another embodiment of the invention, the allergen to be quantified is selected from one or more of the group of grass pollen allergens such as Phl p 1, Phl p 5, Phl p 6, Poa p 1, Poa p 5, Dac g 1, Fes p 1, Lol p 1 and Lol p 5, dust mite allergens such as Der f 1, Der f 2, Der p 1 and Der p 2, venom allergens such as Api m 1, Api m 2, Ves v 1, Ves v 2, Ves v 5, Dol m 1, Dol m 2, Dol m 5, Dol a 5, Pol a 1, Pol a 2, and Pol a 5, weed allergens such as Amb a 1, Amb a 2, Par j 1, Par o 1 and Par m 1, birch allergens such as Bet v 1, Japanese cedar allergens such as Cry j 1 and Cry j 2, cockroach allergens such as Per a 1, olive pollen allergens such as Ole e 1, cat allergens such as Fel d 1, dog allergens such as Can f 1 and Can f 2, horse allergens such as Equ c 1 and Equ c 2, mugworth allergens such as Art v 1, Art v 2, Art v 3, mold allergens such as Alt a 1, Alt a 3, Alt a 4, Alt a 5, Alt a 6, Cla h 1, Cla h 2 and Cla h 6 and fire ant allergens such as Sol i 2, Sol i 3 and Sol i 4.

In yet a further embodiment of the invention, the allergen to be quantified is selected from one or more of the group of grass pollen allergens such as Phl p 1, Phl p 5 and Phl p 6, olive pollen allergens such as Ole e 1, dust mite allergens such as Der f 1, Der f 2, Der p 1 and Der p 2, venom allergens such as Ves v 1, Ves v 2 and Ves v 5, weed allergens such as Amb a 1, Amb a 2, Par j 1, Par o 1 and Par m 1 and tree allergens such as Bet v 1, Cry j 1 and Cry j 2.

In a yet a further embodiment, the allergen to be quantified is one or more selected from the isoallergens of Der f 1, Der p 1, Der f 2 and Der p 2.

In a yet a further embodiment the allergen to be quantified is one or more selected from Phl p 1, Phl p 5, Phl p 6, Poa p 1, Poa p 5, Dac g 1, Fes p 1, Lol p 1, Lol p 5.

In a yet a further embodiment the allergen to be quantified is one or more selected from the isoallergens of Amb a 1 and Amb a 2, An allergen from a single species may consist of several closely similar molecules. These similar molecules are designated as isoallergens when they share the following common biochemical properties: a. similar molecular size; b. identical biological function, if known, e.g. enzymatic action; and c. >67% identity of amino acid sequences. In the present context, the members of an allergen group which have >67% amino acid sequence identity and are from the same species are designated as isoallergens. Each isoallergen may have multiple forms of closely similar sequences with only a few amino acids differing; these are designated as variants, and falls under the term "isoallergen" in the present context.

In the present context the term "homologous allergens" refers to allergens from different species, which are thought to share similar three-dimensional structures, molecular size, identical biological function, if known, e.g. enzymatic action and they may share structural epitopes for IgE antibodies. In a further embodiment according to the invention the homologous allergens has >20% identity of amino acid sequences and share a common constant sequence of amino acids, preferably a sequence of at least 2-20 amino acids, more preferred 4-15 and most preferred 6-10.

As an example of homologous allergens can be mentioned e.g. Amp m 2 and Ves v 2, and Der f 2 and Der p 2.

In the present context, the expression "allergen extract" refers to any extract obtained by extraction of a biological allergen source material as generally described in "Allergenic extracts", H. Ipsen et al, chapter 20 in Allergy, principle and practice (Ed. S. Manning) 1993, Mosby-Year Book, St. Louis. Such extract may be obtained by aqueous extraction of water soluble material followed by purification steps like filtration to obtain the solution i.e. the extract. The extract may then be subjected to further purification and/or processing like freeze-drying removing substantially all the water. Generally, an allergen extract comprises a mixture of proteins and other molecules. Allergen proteins are often classified as a major allergen or, an intermediate allergen, a minor allergen or no classification. An allergen extract generally comprises both major and minor allergens. Major allergens will generally constitute approximately 5-15% of an average allergen extract, more often about 10%. Classification of an allergen is based on an assessment of the clinical importance of the particular allergen and is given below. Examples of important major allergens found in an extract include grass group 1 and 5 and 6 allergens (e.g. Phl p 1, 5, and 6), dust mite group 1 and 2 allergens (e.g. Der p 1, Der p 2), tree pollen allergen 1 (Bet v 1), cedar pollen allergen 1 and 2 (e.g. Cry j 1, Cry j 2), ragweed pollen 1 and 2 (Amb a 1, Amb a 2), cat allergen 1 (i.e. Fel dl).

The expression "biological allergen source material" as used herein refers to any biological material comprising one or more allergens. Examples of such materials are acarids PMB (Pure Mite Body) or WMC (Whole Mite Culture), defatted or non-defatted pollens from e.g. grasses, herbs, weeds and trees, animal hair and dander, pelt, fungi mycelia and spores, insect bodies, venom or saliva and foods.

Biological allergen source materials may comprise contaminating materials, such as foreign pollen and plant and flower debris from an allergen pollen source material. The maximum level of accepted contamination with pollen from other species is 1%. It should also be devoid of flower and plant debris, with a limit of 5% by weight.

The term "allergen vaccine" as used in the present context comprises at least one allergen either originating from the same allergic source or originating from different allergenic sources e.g. grass group 1 and grass group 5 allergens or mite group 1 and group 2 allergens from different mite and grass species respectively, weed antigens like short and giant ragweed allergens, different fungi's allergens like *alternaria* and *cladosporium*, tree allergens like birch, hazel, hornbeam, oak and alder allergens, food allergens like peanut, soybean and milk allergens.

Preparation of vaccines is generally well known in the art. Vaccines are typically prepared as injectables either as liquid solutions or suspensions. Such vaccine may also be emulsified or formulated so as to enable nasal administration as well as oral, including buccal and sublingual, administration. The immunogenic component in question may suitably be mixed with excipients which are pharmaceutically acceptable and further compatible with the active ingredient. Examples of suitable excipients are water, saline, dextrose, glycerol and the like as well as combinations thereof. The vaccine may additionally contain other substances such as wetting agents, emulsifying agents, buffering agents or adjuvants enhancing the effectiveness of the vaccine.

According to an aspect of the invention, a method for quantification of the absolute amount of an allergen in an allergen sample is provided, comprising the following steps:
a) providing a known amount of one or more allergen calibration standard peptide(s) having a sequence of amino acids which is identical with a sequence to be found in the allergen to be quantified, and optionally labelling said allergen calibration standard peptide(s),
b) degrading the allergen sample to obtain a mixture of peptides, and optionally labelling said peptides with one or more labelling agent(s),
wherein at least the peptides in the degraded allergen sample or the calibration standard peptide(s) are labelled, and if both the peptides in the degraded allergen sample and the allergen calibration standard peptide(s) are labelled, the labelling agent(s) used for labelling the allergen calibration standard peptide(s) are different from the labelling agent(s) used for labelling the peptides of the degraded allergen sample,
c) quantifying the absolute amount of allergen by correlating the amount of the allergen calibration standard peptide(s) with the amount of the corresponding peptide(s) from the degraded allergen sample by mass analysis.

In one particular embodiment of the invention, both the calibration standard peptide(s) and peptides of the degraded sample are labelled but with different labelling agents.

In another embodiment of the invention, the calibration standard peptide(s) are labelled and peptides of the degraded sample are not labelled.

According to a further embodiment of the invention, the allergen calibration standard peptide(s) are not labelled whereas the peptides of the degraded allergen sample are labelled.

In a preferred embodiment of the invention as described above, one allergen calibration standard peptide is provided in step a). Thus, preferably, only one allergen calibration standard peptide is used for each allergen sample.

According to a further preferred embodiment of the invention the degraded sample in step b) is, when labelled, labelled with only one labelling agent.

Thus, preferably, only one allergen calibration standard peptide is provided in step a) and if labelled, the degraded sample in step b) is only labelled with one labelling agent.

Furthermore, when labelled, the calibration standard peptide is preferably labelled with only one labelling agent.

The mass analysis, e.g. the MS as such, may be carried out on mixtures of several pairs of an allergen sample and an allergen calibration standard peptide provided according to the invention, for that particular allergen sample.

In the present context, the term "allergen calibration standard peptide(s) having a sequence of amino acids which sequence is identical with a sequence to be found in the allergen(s) to be quantified" refers to an amino acid sequence region which is constant i.e. identical in the group of isoallergens of the allergen or in the homologous allergens to be quantified. According to a preferred embodiment of the invention, the allergen calibration standard peptide(s) is selected so that the degradation in step b) of the allergen (isoallergens or homologous allergens) to be quantified results in a mixture of peptides where one of the peptides in the mixture comprises the same amino acid sequence as the allergen calibration standard peptide.

It is also possible according to the invention to quantify a specific isoallergen or allergen.

According to this aspect, the invention provides a method for quantification of a specific allergen or isoallergen in an allergen sample comprising the following steps:
a) providing a known amount of one or more allergen calibration standard peptide(s) having a sequence of amino acids which is unique for a sequence to be found in the allergen or isoallergen to be quantified, and optionally labelling said allergen calibration standard peptide(s),
b) degrading the allergen sample to obtain a mixture of peptides, and optionally labelling said peptides with one or more labelling agent(s),
wherein that at least the peptides in the degraded sample or the calibration standard peptide(s) are labelled, and if both the peptides in the degraded sample and the allergen calibration standard peptide(s) are labelled, the labelling agent(s) used for the allergen calibration standard peptide(s) are different from the labelling agent(s) used for labelling the peptides of the degraded sample, c) quantifying the absolute amount of allergen by correlating the amount of the allergen calibration standard peptide(s) with the amount of the corresponding peptide(s) from the degraded allergen sample by mass analysis.

In one particular embodiment of the invention, both the calibration standard peptide(s) and peptides of the degraded sample are labelled but with different labelling agents.

In another embodiment of the invention, the calibration standard peptide(s) are labelled and the peptides of the degraded sample are not labelled.

According to a further embodiment of the invention, the allergen calibration standard peptide(s) are not labelled whereas the peptides of the degraded allergen sample are labelled.

In a preferred embodiment of the invention as described above, one allergen calibration standard peptide is provided in step a). Thus, preferably, only one allergen calibration standard peptide is used for each allergen sample.

According to a further preferred embodiment of the invention the degraded sample in step b) is, when labelled, labelled with only one labelling agent.

Thus, preferably, only one allergen calibration standard peptide is provided in step a) and if labelled, the degraded sample in step b) is only labelled with one labelling agent.

Furthermore, when labelled, the calibration standard peptide is preferably labelled with only one labelling agent.

The mass analysis, e.g. the MS as such, may be carried out on mixtures of several pairs of an allergen sample and an allergen calibration standard peptide provided according to the invention, for that particular allergen sample.

In the present context, the term "allergen calibration standard peptide(s) having a sequence of amino acids which sequence is unique for the allergen or the isoallergen to be quantified" refers to an amino acid sequence region which is variable i.e. unique for the isoallergen or the allergen which is to quantified. According to a preferred embodiment of the invention, the degradation in step b) of the allergen to be quantified results in a mixture of peptides where one of the peptides comprises the same amino acid sequence as the allergen calibration standard peptide.

The number of amino acids in the allergen calibration standard peptide is preferably in the range of 2-20 amino acids, more preferred in the range of 4-15 and most preferred in the range of 6-15. The number is dependent on the optimal enzymatic cleavage site found to match to the amino acid sequence within the sample i.e the constant or the variable region sequence when the sample is cleaved by an enzyme. Furthermore, the allergen calibration standard to be used according to the invention depends on the label and the quantification method to be used in order to give a detectable signal and fragmentation when analysed in a MS instrument.

In the present context the term "allergen sample" refers to a sample comprising one or more allergen(s).

In one embodiment of the invention, the allergen sample comprises an allergen extract, a naturally occurring purified allergen, a modified allergen, a recombinant allergen, a recombinant mutant allergen, any allergen fragment, a mixture of isoallergens, or mixtures of homologous allergens, or a combination thereof, and an allergen extract comprising artificial spiking with purified natural or recombinant allergens.

The allergen sample can be in the form of a final product such as an allergen vaccine in the form of a tablet or a solution, or a product/intermediate taken out during production such as after an extraction of a biological allergen source material or a raw material.

In a preferred embodiment of the invention, the allergen sample is in the form of an allergen extract, a final product in the form of a tablet or an intermediate product.

In one aspect of the invention, an allergen extract is provided which allergen extract is comprised of natural allergen and recombinant allergen and is obtained by quantifying the amount of allergen in a natural extract and adding recombinant allergen or natural purified allergen to the extract in order to obtain the required amount of allergen in the final extract such as a natural extract which has been artificial spiked with purified natural or recombinant allergens.

The method according to the invention makes is possible to quantify one or more allergen(s) present as isoallergens or homologous allergens and having a constant sequence of amino acids in common, from one or more species in an allergen sample simultaneously, or in one operation.

It is possible to quantify the isoallergens of a species in an allergen sample simultaneously, or in one procedure using the method according to the invention.

Depending on the sample, it can be necessary to use denaturants and buffer solutions in order to obtain an appropriate solution.

In case the sample contains substances such as thiols e.g. DTT or mercaptoethanol, high concentrations of detergent and/or denaturants such as SDS, octyl B-D-glucopyranoside and Triton® X-100 and/or active proteases or primary amines (other than the allergen of interests), which may interfere with the method according to the invention the sample preparation can involve various treatments e.g. precipitation with acetone. Recommended buffers and alternative detergents and/or denaturants and substances which may interfere with the method according to the invention are listed in e.g. Applied Biosystems iTRAQ™ Reagents Amine-Modifying Labeling Reagents for Multiplexed Relative and Absolute Protein Quantification Protocol from Applied Biosystems, Foster City, Calif., USA.

Depending on the complexity of the sample, it might be beneficial to pre-fractionate the sample before degradation e.g. if there are molecules interfering with the detection of the allergen(s) of interest in the sample. The sample may also need to be separated/eluted from its formulation and/or any adjuvant e.g. aluminium hydroxide or calcium phosphate. In order to obtain a less complex mixture, the sample can be fractionated by use of various chromatography techniques such as hydrophobic interaction, ion exchange and/or immunoaffinity chromatography.

In one embodiment of the invention, the allergen sample is a fraction resulting from pre-fractionation e.g. an allergen extract fraction comprising one or more isoallergens.

In one embodiment of the invention, the allergen sample is a fraction from a pre-fractionation step where the sample has been fractionated according to size, solubility, electric charge and/or ligand specificity. In a further embodiment of the invention, the pre-fractionation is performed by chromatography, such as by hydrophobic interaction chromatography, reversed-phase chromatography, ion-exchange chromatography, size exclusion chromatography or affinity chromatography e.g. by hydrophobic interaction chromatography.

An example of pre-fractionation of an intermediate product containing HDM group 1 and 2 allergens by use of hydrophobic interaction chromatography is shown in FIG. 4. The fractions containing respectively HDM group 1 and 2 allergens are separated by their physico-chemical properties and identified by immunopreciptiation. Both fractions can then be subjected to quantification studies.

In one embodiment of the invention, the allergen sample is desalted after chromatography.

In one embodiment of the invention, the allergen sample is reduced and any cysteine residue is blocked before degradation such as e.g. by alkylation.

According to the invention, the sample is degraded by treatment with one or more enzymes in order to obtain a mixture of peptides. The enzyme can be chosen to have a very predictable degradation pattern enabling that peptides are obtained that may be identified and quantified by comparison with the allergen calibration standard peptide. The enzyme can be one or more protease(s) such as e.g. two proteases or one or more other enzyme(s). Examples of proteolytic enzymes include trypsin, papain, pepsin, ArgC, LysC, V8 protease, AspN, pronase, chymotrypsin and carboxypeptidease C. For example, the proteolytic enzyme trypsin is a serine protease that cleaves peptide bonds between lysine or arginine and an unspecific amino acid to thereby produce peptides that comprise an amine terminus (N-terminus) and lysine or arginine carboxyl terminal amino acid (C-terminus). In this way, the peptides from the cleavage of the protein are predictable and their presence and/or quantity, in a sample from a trypsin digest, is indicative of the presence and/or quantity of the protein of their origin. Moreover, the free amine termini of a peptide can be a good nucleophile that facilitates its labelling. Because activity of the enzymes is predictable, the sequence of peptides that are produced from degradation of a protein of a known sequence can be predicted. With this information, "theoretical" peptide information can be generated. A determination of the "theoretical" peptide fragments in e.g. computer assisted analysis of daughter fragment ions from mass spectrometry analysis of an actual sample can therefore be used to identify one or more peptides.

In one embodiment of the invention, the allergen sample is degraded before labelling by digestion of the sample with at least one enzyme to partially, or fully degrade the sample. In a further embodiment of the invention, the enzyme is a proteolytic enzyme such as trypsin, papain, pepsin, ArgC, LysC, V8 protease, AspN, pronase, chymotrypsin or carboxypeptidase C or a combination thereof, such as selected from the group of ArgC, LysC and trypsin or a combination thereof. In yet a further embodiment of the invention, the enzyme is trypsin.

The digested sample can be prepared before labelling by any of several methods if necessary.

For those skilled in the art, it will be obvious that there are numerous possibilities for labelling the sample and the allergen calibration standard peptides in order to introduce, in a predetermined manner, different mass-modifying functionalities that makes quantification of the allergen peptides possible. Labelling can e.g. be performed as described in WO 2004/070352, U.S. Pat. No. 6,864,089, Stemmann O et al. Cell 2001; 107(6):715-26, and Gerber S A et al. Proc Natl Acad Sci USA 2003; 100(12):6940-5, which are incorporated herein by this reference.

In one embodiment of the invention, the labelling is with ITRAQ™ chemistry (Applied Biosystems, Foster City, Calif., USA).

According to this embodiment of the invention, the labelling of the degraded allergen sample and/or the calibration standard peptides is performed by set of isomeric or isobaric labelling reagents such as iTRAQ™ Reagents (Applied Biosystems, Foster City, Calif., USA). Each of these reagents contains a reactive group (RG) that reacts with the analyte and a unique reporter group (RP) that produces a unique "signature ion" in MS/MS analysis. These two groups are further linked together with a linker moiety (LK) using X and Y bonds. Labelling of the degraded allergen sample therefore yields an analyte named as RP-X-LK-Y-sample. The analysis of the analyte is performed by adjusting a mass spectrometer so that both X and Y bond fragment. Fragmentation of bond X releases the reporter from the analyte and the reporter can then be determined independently from the analyte. Fragmentation of Y bond releases RP-LK combination from the analyte. Hence, based on the fragmentation the presence and/or the amount of the reporter can be correlated with the presence and/or the amount of the analyte in the sample.

Labelling with e.g. 4 iTRAQ™ reagents, allows absolute quantification of different allergen samples simultaneously (the allergen samples are degraded and each peptide mixture is labelled different iTRAQ™ reagents. The possibility of simultaneous analysis of different allergen samples enables the comparison of the labelled peptides, the sample(s), with the known amount of calibration standard peptide(s) and thereby makes quantification and identification by use of MS/MS in one step possible.

Labelling of the samples when using the ITRAQ™ and/or other labelling reagents can be performed according to manufacturer's procedure as shown in FIG. 5.

Another method for labelling in connection with quantification of proteins using MS techniques are e.g. the AQUA technique using internal calibration peptides synthesized with incorporated stable isotopes ($^{13}C$, $^{15}N$) to mimic native peptides formed by enzymatic digestion using e.g., trypsin (Stemmann O et al. Cell 2001; 107(6):715-26, Gerber S A et al. Proc Natl Acad Sci USA 2003; 100(12):6940-5).

Another method is the ICPL (Isotope Coded Protein Labelling) method described by Kellermann et al, Proteomics 5, 4-15, using e.g $^{12}C/^{13}C_6$-Nicotinic acid-succinimide as ICPL label.

In one embodiment of the invention, the differently labelled peptide(s) and allergen calibration standard peptide(s) are labelled separately and mixed after labelling before quantification.

Depending on how the labelling of the allergen and the calibration standard peptides are performed, an appropriate way of identification may be selected.

In one embodiment of the invention, the allergen is further positively identified by comparing the labelled allergen peptide(s) and allergen calibration standard peptide(s) by peptide identification analysis.

Cation-exchange chromatography can also be used for separation of the peptides, in combination with reversed-phase chromatography as two-dimensional chromatography and for reducing the amount, if necessary, of any salts and organic compounds before MS analysis.

In one embodiment of the invention, the quantification is performed using mass spectrometry.

In a further embodiment of the invention, the identification of the allergen and/or isoallergens can be performed using tandem mass spectrometers and other mass spectrometers that are capable of selecting and fragmenting molecular ions. This is especially suitable when iTRAQ™ reagents are used for labelling.

Tandem mass spectrometers (and to a lesser degree single-stage mass spectrometers) have the ability to select and fragment molecular ions according to their mass-to-charge (m/z) ratio, and then record the resulting fragment (daughter) ion spectra. More specifically, daughter fragment ion spectra can be generated by subjecting selected ions to dissociative energy levels (e.g. collision-results in dissociation (CID)). For example, ions corresponding to labelled peptides of a particular m/z ratio can be selected from a first mass analysis, fragmented and reanalyzed in a second mass analysis. Representative instruments that can perform such tandem mass analysis include, but are not limited to, magnetic four-sector, tandem time-of flight, triple, quadrupole, ion-trap, and hybrid quadrupole time-of-flight (Q-TOF) mass spectrometers.

These types of mass spectrometers may be used in conjunction with a variety of ionization sources, including, but not limited to, electrospray ionization (ESI) and matrix assisted laser desorption ionization (MALDI). Ionization sources can be used to generate charged species for the first mass analysis where the analyses do not already possess a fixed charge. Additional mass spectrometry instruments and fragmentation methods include post source decay in MALDI-MS instruments and high-energy CID using MALDI-TOF (time of flight)-TOF MS. For a recent review of tandem mass spectrometers please see: R. Aebersold and D. Goodlett, Mass Spectrometry in Proteomics. Chem. Rev. 101: 269-295 (2001). Also see U.S. Pat. No. 6,319,476, herein incorporated by reference, for a discussion of TOF TOF mass analysis techniques.

The allergen calibration standard peptide(s) (variable or constant sequence(s)) are chosen dependent on whether the quantification to be made is of an allergen or homologues allergens or specific allergens or isoallergens.

In one embodiment of the invention, absolute quantification of an allergen (absolute amount of isoallergens of the allergen) can be made.

When using the iTRAQ™ reagents the chosen allergen calibration standard peptide(s) is labelled with an isomeric or isobaric label of the set of labels, e.g. iTRAQ-114, iTRAQ-115, iTRAQ-116 or iTRAQ-117, used to label the allergen peptides. Once the relative amount of reporter for the calibration standard peptide, or standard peptides, is determined with relation to the relative amounts of the reporter for the differentially labelled peptides, it is possible to calculate the absolute amount (often expressed in concentration and/or quantity) of all of the differentially labelled peptides in the sample mixture and thereby calculate the amount of allergen (e.g. absolute amount of isoallergen(s) from a species when the sample is an extract). The acquisition of MS and MS/MS from the ITRAQ™ labelled samples can be performed e.g. using 4700 Explorer™ software. In addition, the GPS Explorer software can be used to perform the database searches which would result in the definitive identification of the peptides from MS/MS. The obtained data can then be used for quantification based on the known amount of allergen calibration standard peptide i.e. ratio between the sample and the calibration standard peptide.

The method according to the invention is useful e.g. in a release assay in order to ensure a safe and predictable amount of allergen during production of a vaccine, and in the final product, and also during the various stages of storage of ingredients and/or products, and raw extracts. The method according to the invention is useful in development of second generation allergen vaccines e.g. using recombinant allergen as active ingredients by optimizing active ingredients in second generation allergen vaccines based on the knowledge and/or composition of the current vaccines. Current vaccines are often formulated using allergens from a number of allergen species, and the method would also be beneficial in determination of the composition of species specific allergens from these allergen mixtures. The method according to the invention can be used in cleaning validation, where trace amounts of allergen(s) are measured, release assays and analyses of intermediate and final products.

Peptides which can be used as calibration standard peptides can be made by using protein and/or nucleotide databases and cleavage analyses program(s) and/or perform in vitro mass fingerprinting experiment(s).

In the present context, the term "allergen calibration standard peptide" refers to an allergen calibration standard with an amino acid sequence identical with, either a variable or a constant sequence in a group of isoallergens or homologous allergens, depending on whether it is to be used for quantification of an allergen consisting of more than one isoallergens or homologous allergens or a specific allergen or an isoallergen. The allergen calibration peptide is preferably prepared by peptide synthesis.

In some cases, the sequence of the allergen of interest is already known. An official list of allergens can e.g. be found on the website (www.allergen.org) which is maintained by I.U.I.S Allergen Nomenclature Sub-committee. The known allergen sequences can be obtained from protein and nucleotide databases e.g. Uniprot Knowlegdebase. The protein and/or nucleotide sequences can be searched using e.g. Sequence Retrieval System (SRS), or by using keywords e.g. submitting entry name (ID), description (DE), gene name (GN), species (OS) and/or organelle (OG). Further analysis of the protein/allergen of interest is performed by using e.g. Vector NTI software (Invitrogen) and/or by use of ExPASy (Expert Protein Analysis System) proteomics server of the Swiss Institute of Bioinformatics (SIB). Sequence alignment of existing allergen isoforms and allergen species is performed using e.g. Blast search which can be used to align homologous protein and/or nucleotide sequences. Sequence alignments are providing a way to compare e.g. novel sequences with previously characterized genes and/or protein(s). The sequence alignments of homologous allergens or isoallergens can be used to demonstrate the identical (constant) and variable sequences within and between allergen species as shown in FIG. 1.

In order to obtain optimal calibration standard peptides, the cleavage analysis for allergen of interest can be simulated using cleavage (degradation) analyses program(s). Allergen sequences can be subjected to e.g. GPMAW program (Lighthouse data, Odense, Denmark) which is created to support MS analyses. Cleavage (degradation) analysis of an allergen sequence can be deduced for several known proteases such as trypsin, Asp-N and Lys-C and/or a combination of two or more of them. The resulting theoretical peptides (FIG. 2) are then used to verify the optimal degradation enzyme(s) and further to design the synthetic peptides which can be used as calibration standard peptides.

On the other hand, the calibration standard peptides can be deduced from in vitro mass fingerprinting experiment(s), where allergens are cleaved by enzyme and mixed. The species specific peptides can be detected by mass fingerprinting analyses and identified by database searches e.g. using Mascot Search engine, as described below:

Purified natural (n) Der f 2 and nDer p 2 and recombinant (r) Der f 2 (A61501) and Der p 2 (BAA01241) can be dissolved in 25 mM Tris-Cl pH 7.5, 1.0 M Urea. An aliquot of recombinant molecules (rDer f 2 and rDer p 2) and natural (nDer f 2 and nDer p 2) molecules can be mixed (e.g. 1:1) or digested as individual allergens by trypsin and mixed after that. The digestions of mixed and/or individual allergens are desalted and evaluated by mass fingerprinting. The peptides that are species specific can be identified by mass fingerprinting analyses from the mixture of these two species. The digested individual HDM 2 allergens can be mixed after digestion with trypsin and the same species specific constant sequences can be demonstrated. Based on the species specific constant sequences synthetic peptides can be designed. The quantification and the verification of the peptide sequences can be performed by labelling the individual allergens and the calibration standard peptides e.g. with ITRAQ™ reagents and analysed by tandem mass spectrometry (MS/MS).

Natural allergen extracts e.g. intermediate product of two HDM species *Dermatophagoides farinae* and *Dermatophagoides pteronyssinus* (ALK-Abelló, Hørsholm, Denmark) (1.0 mg/ml dry weight) are dissolved. In order to remove the interfering component the samples can be precipitated with acetone. The precipitate containing proteins can then be resolved into the chosen buffer. For quantification purposes, the sample(s) and the chosen synthetic peptides from the two species used as calibration standard peptide can be labelled with e.g. ITRAQ™ reagents and analysed using MS/MS.

The final product e.g. house dust mite allergen tablet is dissolved into 20 mM Na-phosphate buffer pH 7.0. In order to remove the interfering components, the sample may need to be pre-fractionated and/or precipitated with acetone. The dissolved tablet and the chosen calibration standard peptides are labelled e.g. with ITRAQ™ reagents and analysed using tandem MS/MS.

Release study; the final product e.g. 5 grass mixture(s), including 5 grass species coupled with aluminiumhydroxide is dissolved into a chosen buffer which can elute bound allergens from the aluminium hydroxide. The unbound allergens can be further separated and/or desalted into a chosen digestion buffer and the chosen calibration standard peptides can be labelled e.g. with ITRAQ™ reagents and the quantification can be assessed using MS/MS.

All aspects or features mentioned in connection with any of the methods of the invention are naturally equally relevant to any of the other methods according to the invention.

EXAMPLES

Example 1

Identification of Unique Constant Regions for Natural Der f 2, Der p 2, Phl p 1, Phl p 5 and Bet v 1 and Synthetic Calibration Standard Peptides The absolute quantification of the isoallergens using the unique constant region sequences i.e. signature peptides in natural Der f 2, Der p 2, Phl p 1, Phl p 5 and Bet v 1 was demonstrated by employing two different approaches. Two calibration standard peptides were synthesized to assess iTRAQ™ labelling technique (Applied Biosystems). In addition, four calibration standard peptides were synthesized to assess stable isotope labelling technique such as Protein-AQUA™ (Sigma-Aldrich).

Allergen calibration standard peptides having species specific sequences corresponding to the amino acid sequence of 32-48 in Der f 2 and in Der p 2, 149-158 in Phl p 1, 123-135 in Phl p 5a, 115-127 in Phl p 5b a and 151-164 in Bet v 1 were designed based on the amino acid sequence alignments (Vector NTI) (FIG. 1), cleavage analyses by GPMAW (FIG. 2) and Blast database searches. The in vitro mass fingerprinting analyses of trypsin digested natural allergens Der f 2, Der p 2, Phl p 1. Phl p 5, Bet v 1 and mixed Der f 2 and Der p 2 were performed to demonstrate the occurrence of the species specific peptides. All the in vitro digested samples and mixture(s) were identified by use of the Mascot search engine (Matrix Science Inc., Boston, Mass., USA).

Synthetic peptides corresponding to the amino acid sequence of 32-48 in Der f 2 and Der p 2 were be obtained from Sigma GENOSYS, Texas, US. The concentration of the peptides was determined by the amino acid analyses (Sigma GENOSYS, Texas, US). Stable isotope labelled synthetic peptides (Protein-AQUA™ peptides) corresponding to the amino acid sequence of 149-158 in Phl p 1 (Arg $^{13}C^{15}N$), 123-135 in Phl p 5a (Arg $^{13}C^{15}N$), 115-127 in Phl p 5b a (Arg $^{13}C^{15}N$) and 151-164 in Bet v 1 (Val $^{13}C^{15}N$) were obtained from Sigma GENOSYS, Texas, US (Table 1).

Example 2

Purification of Natural and Recombinant Grass, Birch and Mite Group 2 Allergens

Natural Der f 2 and Der p 2 were purified from 100 mg of *Dermatophagoides farinae* and *Dermatophagoides pteronyssinus* extracts (ALK-Abelló, Horsholm, Denmark). Natural Phl p 1 and 5 were purified from 50 mg of *Phleum prantense* extract (ALK-Abelló) and natural Bet v 1 from 50 mg of *Betula verrucosa* extract (ALK-Abelló). The purification of the molecules was performed as described in the literature (Johannessen B R et al. FEBS Lett 2005; 579: 1208-12, Aasmul-Olsen S. et al. New Horizons in Allergy Immunotherapy, edit by Sehon et al. Plenum Press. New York 1996, p. 261-65, Petersen A et al. Clin Exp Allergy. 1994 March; 24(3):250-6, Ipsen H & Lowenstein H J Allergy Clin Immunol. 1983; 72(2):150-59). Recombinant Der f 2 and Der p 2 were expressed in *Pichia pastoris* expression system and purified as described in the literature (Johannessen B R et al. FEBS Lett 2005; 579:1208-12). The proteins were stored as freeze dried aliquots in −20° C.

The concentration of the purified allergens were measured using the extinction coefficient of one of the isoallergens at $A_{280}$ and by use of Lambda 800 UV/VIS Spectrometer (Perkin Elmer Instruments, CA, USA).

Example 3

Pre-Fractionation of HDM Extracts and Protein Digestions

Hydrophobic interaction chromatography was used to pre-fractionate the *Dermatophagoides farinae* (Der f) and *Dermatophagoides pteronyssinus* (Der p) extracts. The fractionation of the mite extracts was performed with a 1.0 ml HiTrap Phenyl column (GE-Healthcare, Uppsala, Sweden). The column was equilibrated with 50 mM Na-phosphate buffer (Merck, Darmstadt, Germany), pH 7.0, 1.0 M ammonium sulphate (Fluka, Buchs, Switzerland) and the bound sample was eluted with 50 mM Na-phosphate buffer (Merck), pH 7.0 in 5 column volumes using a decreasing linear gradient. The chromatography was performed separately for each of the HDM extracts, Der f and Der p. The fractions were analysed by SDS-PAGE (Invitrogen, Carlsbad, Calif., USA) and based on this analyses the HDM proteins were divided into two major protein pools (FIG. 4). The Der f and Der p pools containing HDM 2 allergens were subjected to a dialysis step against 10 mM ammonium bicarbonate (BDH, Poole, England). The dialysed Der f and Der p pools were freeze dried, aliquated in ~5 mg (dry weight) vials and stored frozen at −20° C. The Der f and Der p aliquots containing HDM 2 allergens were further subjected to the absolute quantification studies.

Example 4

Enzymatic Cleavage and iTRAQ Labelling iTRAQ™ labelling was employed from three samples sets:
a) 15 µg of natural Der f 2 and 15 µg of natural Der p 2
b) 15 µg recombinant Der f 2 and 15 µg of recombinant Der p 2 and
c) 100 µg of pre-fractionated Der f and Der p extracts.

The synthetic standard peptides, 15 µg Peptide 1 (Der p 2) and 15 µg Peptide 2 (Der f 2) were dissolved into a 100 mM Triethyl ammonium bicarbonate (TEAB) pH 8.5 and labelled to be used as internal calibration standards for each of the experiment sets as described below.

The blocking of free cysteine residues, the enzymatic cleavage using trypsin and the peptide labelling with iTRAQ™ reagents was performed according to the manufacturer's protocol:

Each of the six protein samples and the two internal calibration standards were dissolved into 20 µl of 100 mM TEAB, pH 8.5. The protein samples were denatured with 1.0 µl of 0.05% SDS and reduced by 2.0 µl of 4.8 mM TCEP Tris(2-carboxyethyl)phosphine at 60° C. following blocking of the cysteine residues by 1.0 µl of 10 mM s-methyl methanethiosulfonate (MMTS) at the room temperature. The protein samples were digested with 10% (w/w) Seq. grade modified trypsin (Promega, Madison, Wis., USA) for 18 hours at 37° C.

The iTRAQ™ labelling of the trypsin digested samples and internal calibration standard peptides, Peptides 1 and 2 were performed at room temperature. Each iTRAQ labelling reagent from 114 to 117 was dissolved into 70 µl of 70% ethanol which was then applied on the sample(s). The final volumes of the reagent mixtures were 100 µl/sample. The labelled samples were stored at −20° C.

The trypsin digested peptides of natural Der p 2, recombinant Der p 2 and Der p extract were labelled with iTRAQ-114. The trypsin digested peptides of natural Der f 2, recombinant Der f 2 and Der f extract were labelled with iTRAQ-115. The synthetic peptides Peptide 1 (Der p 2) and Peptide 2 (Der f 2) were labelled with iTRAQ-116 (Der p 2) and iTRAQ-117 (Der f 2) (FIG. 5). Each of the labelled samples were analysed by Voyager STR and/or 4700 Proteomic Analyser (Applied Biosystems) to demonstrate the labelling of the peptides. The MS/MS fragment analyses were performed with 4700 Proteomic Analyser (Applied Biosystems). The labelled samples were diluted 1:10 and 1.0 µl of the sample(s) was desalted by C18 Micro columns (ZipTips, Millipore) and/or handmade C18 micro columns (Poros R2, Applied Biosystems). The sample was eluted on the target by 1.0 µl 70% acetonitrile (ACN), 0.1% Trifluoro acetic acid (TFA) and 1.0 µl of alpha-cyano-4-hydroxy-cinnamic acid (CHCA) (Agilent Technologies, Böblingen, Germany) matrix was added on top of the sample. The sample was dried and subjected to MS analyses.

The MS analyses of the iTRAQ™ labelled internal calibration standards revealed masses corresponding to Peptide 1 at the m/z 2353.44 and Peptide 2 at the m/z 2326.35 (FIGS. 6a and 6b). The results showed that the modification in the Der p 2 specific Peptide 1 and Der f 2 specific Peptide 2 corresponded to the modification by the iTRAQ™ reagent when bound to the in the amino-terminus and the C-terminal Lysine. The MS analyses of the iTRAQ™ labelled natural and recombinant Der p 2 peptides revealed iTRAQ™ modified massed at m/z 2353.29. Similarly, MS analyses of the labelled natural and recombinant Der f 2 peptides revealed the iTRAQ™ modified peptide at m/z 2326.29, respectively (FIGS. 6c and 6d). No missed cleavages by trypsin were observed. These results show that the iTRAQ labelled Peptides 1 and 2 can be used as internal calibration standards for absolute quantification assays of Der p 2 and Der f 2 isoallergens.

Example 5

Absolute Quantification from the Mixture of Two Different HDM Species

The absolute quantification of the isoallergens of *Dermatophagoides farinae* and *Dermatophagoides pteronyssinus* species was first employed from the direct mixture of the purified natural allergens. The iTRAQ™ labelled natural tryptic Der p 2, Der f 2 and Peptides 1 and 2 were mixed in ration of 1:1:1:1, diluted 1:5 and 1:10 and desalted by handmade C18 micro columns (Poros R2, Applied Biosystems). The sample was eluted on the target by using 1.0 µl of 5 µg/µl of CHCA (Sigma) in 70% ACN (Sigma), 0.1% TFA (Fluka). The MS/MS fragment analyses was performed by 4700 Proteomic Analyser (Applied Biosystems).

The fragment analyses of m/z 2353.29 revealed signals at m/z 114 and m/z at 116 corresponding to the reporter ions for natural Der p 2 and Peptide 1. The amount of natural Der p 2 isoallergens in the sample was calculated as the ratio of the signal area of m/z 114 to area of m/z 116, the internal calibration standard (FIG. 7a). The MS/MS fragment analyses of m/z 2326.29 revealed the signals at m/z 115 and m/z at 117 corresponding to the reporter ions for natural Der f 2 and Peptide 2.

The amount of natural Der f 2 isoallergens in the sample was calculated as the ratio of the signal area of m/z 115 to m/z of 117, the internal calibration standard (FIG. 7b). In addition to the absolute quantification the fragment ion peak lists of m/z 2353.29 and m/z 2326.29 were submitted for database analyses by Mascot search engine (Matrix Science). The database analyses resulted identification of the peptides as 32-48 of *Dermatophagoides farinae* and *Dermatophagoides pteronyssinus* HDM allergens 2.

Example 6

Separation of the Labelled Peptide Mixtures by Two-Dimensional Chromatography

The absolute quantification of the mixture of recombinant Der f 2 and Der p 2 and the isoallergens in the complex mixture of Der f and Der p extracts was assessed by two-dimensional chromatography. Cation exchange chromatography (SCX) was assessed as the first dimension and reversed-phase chromatography as the second dimension separation step.

Recombinant Der p 2, Der f 2 and Peptides 1 and 2 were mixed in a ratio of 1:1:1:1, in a final volume of 50 µl. Der f and Der p extracts and Peptides 1 and 2 were mixed in ration 4:4:1:1, in a final volume of 50 µl.

Separation of the Labelled Peptide Mixtures by Cation Exchange Chromatography (Both Recombinant Der p 2 and Der f 2 and Extracts of Der p 2 and Der f 2):

The sample mixtures were diluted 1:10 into 5% ACN (Sigma) 0.05% Formic acid (Merck) and subjected to SCX. The SCX was performed in 0.8×50 mm Zorbax BIO-SCX (3.5 µm) column (Agilent Technologies) in a SMART™ system (GE-HealthCare, Uppsala, Sweden). The column was equilibrated with 5% ACN (Sigma) 0.05% Formic acid (Merck) and the chromatography was performed with a increasing linear gradient from 0 to 100% of 5% ACN (Sigma) 0.05% Formic acid (Merck) 0.5 M NaCl (Merck) in 30 min. The flow rate was 50 µl/min and the chromatography was monitored at 214 nm. The 50 µl fractions were collected and 1.0 µl of each fraction was analysed by Voyager-STR MS (Applied Biosystems) and/or 4700 Proteomic Analyser (Applied Biosystems) instruments. Peptides at m/z 2353.29 and m/z 2326.29 were identified eluting in the end of the gradient together with some other HDM peptides. The Der f and Der p mixture fractions (the extracts) containing the peptides at m/z 2353.29 and m/z 2326.29 were chosen to be further separated by reversed-phase chromatography, see below. However, the quantification of the mixture of rDer f 2 and rDer p 2 (recombinant) and the internal calibration standards was performed directly after SCX from the target plate.

The MS/MS fragment analyses of m/z 2353.29 revealed signals at m/z 114 and m/z at 116 corresponding to the reporter ions for Der p 2 and Peptide 1. The amount of Der p 2 clone the rDer p 2/rDer f 2 mixture was calculated as the ratio of the signal area of m/z 114 to area of m/z 116, the internal calibration standard. The MS/MS fragment analyses of m/z 2326.29 revealed the signals at m/z 115 and m/z at 117 corresponding to the reporter ions for Der f 2 and Peptide 2. The amount of Der f 2 clone in the in the rDer p 2/rDer f 2 mixture was calculated as the ratio of the signal area of m/z 115 to m/z of 117, the internal calibration standard. The fragment ion peak lists of m/z 2353.29 and m/z 2326.29 were submitted for database analyses by Mascot search engine (Matrix Science).

The database analyses resulted identification of the peptides as 32-48 of *Dermatophagoides farinae* and *Dermatophagoides pteronyssinus* HDM allergens 2.

The peptides at m/z 2353.29 and m/z 2326.29 in both samples; the mixture of recombinant Der f 2 and Der p 2 and the Der f and Der p extract mixtures, eluted from the SCX column with similar retention times. This experiment showed that SCX can be used as a fractionation and desalting step for the more simple sample-mixtures before the quantification of the allergens. The experiments also showed that SCX can be employed as the first dimension fractionation step for analyses of more complex mixtures of allergens such as conventional allergen extracts used in immunotherapy.

Separation of Labelled Peptides (from Extracts of Der p 2 and Der f 2) by SCX Followed by Reversed Phase Chromatography and Followed by Absolute Quantification MALDI TOF-TOF MS.

The separation of the iTRAQ™ labelled HDM peptides from SCX fractionation as described above, was performed by C18 PepMap 100 (3 µm) column (LC Packings Dionex, Sunny Vale, Calif., USA). The column was equilibrated with 0.05% TFA (Fluka), 2% ACN (Sigma). The peptides were eluted with 0.04% TFA (Fluka), 80% ACN in a gradient of 0-50%, in 80 min, 50-100%, in 120 min. The chromatography is performed with Ultimate3000 (LC Packings, Dionex) 2.0 µl/min and monitored at 210 and 214 nm. 1.0 µl of SCX the fraction was injected to the column. The fractions were collected by spotting them directly on a MALDI-TOF target plate. The spotting was performed with the Probot (LC Packings, Dionex) instrument which was connected on-line to the Ultimate3000 instrument. The spotting was performed every 30 s mixing the HCCA matrix (Agilent Technologies) to the sample in a ratio of 1:1.

The spotted samples were analysed by MS and MS/MS using 4700 Proteomic Analyser (Applied Biosystems). Peptides at m/z 2353.29 and m/z 2326.29 were identified from the spots on target and they were shown to correspond to the signals at 214 nm in the chromatography (FIG. 8). The MS/MS fragment analyses of m/z 2353.29 revealed signals at m/z 114 and m/z at 116 corresponding to the reporter ions for Der p 2 and Peptide 1. The amount of Der p 2 isoallergens in the Der p/f extract mixture was calculated as the ratio of the signal area of m/z 114 to area of m/z 116, the internal calibration standard. The MS/MS fragment analyses of m/z 2326.29 revealed the signals at m/z 115 and m/z at 117 corresponding to the reporter ions for Der f 2 and Peptide 2. The amount of Der f 2 isoallergens in the in the Der p/f extract mixture was calculated as the ratio of the signal area of m/z 115 to m/z of 117, the internal calibration standard. The fragment ion peak lists of m/z 2353.29 and m/z 2326.29 were submitted for database analyses by Mascot search engine (Matrix Science). The database analyses resulted identification of the peptides as 32-48 of *Dermatophagoides farinae* and *Dermatophagoides pteronyssinus* HDM allergens 2.

This experiment shows that reversed phase chromatography can be used as the second dimension in fractionation of the simple and/or complex mixtures of allergen extracts for quantification of isoallergens.

Example 7

Absolute Quantification of the Isoallergens Employing the AQUA Strategy

In the AQUA technique (Stemmann O et al. Cell 2001; 107(6):715-26, Gerber S A et al. Proc Natl Acad Sci USA 2003; 100(12):6940-5.) the internal calibration peptides are synthesized with incorporated stable isotopes ($^{13}C$, $^{15}N$) to mimic native peptides formed by enzymatic digestion using e.g., trypsin. The incorporation of one isotope labelled amino acid residue changes the molecular masses of the peptides typically from 6 to 10 Da. Unlike in the iTRAQ technique either the samples or the internal calibration standard(s) needs to be modified by the labelling reagents. In quantification experiments e.g. when using a LC-MS/MS, the abundance of a specific fragment ion from both the native sample peptide and the synthesized internal calibration standard can be measured as a function of reverse-phase chromatography retention time. The absolute quantification is determined by comparing the abundance of the known internal standard with the native sample peptide.

The synthetic internal calibration standard peptides for natural Phl p 1, Phl p 5 a and b form, and Bet v 1 were designed as described above (FIG. 2). The synthetic peptides are described in more detail in table 1.

TABLE 1

Labelling of the synthetic internal calibration standards

| Species | Allergen | Amino acid sequence | Theoretical mass | Modification | Modified mass |
|---|---|---|---|---|---|
| Betula verrucosa | Bet v 1 | AVESYLLAHSDAYN | 1552.73 | (Val $^{13}$C $^{15}$N) | 1558.64 |
| Phleum prantense | Phl p 1 | SAGEVEIQFR | 1135.57 | (Arg $^{13}$C $^{15}$N) | 1145.27 |
| Phleum prantense | Phl p 5a | YDAYVATLSEALR | 1471.74 | (Arg $^{13}$C $^{15}$N) | 1481.66 |
| Phleum prantense | Phl p 5b | FDSFVASLTEALR | 1455.74 | (Arg $^{13}$C $^{15}$N) | 1465.66 |

Natural Phl p 1, Phl p 5 and Bet v 1 were re-dissolved into a 25 mM Tris-Cl (Sigma), 1.0 M Urea (Fluka) pH 7.8 in a concentration of 2.5 pmol/μl. Internal calibration standards were mixed into the samples in a ratio of 1:1. The digestion was performed by 10% (w/w) Seq. grade Trypsin (Promega) in 37° C. for 18 hours. The samples were stored in −20° C.

The trypsin digested Phl p 1. Phl p 5 and Bet v 1 were analysed by MS and MS/MS using the Voyager STR and/or 4700 Proteomic Analyser (Applied Biosystems). The all samples were diluted 1:10 in 0.1% TFA (Fluka) and 1.0 μl of each sample was desalted by hand made C18 micro columns (Poros R2 Applied Biosystems).

MS analyses of the trypsin digested natural Phl p 1 revealed the native peptide at m/z 1135.60 and the internal calibration standard peptide for Phl p 1 isoallergens at m/z 1145.61 (data not shown). The MS/MS analyses of the internal calibration peptide showed fragmentation pattern which was corresponding to the unique amino acid sequence of the natural Phl p 1 isoallergens.

MS analyses of the trypsin digested natural Phl p 5 revealed the native peptide of Phl p 5a at m/z 1471.81 and the native peptide of Phl p 5b at m/z 1455.77 (data not shown). The internal calibration standard peptides for Phl p 5a and Phl p 5b isoallergens were detected at m/z 1481.83 and at m/z 1465.78. The MS/MS analyses of the internal calibration peptides showed fragmentation patterns which were corresponding to the unique amino acid sequences of the natural Phl p 5a and Phl p 5b isoallergens.

MS analyses of the trypsin digested natural Bet v1 revealed the native peptide at m/z 1552.76 and the internal calibration standard peptide for Bet v 1 isoallergens at m/z 1558.77 (FIG. 9) The MS/MS analyses of the internal calibration peptide showed fragmentation pattern which was corresponding to the unique amino acid sequence of the natural Bet v 1 isoallergens.

For the absolute quantification of Betv 1 Phl p 1, Phl p 5a and Phl p 5b isoallergens the samples can be subjected to analysis by e.g., by LC coupled-MS/MS instruments such as LCQ DecaXP (ThermoFinnigan), QSTAR® Hybrid LC/MS/MS system, and 4000 Q TRAP LC/MS/MS system (Applied Biosystems).

The experiments with the AQUA peptides showed that the stable isotope labelled synthetic peptides mimicking the native isoallergen sequences can be used for absolute quantification of isoallergens in natural Phl p 1, Phl p 5 and Bet v 1. Furthermore, database analyses of the tryptic digests did not reveal any missed cleavages by trypsin. The two dimensional chromatography the combination of SCX and RP-HPLC as described for iTRAQ chemistry can be used in fractionation of the more complex allergen mixtures of chemically identical native and synthetic internal calibration standards.

The invention claimed is:

1. A synthetic allergen calibration standard peptide consisting of an allergen peptide and a mass-modifying functionality wherein said allergen peptide consists of an amino acid sequence selected from any of SEQ ID NOs: 1, 2, 4, 7, 9, 11, 14, 15, 16, and 20, and
wherein the mass-modifying functionality is an isobaric labelling reagent.

2. The synthetic allergen calibration standard peptide according to claim 1, wherein said allergen peptide is found in more than one Der f 2 isoallergens and wherein said allergen peptide consists of an amino acid sequence selected from any of SEQ ID NOs: 1, 2, 4, 7, 9, and 11.

3. The synthetic allergen calibration standard peptide according to claim 1, wherein said allergen peptide is found in more than one Der p 2 isoallergens and wherein said allergen peptide consists of an amino acid sequence selected from any of SEQ ID NOs: 1, 14, 15, 16, 7, 20, 9, and 11.

4. The synthetic allergen calibration standard peptide according to claim 1 consisting of a mass-modifying functionality and an amino acid sequence selected from any of SEQ ID NOs: 1, 7, 9, and 11.

5. A synthetic allergen calibration standard peptide according to claim 1 consisting of a mass-modifying functionality and an amino acid sequence selected from any of SEQ ID NOs: 9 and 11.

6. The synthetic allergen calibration standard peptide according to claim 2,
wherein said isoallergens of Der f 2 are selected from the group consisting of: SEQ ID NOs: 124-136.

7. The synthetic allergen calibration standard peptide according to claim 3,
wherein said isoallergens of Der p 2 are selected from the group consisting of: SEQ ID NOs: 108-111.

* * * * *